US007989166B2

(12) United States Patent
Koch et al.

(10) Patent No.: US 7,989,166 B2
(45) Date of Patent: Aug. 2, 2011

(54) CIRCLE PROBES AND THEIR USE IN THE IDENTIFICATION OF BIOMOLECULES

(75) Inventors: Jorn Erland Koch, Ry (DK); Magnus Stougaard, Aarhus C (DK); Jakob Schwalbe Lohmann, Ry (DK)

(73) Assignee: In Situ RCP A/S (DK)

( * ) Notice: Subject to any disclaimer, the term of this patent is extended or adjusted under 35 U.S.C. 154(b) by 684 days.

(21) Appl. No.: 11/911,527

(22) PCT Filed: Apr. 10, 2006

(86) PCT No.: PCT/DK2006/050011
§ 371 (c)(1),
(2), (4) Date: Jun. 23, 2008

(87) PCT Pub. No.: WO2006/108422
PCT Pub. Date: Oct. 19, 2006

(65) Prior Publication Data
US 2010/0047773 A1  Feb. 25, 2010

(30) Foreign Application Priority Data
Apr. 12, 2005 (DK) .......................... PA 2005 00522

(51) Int. Cl.
C12Q 1/68 (2006.01)
C12N 15/55 (2006.01)
C12N 15/11 (2006.01)
(52) U.S. Cl. .......................... 435/6; 536/23.2; 536/24.33
(58) Field of Classification Search .................. None
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,800,159 A | 1/1989 | Mullis et al. | 435/172.3 |
| 5,354,668 A | 10/1994 | Auerbach | 435/91.1 |
| 5,591,609 A | 1/1997 | Auerbach | 435/91.2 |
| 5,614,389 A | 3/1997 | Auerbach | 435/91.2 |
| 5,648,245 A | 7/1997 | Fire et al. | 435/91.1 |
| 5,714,320 A | 2/1998 | Kool | 435/6 |
| 5,733,733 A | 3/1998 | Auerbach | 435/6 |
| 5,773,244 A * | 6/1998 | Ares et al. | 435/69.1 |
| 5,834,202 A | 11/1998 | Auerbach | 435/6 |
| 5,854,033 A | 12/1998 | Lizardi | 435/91.2 |
| 5,876,924 A | 3/1999 | Zhang et al. | 435/5 |
| 5,942,391 A | 8/1999 | Zhang et al. | 435/6 |
| 6,077,668 A | 6/2000 | Kool | 435/6 |
| 6,096,880 A | 8/2000 | Kool | 536/25.3 |
| 6,143,495 A | 11/2000 | Lizardi et al. | 435/6 |
| 6,183,960 B1 | 2/2001 | Lizardi | 435/6 |
| 6,210,884 B1 | 4/2001 | Lizardi | 435/6 |
| 6,218,152 B1 | 4/2001 | Auerbach | 435/91.2 |
| 6,221,603 B1 | 4/2001 | Mahtani | 435/6 |
| 6,261,808 B1 | 7/2001 | Auerbach | 435/91.1 |
| 6,329,150 B1 | 12/2001 | Lizardi et al. | 435/6 |
| 6,344,329 B1 | 2/2002 | Lizardi | 435/6 |
| 6,368,802 B1 | 4/2002 | Kool | 435/6 |
| 6,448,017 B1 | 9/2002 | Auerbach | 435/6 |
| 6,569,647 B1 | 5/2003 | Zhang et al. | 435/91.2 |
| 6,632,609 B2 | 10/2003 | Lizardi | 435/6 |
| RE38,442 E | 2/2004 | Zhang et al. | 435/5 |
| 6,740,745 B2 | 5/2004 | Auerbach | 536/23.1 |
| 6,797,474 B2 | 9/2004 | Lizardi | 435/6 |
| 6,855,523 B2 | 2/2005 | Zhang et al. | 435/91.2 |
| 2003/0087241 A1 | 5/2003 | Kool | 435/6 |
| 2004/0086892 A1 | 5/2004 | Crothers et al. | 435/6 |
| 2005/0069938 A1 | 3/2005 | Wang et al. | 435/6 |

FOREIGN PATENT DOCUMENTS

| | | |
|---|---|---|
| EP | 0 497 272 B1 | 8/1992 |
| EP | 0 500 224 A2 | 8/1992 |
| EP | 0 543 612 B1 | 5/1993 |
| EP | 0 807 186 B1 | 11/1997 |
| EP | 0 862 656 B1 | 9/1998 |
| EP | 0 915 991 B1 | 5/1999 |
| EP | 0 971 039 A2 | 1/2000 |
| JP | 04262799 A | 9/1992 |
| JP | 04304900 A | 10/1992 |
| WO | WO 92/01813 | 2/1992 |
| WO | WO 93/04198 | 3/1993 |
| WO | WO 93/09245 | 5/1993 |
| WO | WO 94/03630 | 2/1994 |
| WO | WO 95/35390 | 12/1995 |
| WO | WO 97/19193 | 5/1997 |
| WO | WO 97/20948 | 6/1997 |
| WO | WO 98/38300 | 9/1998 |
| WO | WO 99/49079 | 9/1999 |

(Continued)

OTHER PUBLICATIONS

European Patent Office, Official Communication dated Mar. 13, 2009; Application No. 06 706 145.7—1222 (English abstract).
Alsmadi, et al, "High accuracy genotyping directly from genomic DNA using a rolling circle amplification based assay", *BMC Genomics* 2003, 4, pp. 1-18.
Larsson, et al., In situ genotyping individual DNA molecules by target-primed rolling-circle amplification of padlock probes, *Nature Methods*, vol. 1, No. 3, pp. 227-232, Dec. 2004.
Dahl, et al., "Circle-to-circle amplification for precise and sensitive DNA analysis", *PNAS*, vol. 101, No. 13, pp. 4548-4553, Mar. 30, 2004.
Fire and Xu, "Rolling replication of short DNA circles", *Proc. Natl. Acad. Sci. USA* 92, pp. 4641-4645, May 1995.
White, et al., "Concatemer Chain Reaction: A Taq DNA Polymerase-Mediated Mechanism for Generating Long Tandemly Repetitive DNA Sequences", *Analytical Biochemistry* 199, pp. 184-190, (1991).
Ijdo, et al., "Improved telomere detection using a telomere repeat probe (TAGGG), generated by PCR", *Nucleic Acids Research*, vol. 19, No. 17, p. 4780, Apr. 30, 1991.

(Continued)

*Primary Examiner* — James Martinell
(74) *Attorney, Agent, or Firm* — Sunstein Kann Murphy & Timbers LLP

(57) ABSTRACT

The present invention provides oligonucleotides and methods for efficient detection of target nucleic acids using rolling circle replication. In one aspect, the oligonucleotides of the invention are characteristic in that they can be circularised without an external ligation template. In another aspect, the oligonucleotides of the invention are characteristic in that they can generate a free 3'end of the target nucleic acid necessary for rolling circle replication. The oligonucleotides and detection methods of the invention are useful e.g. as research tool and for diagnosis.

57 Claims, 9 Drawing Sheets

FOREIGN PATENT DOCUMENTS

| | | |
|---|---|---|
| WO | WO 00/77250 A2 | 12/2000 |
| WO | WO 01/77383 A2 | 10/2001 |
| WO | WO 02/50310 A2 | 6/2002 |
| WO | WO03/044193 A2 | 5/2003 |
| WO | WO 2004/050915 A1 | 6/2004 |
| WO | WO 2004/059005 A2 | 7/2004 |
| WO | WO 2005/001063 A2 | 1/2005 |

OTHER PUBLICATIONS

Koch, et al., "Oligonucleotide-priming methods for the chromosome-specific labelling of alpha satellite DNA in situ", *Chromosoma (Berl)* (1989) (98:259-265).

Andersen, et al., "Active, but not inactive, human centromeres display topoisornerase II activity in vivo", *Chromosome Research* 10, 305-312, 2002.

Kerem, et al., "In situ nick-translation distinguishes between active and inactive X chromosomes", *Nature*, 304, 88-90 (Jul. 7, 1983), Abstract only.

Kerem, et al., "Mapping of DNAase I Sensitive Regions on Mitotic Chromosomes", *Cell*, vol. 38, 493-499, Sep. 1984.

Jablonka, et al., "DNA hypomethylation causes an increase in DNAase-I sensitivity and an advance in the time of replication of the entire inactive X chromosome", *Chromosoma* (Berl) (1985) 93:152-156.

Nose, et al., "Detection of Carcinogen-Induced DNA Breaks by Nick Translation in Permeable Cells", *Biochemical and Biophysical Research Communications*, vol. 111, No. 2, pp. 383-389, 1983.

Filipkowski, et al., "DNA fragmentation in rat brain after intraperitoneal administration of kainate", *NeuroReport*, vol. 5(12), 1538-1540 Jul. 1994, Abstract only.

Zettl, et al., "Apoptotic cell death of T-lymphocytes in experimental autoimmune neuritis of the Lewis rat", *Neuroscience Letters*, 176 (1994) 75-79.

Gold, et al., "Differentiation between cellular apoptosis and necrosis by the combined use of in situ tailing and nick translation techniques", *Lab Invest.* Aug. 1994;71(2):219-25, Abstract only.

Luchniak, et al., "Different DNA methylation in A and B chromosomes of *Crepis capillaries* detected by in situ nick-translation. Comparison with molecular methods", *Folia Histochem Cytobiol*, 2002;40(3):325-30, Abstract only.

Andersen, et al., "CpG islands detected by self-primed in situ labeling (SPRINS)", *Chromosoma* (1998) 107:260-266.

Wu and Wallace, "The Ligation Amplification Reaction (LAR)—Amplification of specific DNA Sequences Using Sequential Rounds of Template-Dependent Ligation", *Genomics* 4, 560-569 (1989).

Kalin, et al., "Evaluation of the ligase chain reaction (LCR) for the detection of point mutations", *Mutat Res.* Oct. 1992;283(2):119-23, Abstract only.

Nilsson, et al., "Padlock Probes: Circularizing Oligonucleotides for Localized DNA Detection", *Science*, New Series, vol. 265, No. 5181, Genome Issue, (Sep. 30, 1994), pp. 2085-2088.

Nilsson et al., "Padlock probes reveal single-nucleotide differences, parent of origin and in situ distribution of centromeric sequences in human chromosomes 13 and 21", *Nature Genetics*, vol. 16, pp. 252-255, Jul. 1997.

Nilsson, et al., "Making Ends Meet in Genetic Analysis Using Padlock Probes", *Human Mutation* 19:410-415 (2002).

Gazit, et al., "Active Genes are Sensitive to Deoxyribonuclease I During Metaphase", *Science*, vol. 217, Aug. 13, 1982, pp. 648-650.

\* cited by examiner

A

B

A

B

A

B

A

B

CIRCLE PROBES AND THEIR USE IN THE IDENTIFICATION OF BIOMOLECULES

FIELD OF THE INVENTION

The invention relates to localised detection of nucleic acids in general, and of RNA in particular, through rolling circle nucleic acid synthesis using circular probes, or probes capable of forming circles, with or without endonuclease activity. In some aspects, the probes contain intra-molecular structures serving to improve their performance in the hybridisation/ligation events preceding the rolling circle nucleic acid synthesis, and in some aspects the probes contain cutting elements capable of cleaving the target nucleic acid. The invention relates to these probes, as well as to methods of their use.

BACKGROUND OF THE INVENTION

Rolling circle replication exploits the fact that replication of circular nucleic acid molecules is essentially an endless process producing repeated copies of the circle—this is how prokaryotic genomes are replicated in nature.

The research variant of the reaction employs linear oligonucleotides which are shaped into circles, typically by ligating the two ends together after they have been put in proximity by hybridisation to a ligation template. Subsequently, these circles may be copied in a rolling circle replication. This reaction is usually initiated by adding a primer to the closed circle, but as pointed out in WO 97/20948, it may equally well be initiated from the ligation template (the primary hybridisation target).

The reaction in the research setting is often referred to as a rolling circle amplification (RCA), though this should, strictly speaking, be reserved for situations where the rolling circle product is further amplified by a hyperbranch or DNA cascade reaction (WO 97/19193 and WO 97/20948).

The rolling circle product may remain a string of tandemly repeated copies of the circle, or may be reduced to monomers by digestion with a restriction enzyme or a ribozyme. This basic process is described in the patent literature (e.g. WO 98/38300) and scientific papers (e.g. Dahl F et al., Proc Natl Acad Sci USA. 101(13), 4548-53 (2004)).

Detection of specific nucleic acids by hybridisation in cell and tissue samples is of significant interest both for research and diagnostic purposes. Originally this was done by hybridisation of labelled DNA or RNA probes to the specimens (in situ hybridisation). However, the molecular resolution (ability to detect variations in the hybridisation target) and sensitivity of this approach is insufficient for a number of purposes.

A modified approach was therefore introduced, where unlabelled linear short (oligonucleotide) probes are employed to induce the synthesis of labelled DNA at the hybridisation site. This so-called PRimed IN Situ technique (PRINS, Koch et al. 1989, and many subsequent publications) provides improved resolution and sensitivity through the better discrimination among target sequences obtained with the short probes, as well as signal amplification from the site specific DNA synthesis, but only works for certain hybridisation targets.

A strategy to improve the performance of the technique was therefore proposed in WO 97/20948. According to this strategy, circular oligonucleotide probes are used in place of the linear probes, and the site-specific DNA synthesis is primed from the hybridisation target using the circle probe as template for the DNA synthesis, whereby the hybridisation target becomes extended with numerous tandemly repeated copies of the complementary sequence to the DNA circle. These copies may then be detected either through the incorporation of labelled nucleotides during the DNA synthesis, or through subsequent hybridisation to the tandem repeat. This localised production of recognizable DNA by rolling circle replication is referred to as rolling circle PRINS in the following part of this section.

Localised detection of nucleic acid molecules by rolling circle PRINS requires that the synthesis reaction is efficiently retained at the site where these molecules originally were. This can be obtained by using a free 3'-end of the target nucleic acid molecule as primer for the DNA polymerase, enabling it to initiate the rolling circle replication of the circle probe. In DNA, such ends may already be available as the result of biological processes breaking the DNA in vivo (Andersen C L. et al. *Chromosome Res.* 10(4), 305-12 (2002)) or as preparation artefacts. Such "naturally occurring" 3'-ends were employed in WO 97/20948. Alternatively, suitably placed 3'-ends can be generated using nucleases to prepare the target DNA for the reaction, if the DNA is digested with an endonuclease 3' of the target site. If the resulting end is not right next to where the circle hybridises, the target DNA is digested with an exonuclease or a polymerase having exonuclease activity to recess the 3'-end until a point where it can prime the rolling circle process. These steps can be performed before, during or after the hybridisation of the circle to the target DNA as described in WO 99/49079 and in Larsson C. et al. *Nature Methods* 1, 227-32 (2004). WO 02/50310 mentions that not only DNA but also RNA may be detected by rolling circle DNA synthesis (in solution, on slides and in paraffin sections p. 11, I.6). However, no indications are given for the preparation of the target RNA for the rolling circle process, and the tool provided for the DNA detection (restriction digestion) is not applicable to RNA targets. Additionally, the process for DNA detection requires the addition of separate rolling circle primers, and, since no difference is emphasized, this must apply to the RNA detection as well.

Thus, in conclusion, a rolling circle DNA synthesis based approach specific to the target primed detection of RNA targets was neither provided in WO 97/20948 nor mentioned in WO 02/50310.

Rolling circle detection of RNA was also suggested in WO 99/49079 and WO 01/77383. These patent applications elaborated on the basic concept of performing rolling circle detection on RNA targets by providing optimised reaction conditions for the formation of a circle probe through ligation on an RNA template, and suggest that breakage of the target molecule may be obtained with either RNase H or RNase A. However, despite optimising the conditions for probe formation, the yield of DNA circles under the optimised conditions was still significantly lower than the yield obtained when circles are formed on a DNA template. As for the digestion with RNase A, it provides random cleavage of the RNA target, and not the wanted targeted cleavage. Targeted cleavage may be obtained by digesting the RNA with RNase H, which specifically cleaves the RNA component in DNA/RNA hybrids, leading to RNA degradation exclusively at sites where the circle probe is located. Unfortunately, this degradation leads to the dislocation of the probe from its hybridisation target, so that it can no longer report on the location of that target (Koch, unpublished observation). An efficient RNA detection version of the target primed rolling circle PRINS previously described for DNA detection is thus still not published.

US2003/0087241 discloses small single stranded circular oligonucleotide templates for synthesis of oligonucleotides, preferably RNA oligonucleotides. The circular oligonucleotides further comprise means for converting synthesised multimer into monomers; such means may e.g. be a selfcleaving ribozyme. The purpose of the method disclosed is efficient, low-cost and large scale synthesis of oligonucleotides. A detection method was not contemplated.

Thus, in spite of the recent progress of the rolling circle technology there is still a need for improvements of the technique, notably to provide detection of nucleic acid sequences other than double stranded DNA sequences containing appropriately positioned restriction sites. In particular, further developments of the technique are needed, rendering site specific cleavage of single stranded nucleic acid sequences, including RNA and single stranded DNA, possible, in order to allow detection of such sequences by target primed rolling circle PRINS.

SUMMARY OF THE INVENTION

The present invention is directed to improve rolling circle techniques for the detection of nucleic acid molecules. This involves expanding the number of published circle probes from two to six (FIG. 1), partly by supplementing the known preformed circle (FIG. 1A) and padlock probes (FIG. 1C) with a third design, a self-templated (turtle) probe disclosed here, and partly by introducing a new element, the slicer, which can be added to all three probe designs (FIGS. 1E-H). For some applications it may be sufficient to place a suitable probe at or near the 3'-end of the target nucleic acid molecule, and, if necessary, recess that end to the point where the rolling circle replication can begin. For other applications, cutting of the target molecule may be needed to produce a suitably located 3'-end. The slicer is essentially a cutting element, which comprises endonuclease activity built into the probe, enabling it to produce the suitably located 3'-end. These novel probe designs enable improved detection methods based on target primed rolling circle replication, which are also disclosed here.

In a first aspect, the invention extends the span of circle probes by adding a turtle probe to the already known probes i.e. the preformed circle probe and the padlock probe. In a preferred embodiment of the invention this turtle probe (FIG. 1D) is a circular nucleic acid probe comprising
  i) A first part and a third part comprising nucleic acid sequences that are at least 75% complementary
  ii) A second nucleic acid part comprising a hairpin structure extending either from said first part or from said third part
  Further comprising a fourth nucleic acid part, which is at least 75% complementary to a target nucleic acid sequence and one or more elements defining the specific probe.

The turtle probe can be ligated using self-templated ligation, due to intramolecular hybridisation mediated through a hairpin structure and the two complementary sequences comprised within its sequence. When these complementary sequences hybridise, the 5'-end and the 3'-end of the probe are brought in proximity, enabling ligation of the probe to form a closed circular structure. Such self-templated ligation may be preferable when the ligation efficiency on the target nucleic acid molecule is low (e.g. on RNA targets or on DNA targets containing modifications resulting from degradation, preparation, or fixation, such as e.g. addition of mono-methylol (—CH$_2$OH) groups to the bases of the nucleic acids, resulting in dimerisation of adenine groups by methylene bridging).

Thus in one embodiment, the present invention can be described as a circular nucleic acid probe with a total length of 30-200 nucleotides comprising:

i) A first part and a third part comprising nucleic acid sequences that are at least 75% complementary to each other and each have a length of 3-100 nucleotides
  ii) A second nucleic acid part comprising a hairpin structure extending either from said first part or from said third part and wherein said second part has a length of 9-50 nucleotides
  iii) A fourth part comprising a sequence of nucleic acid residues, which is at least 75% complementary to a target nucleic acid sequence and wherein the length of said fourth part is 6-100 nucleotides.

In a second aspect, the invention extends the span of circle probes by the introduction of a slicer,—a cutting element which can be incorporated into any of the three probes; the turtle probe, the preformed circle probe and the padlock probe (FIGS. 1E-1H).

In another preferred embodiment of the invention, the circle probe is a turtle probe with one or more cutting elements inserted, named a slicer-turtle probe. Thus, a slicer-turtle is a circular nucleic acid probe, according to the first aspect, wherein said probe comprises one or more elements having endonuclease activity (FIG. 1H).

Alternatively, one or more cutting elements may be incorporated into a circle probe, which is a preformed circle probe or a padlock probe, so that said probe comprises one or more elements having endonuclease activity. Such preformed slicer-circle probes, or slicer-padlock probes, comprise, beside the one or more cutting elements (FIGS. 1E-F and 1G):

A first part and a third part comprising nucleic acid sequences that are at least 75% complementary to each other and each have a length of 3-100 nucleotides A second nucleic acid part comprising a hairpin structure extending either from said first part or from said third part and wherein said second part has a length of 9-50 nucleotides A fourth part comprising a sequence of nucleic acid residues, which is at least 75% complementary to a target nucleic acid sequence and wherein the length of said fourth part is 6-100 nucleotides.

If the alternative circle probe is a preformed slicer-circle probe, it may preferably be obtained by ligating the slicer-turtle probe prior to hybridisation (FIG. 1F). Alternatively it can be obtained by ligating the slicer-padlock probe prior to hybridisation (FIG. 1E), using an external ligation template.

In a third aspect, the invention relates to a method for the detection of target DNA molecules, said method comprising hybridising a circular nucleic acid probe, which is a turtle probe, with a target DNA sequence, at or near the 3'-end of the target DNA molecule, performing rolling circle replication, and detecting the rolling circle product. Alternatively, the invention relates to a method for the detection of target RNA molecules, said method comprising hybridising a circular nucleic acid probe, which is a turtle probe, a preformed circle probe, or a padlock probe, with a target RNA sequence, at or near the 3'-end of the target RNA molecule, performing rolling circle replication, and detecting the rolling circle product. This method comprises:
  i) obtaining a preparation containing the target RNA molecule, and
  ii) providing the circular nucleic acid probe, and
  iii) hybridising said probe with the target RNA molecule at or near the 3'-end of said target RNA molecule, and
  iv) effecting rolling circle replication with said probe as template, It is to be understood that any time a circle probe is found in an open circular structure it is further required to be ligated into a closed circular structure prior to rolling circle replication.

and detecting said target RNA molecule by visualising the rolling circle product.

In a fourth aspect, the invention relates to a method for the detection of a target nucleic acid molecule, said method comprising hybridising a circle probe, which is a slicer-turtle probe, a preformed slicer-circle probe, or a slicer-padlock probe, to the target nucleic acid molecule, cleaving said target nucleic acid molecule with the element having endonuclease activity to produce a 3'-end within the target nucleic acid molecule, performing rolling circle replication from said new 3'-end, and detecting the rolling circle product (FIG. 2).

This method comprises:
  i) obtaining a preparation comprising the target nucleic acid molecule, and
  ii) providing the circular nucleic acid probe, and
  iii) hybridising said probe with the target nucleic acid molecule, and
  iv) cleaving the target nucleic acid molecule with the element having endonuclease activity, producing a new 3'-end and 5'-end within the nucleic acid molecule, and
  v) effecting rolling circle replication from said new 3'-end within the target nucleic acid molecule with said probe as template and detecting said target nucleic acid molecule by visualising the rolling circle product.

It is to be understood that any time a circle probe is found in an open circular structure it is further required to be ligated into a closed circular structure prior to rolling circle replication.

In a first application aspect, the invention relates to methods for the detection of target nucleic acid sequences in situ, i.e. standard cytological or histological preparations. The circle probe is designed to recognise a target region in the target nucleic acid molecule localised in the cells or tissue, and a procedure suitable for the probe and target of choice is used.

In a second application aspect, the present invention relates to methods for the detection of target nucleic acid molecules immobilised on solid supports, said methods comprising hybridising the target nucleic acids with any of the probes mentioned, performing rolling circle replication with the probe as template, and detecting the rolling circle product. The method comprises some steps, additional to what was mentioned for the in situ application. Thus the invention e.g. relates to a method, further comprising the steps of:
  i) Providing a capture oligonucleotide attached to a solid support, and
  ii) Hybridising said capture oligonucleotide with said target nucleic acid molecule, thereby attaching the target nucleic acid molecule to the solid support.

The invention also pertains to in vitro diagnostic methods as well as kits-of-parts based on the probes of the invention.

DEFINITIONS

5'-Cap: A structure found in the 5'-end of eukaryotic mRNA comprising a terminal methylguanosine residue.

DNAzyme: A DNA sequence that can function as a sequence specific endonuclease.

10-23 DNAzyme: A DNAzyme consisting of the sequence; 5'-NNNNNN$_n$-(A/G)GGCTAGCTACAACGA-NNNNNN$_n$-3' (N being any natural or artificial nucleotide including modified nucleotides and n symbolising a random number of nucleotides). (SEQ ID NO: 21)

8-17 family: A DNAzyme consisting of the sequence: 5' NNNNNN$_n$-TN$_{a1}$N$_{a2}$N$_{a3}$AGCN$_{b1}$N$_{b2}$N$_{b3}$WCGAA-NNNNNN$_n$-3', N being any natural or artificial nucleotide including modified nucleotides, n symbolising a random number of nucleotides, W symbolising A or T, and Na1 being complementary to Nb1, Na2, to Nb2, and Na3 to Nb3. (SEQ ID NO: 22)

17E DNAzyme: A DNAzyme from the 8-17 family, consisting of the sequence; 5'-NNNNNN$_n$-TCCGAGCCGGTC-GAA-NNNNNN$_n$-3' (N being any natural or artificial nucleotide including modified nucleotides and n symbolising a random number of nucleotides). (SEQ ID NO: 23)

Cutting element: An element having endonuclease activity, enabling it to cleave a nucleic acid molecule. Examples of cutting elements includes DNAzymes and chemical groups such as a lanthanide(III) complex.

Open circular structure: A nucleic acid sequence which is in a circular structure, either aided by an external ligation template or self-templated, with at least one 5'-end and one 3'-end. This open circular structure may subsequently be turned into a closed circular structure by ligation.

Closed circular structure: A nucleic acid sequence with a non-ending backbone, e.g., but not limited to, sugar-phosphate in DNA and RNA, or N-(2-aminoethyl)-glycine units linked by peptide bonds in PNA.

Hybridise: Base pairing between two complementary nucleic acid sequences.

Probe: A nucleic acid sequence composed of natural or artificial, modified or unmodified nucleotides, having a length of e.g. 6-200 nucleotides.

Circle probe (also referred to as circular probe): A nucleic acid sequence used to form a probe with a non-ending backbone, thus it can be either in a closed circular structure or in an open circular structure. It has the ability to hybridise to a target nucleic acid sequence. Thus any feature and/or aspect discussed in regards circle probes may be applied by analogy to either to the closed circular structure or to the open circular structure or both.

Turtle probe: A class of circle probes, comprising a nucleic acid sequence with a free 3'-end and a free 5'-end. Turtle probes are able to both hybridise to a target sequence and provide their own ligation templates in the form of intramolecular structures, e.g. a hairpin structure. This self-provided ligation template allows ligation of the probe to form a closed circular structure.

Padlock probe: A class of circle probes, comprising a nucleic acid sequence with a free 3'-end and a free 5'-end, which upon hybridisation to its target will fold so that the 3'-end and the 5'-end are positioned next to each other, enabling ligation to form a closed circular structure.

Ligation template: A nucleic acid sequence to which the 5'-end and 3'-end of the same or a second nucleotide sequence can hybridise and be aligned in a way that enables ligation of the two ends to form a closed circular structure.

External ligation template: A nucleic acid sequence to which the 5'-end and 3'-end of a second nucleotide sequence can hybridise and be aligned in a way that enables ligation of the second nucleotide to form a closed circular structure.

Self-templated ligation: Ligation of the 5'-end and 3'-end of a nucleic acid sequence using a ligation template that is a part of said nucleic acid sequence.

Preformed circle probe: A class of circle probes, having a closed circular structure before it hybridises to its target sequence, and comprising a nucleic acid sequence capable of hybridising to a target sequence. This class of circle probes can preferably be obtained by ligation of a probe from the class of turtle probes, or, alternatively, by ligation of a probe from the class of padlock probes, using an external ligation template.

Intra-molecular structure: Hybridisation of one or more nucleic acid sequence parts in a molecule to one or more nucleic acid sequence parts of the same molecule.

Hairpin: A section of single-stranded nucleic acid sequence that hybridises onto itself, creating a single stranded nucleic acid loop and a double stranded nucleic acid region.

LNA: Locked nucleic acid.

PNA: Peptide nucleic acid.

Natural nucleic acids: The nucleotides G, C, A, T, U and I.

Artificial nucleic acid: That being both nucleic acids not found in nature, e.g., but not limited to, PNA, LNA, iso-dCTP, or iso-dGTP, as well as any modified nucleotide, e.g., but not limited to, biotin coupled nucleotides, fluorophore coupled nucleotides, or radioactive nucleotides.

Oligonucleotide: Here it is defined as a single stranded nucleic acid sequence, having a length of e.g. 10-200 nucleotides.

Capture oligonucleotide: A nucleic acid sequence directly or indirectly attached to a solid support and capable of capturing a target RNA molecule through hybridisation. It is to be understood that the capture oligonucleotide can be hybridised to the target nucleic acid either before or after attachment to a solid support, and that it may contain any natural or artificial nucleic acid.

Antibody: A protein of the immunoglobulin family that recognises a specific antigen and binds it selectively. This includes also fragments of an antibody, e.g., but not limited to, a FAB fragment.

Receptor and marker molecules: A pair of molecules, such as biotin/streptavidine, capable of 1) binding selectively to each other and 2) being attached to a solid surface or a biomolecule. The attachment may be direct or indirect, e.g. through protein A.

Solid support: Any solid surface an oligonucleotide or the receptor/marker pair can be attached to or synthesised on, that being, e.g., but not limited to, microscope slides, ELISA-plates, microchips or beads.

Target RNA molecule: An RNA molecule with which a probe is designed to hybridise.

Target nucleic acid molecule: A nucleic acid molecule with which the probe is designed to hybridise.

Target sequence: A sequence in the target nucleic acid molecule with which the probe can hybridise.

Biotin coupled oligonucleotide: An oligonucleotide with a biotin bound to its 3' end, 5' end, or somewhere within the oligonucleotide.

Rolling circle template: A closed circular sequence of nucleotides, artificial or natural, that the polymerase uses as a template during rolling circle replication.

Rolling circle replication: DNA synthesis using a circular single stranded oligonucleotide as rolling circle template and a target RNA molecule or a target DNA molecule as primer. The addition of a DNA polymerase and dNTPs starts the polymerization. As the rolling circle template is endless, the product will be a long single stranded DNA strand composed of tandem repeats complementary to the rolling circle template. Artificial as well as natural nucleic acid residues can serve as substrates for the rolling circle replication.

Nick: A nick is to be understood as a break in one strand of a double-stranded nucleic acid, caused by a missing phosphodiester bond, that leave a free 3'-hydroxyl group and a 5'-phosphate group. The bases adjacent to the nick will still be hybridised to bases on the opposite strand. A nick is for example the result of digestion by a nicking endonuclease. A nick may also be the result of hybridising two sequences on a ligation template, such that the 5'-end of one sequence is adjacent to the 3'end of the other sequence. A nick can be ligated by the action of a ligase.

DETAILED DESCRIPTION OF THE INVENTION

The present invention concerns new circle probe designs and their method of use in detection of single nucleic acid molecules by rolling circle replication. The methods and probes mentioned below can be used for in vitro diagnostics and in diagnostic kits.

In one embodiment, the invention relates to a new circle probe design, the turtle probe:

A circular nucleic acid probe further comprising:
i) A first part and a third part comprising nucleic acid sequences that are at least 75% complementary
ii) A second nucleic acid part comprising a hairpin structure extending either from said first part or from said third part Such as but not limited to circular nucleic acid probe with a total length of 30-200 nucleotides comprising:
i) A first part and a third part comprising nucleic acid sequences that are at least 75% complementary to each other and each having a length of 3-100 nucleotides
ii) A second nucleic acid part comprising a hairpin structure extending either from said first part or from said third part and wherein said second part has a length of 9-50 nucleotides
iii) A fourth part comprising a sequence of nucleic acid residues, which is at least 75% complementary to a target nucleic acid sequence and wherein the length of said fourth part is 6-100 nucleotides.

In one embodiment the present invention may also be described as a circular nucleic acid probe, wherein the 3'-end and the 5-end is brought into proximity by a intermolecular structure in the probe, such that the 3'-end and the 5-end are separated by a nick.

The probe may in a particular preferred embodiment be single stranded. And in a particular preferred embodiment said probe is a DNA probe.

A turtle probe is characterised by containing its own ligation template in the sequence of the probe, allowing ligation of the probe to form a closed circular structure by self-templated ligation without the addition of an external ligation template.

The purpose and characteristics of the turtle probe are outlined below in detail.

Complementarities

The self-templated ligation is possible due to intramolecular hybridisation of the turtle probe, mediated through a hairpin structure and two complementary sequences comprised within its sequence. When these complementary sequences hybridise in proximity of the hairpin the 5'-end and the 3'-end of the probe are brought in proximity enabling ligation of the probe to form a closed circular structure. Thus, in one embodiment, the invention relates to a circular nucleic acid probe comprising, a first part and a third part comprising nucleic acid sequences that are at least 75% complementary and a second nucleic acid part comprising a hairpin structure extending either from said first part or from said third part, such as e.g. 75-100% complementary, or such as e.g. 80-100% complementary, or such as e.g. 85-100% complementary, or such as e.g. 90-100% complementary, or such as e.g. 95-100% complementary, or such as e.g. 100% complementary. It is to be understood that the complementary parts are able to hybridise to each other.

Self-templated ligation may be preferable when the ligation efficiency on the target nucleic acid molecule is low (e.g.

on RNA targets or on DNA targets containing modifications resulting from degradation, preparation, or fixation, such as addition of mono-methylol (—CH$_2$OH) groups to the bases of the nucleic acids, resulting in dimerisation of adenine groups by methylene bridging). Procedures to revert such base-modification have been published (Masuda N. et al. Nucleic Acids Res. 15; 27(22) 4436-43 (1999)), but they only reduce the damage, since complete removal of all modifications is not possible. Another advantage of the turtle probe is that the self-contained ligation template is a stretch of naked DNA which, compared to externally templated ligation using e.g. chromatin DNA, should result in higher ligation efficiency. Thus, in a second embodiment, the invention relates to a nucleic acid probe further comprising a fourth part comprising a sequence of nucleic acid residues, which is at least 75% complementary to a target nucleic acid sequence, such as e.g. 75-100% complementary, or such as e.g. 80-100% complementary, or such as e.g. 85-100% complementary, 90-100% complementary, or such as e.g. 95-100% complementary, or such as e.g. 100% complementary.

Turtle probes can detect individual non-polyadenylated RNA's, such as, but not limited to, EBER1 and EBER2 from the Epstein-Barr virus, the adenovirus-encoded small RNA's VA1 and VA2, ribosomal RNA's, the RNA part of the telomerase complex (hTERC), small interfering RNA's (siRNA's), and micro-RNA's (miRNA's).

On RNA targets, a preferred embodiment of the invention relates to a circular nucleic acid probe comprising a fourth part of nucleic acid residues, wherein said fourth part comprises a sequence of nucleic acid residues, which is at least 75% complementary to a target RNA sequence, such as e.g. 75-100% complementary, or such as e.g. 80-100% complementary, or such as e.g. 85-100% complementary, 90-100% complementary, or such as e.g. 95-100% complementary, or such as e.g. 100% complementary.

The fourth part of the turtle probe, comprising a nucleic acid sequence complementary to a target nucleic acid sequence, can have a linear length of 6-100. Thus, in one embodiment, the invention refers to a circular nucleic acid probe, wherein the length of said fourth part is 6-100 nucleotides, such as e.g. 20-100 nucleotides, or such as e.g. 20-80 nucleotides, or such as e.g. 20-60 nucleotides, or such as e.g. 20-40 nucleotides, or such as e.g. 20-30 nucleotides.

The first and third parts of the turtle probe comprise complementary sequences which, upon hybridisation to each other, are able to (together with the second part) fold the probe into an open circle structure, which can be ligated into a closed circular structure (FIG. 1D). The length of these parts needs to be of a size which allows hybridisation under the reaction conditions. Thus, in one embodiment, the invention refers to a circular nucleic acid probe, wherein the length of said first part and third part each is 3-100 nucleotides, such as e.g. 3-50 nucleotides, or such as e.g. 3-40 nucleotides, or such as e.g. 3-30 nucleotides, or such as e.g. 3-20 nucleotides, or such as e.g. 3-10 nucleotides.

The second part of the turtle probe, comprising a hairpin, is important for turning the probe into an open circle upon intra-molecular hybridisation. The length of this part needs to be of a size which allows hybridisation under the reaction conditions. Thus, in one embodiment, the invention refers to a circular nucleic acid probe, wherein the length of said second part is 9-50 nucleotides, such as e.g. 15-50 nucleotides, or such as e.g. 15-40 nucleotides, or such as e.g. 15-30 nucleotides, or such as e.g. 10-20 nucleotides, or such as e.g. 15-20 nucleotides.

In order to identify a turtle probe, or distinguish between different turtle probes, if more than one turtle probe is present in a reaction, an element defining the particular turtle probe, an identifier, is required. Thus, in one embodiment, the invention relates to a circular nucleic acid probe, further comprising one or more elements defining the specific probe.

In a presently preferred embodiment, the invention relates to a circular nucleic acid probe with a total length of total length of the probe is 30-200 nucleotides comprising:
1. A first part and a third part comprising nucleic acid sequences that are at least 75% complementary to each other and each have a length of 3-100 nucleotides
2. A second nucleic acid part comprising a hairpin structure extending either from said first part or from said third part and wherein said second part has a length of 9-50 nucleotides
3. A fourth part comprising a sequence of nucleic acid residues, which is at least 75% complementary to a target nucleic acid sequence and wherein the length of said fourth part is 6-100 nucleotides.

Different methods can be used to identify a specific turtle probe, and depending on the choice of method, the identifier element will differ.

If detection is obtained through hybridisation of labelled oligonucleotides to identifier elements, the identifiers need to have a certain length to be specific to a target sequence and to allow hybridisation under the reaction conditions. In theory an identifier could match the total length of the probe, but in most cases a shorter identifier element would be preferable. Shorter identifiers would have faster hybridisation kinetics and would enable a probe to contain more than one identifier. Thus, in one embodiment, the invention relates to an element defining the specific probe, which is a nucleotide sequence of 6-200 nucleotides, such as e.g. 6-150 nucleotides, or such as e.g. 6-100 nucleotides, or such as e.g. 6-80 nucleotides, or such as e.g. 6-60 nucleotides, or such as e.g. 6-50 nucleotides, or such as e.g. 10-40 nucleotides, or such as e.g. 10-30 nucleotides, or such as e.g. 15-30 nucleotides.

However, since the turtle probes are used as templates in rolling circle replications, detection can also be obtained through synthesis. Such detection through synthesis could be performed similar to established linear PRINS reactions. Whereas incorporation of a labelled (e.g. a fluorophore) A, T, G, C, or U is an obvious approach, it will give rise to background staining, as these nucleotides could be incorporated not only in the rolling circle replication product but also elsewhere in the sample. Incorporating one or more artificial nucleotides, such as isoC or isoG, into the sequence of the probe and providing the complementary nucleotide as a labelled nucleotide (e.g. a fluorophore) during replication may therefore be preferable. Since such artificial nucleotides are not found in nature, iso-dCTP and iso-dGTP will not be incorporated elsewhere in the sample, minimizing background reactions. This aspect makes the use of a fluorophore-coupled iso-dCTP nucleotides or iso-dGTP nucleotides preferable. If detection is obtained through synthesis, the identifier element, defining the specific probe, may therefore preferably be one or more artificial nucleotide. Thus, in another embodiment, the invention relates to an element defining the specific probe, which is composed of one or more artificial nucleotides, such as e.g. 1-20 artificial nucleotides, or such as e.g. 1-10 artificial nucleotides, or such as e.g. 1-5 artificial nucleotides, or such as e.g. 4 artificial nucleotides, or such as e.g. 3 artificial nucleotides, or such as e.g. 2 artificial nucleotides, or such as e.g. 1 artificial nucleotide.

The total length of the turtle probe may vary depending on the specific length of each element defined above. Furthermore, currently there is a limitation on the length of chemical synthesized oligonucleotides at around 150-200 nucleotides.

It can also be an advantage to use a probe which is as short as possible (without compromising the hybridization events and the rolling circle efficiency dramatically), since the shorter the circle, the more times the identifier element will be copied per unit length of DNA synthesized, increasing the detection signal at the end of the reaction. Thus, in one embodiment, the invention refers to a circular nucleic acid probe, wherein the total length of the probe is 30-200 nucleotides, such as e.g. 30-150 nucleotides, or such as e.g. 50-150 nucleotides, or such as e.g. 70-150 nucleotides, or such as e.g. 90-150 nucleotides, or such as e.g. 70-130 nucleotides, or such as e.g. 70-110 nucleotides.

Thus, in one embodiment, the invention relates to a turtle probe comprising the sequence (SEQ ID NO:1):

```
5'-P-GTCGATCCCCTCAATGCACATGTTTGGCTCCAAAACATGCGGAC-
CACCAGCTGGTACTTGACCGGATCGACTCGGAATAACCGA-3'
wherein P is a 5'-phosphate
```

Thus, in another embodiment, the invention relates to a turtle probe comprising the sequence (SEQ ID NO:2):

```
5'-P-GTCGATCCCCTCAATGCACATGTTTGGCTCCAAAAATAGCGGACA
AGCCGAATA-CCCTTCTCCCGGATCGACTCGGAATAACCGA-3'
wherein P is a 5'-phosphate
```

Thus, in another embodiment, the invention relates to a turtle probe comprising the sequence (SEQ ID NO:3):

```
5'-P-GTCGATCCCCTCAATGCTGCTGCTGTACTACAAAACATGCGGACC
ACCAGC-TGGTACTTGACCGGATCGACTCGGAATAACCGA-3'
wherein P is a 5'-phosphate
```

Thus, in another embodiment, the invention relates to a turtle probe comprising the sequence (SEQ ID NO:4):

```
5'-P-GTCGATCCCCTCAATGCTGCTGCTGTACTACAAAAATAGCGGACA
AGCC-GAATACCCTTCTCCCGGATCGACTCGGAATAACCGA-3'
wherein P is a 5'-phosphate
```

Thus in another embodiment, the invention relates to a turtle probe comprising the sequence (SEQ ID NO:5):

```
5'-P-GTCGATCCCCTCAATGCTGCTGCTGTACTACGCATGTGTGAGCCG
AGTCC-TGGGTGCACGTCCCACAGCTCGGATCGACTCGGAATAACCGA-
3'
wherein P is a 5'-phosphate
```

When using target primed rolling circle replication for the detection of target nucleic acid molecules, a 3'-end has to be present close to where the probes hybridise, to serve as a primer for the rolling circle replication. When detecting DNA, this 3'-end can either be present due to biological processes or preparation artefacts (WO 97/20948) or it can be created subsequently, e.g. using restriction enzymes (WO 99/49079 and in Larsson C. et al. Nature Methods 1, 227-32 (2004)).

However, restriction enzymes cannot be used if the target molecule is RNA and since preparation artefacts will be very different among preparations, a more specific generation of 3'-ends would be preferred. Some RNA molecules have a usable 3'-end close to the region where the probe hybridises, and in this case a probe without cutting elements can be used. However this requirement for a 3'-end limits the position of the probe to the vicinity of the 3'-end of the RNA molecules.

This problem is solved by the introduction of the slicer probe, which is a circular probe with a cutting element incorporated. This cutting element enables the slicer probe to cleave a target nucleic acid, producing a new 3'-end where it hybridises. Consequently, it is possible to target any accessible region of any nucleic acid molecule, enabling the detection of e.g. eukaryotic messenger RNA, which is polyadenylated at the 3'-end.

RNA splicing is a strictly regulated process where a pre-mRNA (pre-messenger RNA), which is a precise copy of the coding sequence of the gene comprising alternating exons and introns, has the introns removed to produce a sequence of exons, which are then translated into a protein. Exons can also be omitted from the final mRNA during splicing. This is a common phenomenon called alternative splicing, which allows one gene to give rise to several different mRNA's, and thereby to several different proteins. It provides a way of regulating the activity of proteins or producing proteins with different activities from the same gene. However, if the alternative splicing is not correctly regulated, it can have serious consequences, and alternative splicing has been found to play a significant role in the development of many human diseases e.g. cancer.

Detection of eukaryotic messenger RNA, e.g. splice variants, may be performed by positioning the cutting element inside the target-complementary part of the slicer probe, dividing the target-complementary part into two parts. If these two parts are designed to recognise part of two neighbouring exons, e.g. exon 2 and 1 respectively, the slicer probe hybridises at the exon 1-2 junction. A signal would then only occur if an exon 1-2 junction is present allowing the slicer probe to hybridise and cleave the target RNA. If a splice variant without exon 2, but with an exon 1-3 junction, is present, it could be detected, simultaneously, by adding a different slicer probe wherein the two target-complementary parts recognise an exon 1-3 junction. Thus, different splice variants can be detected using the slicer probes of the invention. Similarly, exon-intron junctions can be detected having a slicer probe comprising a target-complementary part spanning an exon-intron junction. Since multiple probes can be co-hybridised, each having it own identifier, screening for several splice variants simultaneously is achievable.

Examples of cancer-related genes that exhibit alternative splicing, which could be detected with slicer probes, include, but are not limited to, CD44, WT1, BRCA1, BRCA2, MDM2, FGFR 1-4, kallinkrin family members, NRSF, NF1, SVH, SRF, FYN, Caspase-8, PASG, MUC1, Insulin receptor, Rac1, KAI1/CD82, WISP1, Secretin receptor, Gastrin receptor, DNMT3b4, SVH, C-CAM, VEGF, Actinin-4, SHBG, Integrin __1C, AIB1, Androgen receptor, Estrogen receptor, Syk, uPAR, FGFR1, Crk, NF1, TSG101, Tenascin-C, Fibronectin, Ikaros, RET, HE4/WFDC2, Bradeion, SSCA/SERPINB3, TADG-12/TMPRSS3, Testisin, PSCA, Bin-1, Bim/BCL2L11, Fas antigen/CD95, Aggrecan, TACC, RSU-1, Tyrosine hydroxylase, RON, Tenascin, Fibulin-1, hSlo, Thyroid hormone receptor, FGF-8, CEACAM1/CD66a/BGP, and WWOX (Brinkman B M, Clin Biochem. 37(7), 584-94 (2004) and Venables J P, Cancer Res. 64(21), 7647-54 (2004)), Osteopontin, Survivin, hTERT (telomerase), Cyclin D1, or Insulin receptor.

Several nucleic acid enzymes have been described in the literature as capable of cleaving nucleic acid sequences. These nucleic acid enzymes can be both deoxyribozymes and ribozymes, and both types would be able to provide the activity required as cutting element. Thus, in one embodiment, the invention relates to a slicer probe, wherein said element having endonuclease activity is a nucleic acid sequence. However, since DNA is more stable than RNA, and the preferred polymerases used are DNA polymerases, deoxyribozymes are preferred as cutting elements. Thus, in another embodiment, the invention relates to a slicer probe, wherein said element having endonuclease activity is a DNA sequence. Many different catalytic nucleic acids composed entirely of DNA have in recent years been generated by in vitro selection strategies, and have been named deoxyribozymes (DNAzymes). DNAzymes comprising endonuclease activity mediate sequence specific cleavage and are therefore ideal as cutting elements. Thus in another embodiment the invention relates to a slicer probe, wherein said element having endonuclease activity is a DNAzyme.

Most DNAzymes described exhibit ribonuclease activity, and the currently most interesting DNAzymes, for cleavage of RNA, are the 10-23, 8-17, 17E (a derivative of the 8-17 enzyme) and the 16.2-11.

The 10-23 DNAzyme, so-called because it was the 23rd clone of the 10th cycle of in vitro selection, comprises a divalent metal ion-dependent catalytic domain composed of 15 nucleotides, flanked by two substrate recognition arms that bind to target RNA through Watson-Crick base-pairing. The 10-23 DNAzyme has been reported to function with several different divalent metal ions as co-factor. The 10-23 DNAzyme cleaves a specific phosphodiester linkage between an unpaired purine, A/G, and a paired pyrimidine, U(/C), producing a 2',3'-cyclic phosphate terminus, and a 5'-hydroxyl terminus (Santoro S W and Joyce G F Proc Natl Acad Sci USA. 29; 94(9):4262-6. (1997)). Thus in another embodiment, the invention relates to a slicer probe, wherein said element having endonuclease activity is the 10-23 DNAzyme The 8-17 DNAzyme, so-called because it was the 17th clone from round 8 of in vitro selection, comprises a divalent metal ion-dependent catalytic domain composed of 13 nucleotides, flanked by two substrate recognition arms that bind to target RNA through Watson-Crick base-pairing (Santoro S W and Joyce G F Proc Natl Acad Sci USA. 29; 94(9):4262-6. (1997)).

The 8-17 DNAzyme has, like the 10-23 DNAzyme, been reported to function with several different divalent metal ions as co-factor. The 8-17 DNAzyme cleaves a specific phosphodiester linkage between a T wobbled-paired to G followed by any ribonucleotide (A, C, G or U), producing a 2',3'-cyclic phosphate terminus and a 5'-hydroxyl terminus. Thus in another embodiment the invention relates to a slicer probe, wherein said element having endonuclease activity is a DNAzyme from the 8-17 family.

Generally, RNA-cleaving DNAzymes are ideal as cutting elements, as they are easily incorporated into the sequence of the probe, creating a slicer probe. However when using such a design the slicer probe will, upon cleavage of the target RNA molecule, produce a 5'-hydroyl terminus and a 2',3'-cyclic phosphate terminus, wherein the 2',3'-cyclic phosphate terminus, has a one nucleotide overhang to the slicer probe. Normally a one base nucleotide overhang is easily removed before onset of a rolling circle replication by a polymerase comprising exonuclease activity. However, since a 2',3'-cyclic phosphate efficiently inhibits the exonuclease and polymerase activity of at least some DNA polymerases (e.g. the Phi29 DNA polymerase), modification/removal of such a 2',3'-cyclic phosphate is required to allow the 3'-end to prime a rolling circle reaction. Removal of the 2',3'-cyclic phosphate can be done enzymatically, using the T4 polynucleotide kinase, which produces the 3'-hydroxyl termini needed to prime the rolling circle reaction. The 8-17 DNAzyme has been subjected to additional rounds of in vitro selection, which has resulted in new variants of this DNAzyme. Among these, the 17E DNAzyme is the most interesting, since it has been reported to comprise a two step mechanism in which the 2',3'-cyclic phosphate normally produced by DNAzyme cleavage is hydrolysed. This hydrolysis of the 2',3'-cyclic phosphate only occurs when $Pb^{2+}$ is used as the divalent metal co-factor. However, if the 17E DNAzyme is used as cutting element with $Pb^{2+}$ as co-factor, the cleavage product is a 3'-(or 2'-) monophosphate terminus and a 5'-hydroxyl terminus (Brown A K et al. Biochemistry 17; 42(23):7152-61 (2003)). This may allow the new 3'-end to act as primer for rolling circle replication, without the requirement for modification/removal, if a DNA polymerase comprising exonuclease activity is used. Thus, in another embodiment, the invention relates to a slicer probe, wherein said element having endonuclease activity is the 17E DNAzyme.

DNAzymes comprising deoxyribonuclease activity have also been described, but due to the greater stability of DNA, such DNAzymes must likely comprise a more complex active site. Efficient DNAzymes, comprising deoxyribonuclease activity, must therefore be rarer than DNAzymes comprising ribonuclease activity. DNAzymes, comprising deoxyribonuclease activity, have been divided into two classes; class I, which requires both $Cu^{2+}$ and ascorbate to promote DNA cleavage, and class II, which only requires $Cu^{2+}$ (Carmi N. et al. Proc Natl Acad Sci USA. 3; 95(5):2233-7 (1998)). Currently, DNAzymes are less efficient for DNA cleavage than for RNA cleavage, but in the future DNAzymes with higher cleavage efficiencies on DNA will most likely be developed.

Some deoxyribozymes contain intramolecular base paring, e.g. the 8-17 DNAzyme. Such structures could be strengthened by incorporation of artificial nucleotides, e.g. PNA or LNA, both known to improve the hybridisation efficiency, which may improve the cleavage efficiency.

In the literature, different reactive chemical groups coupled to oligonucleotides have been reported capable of inducing sequence specific cleavage of nucleic acid molecules. Many of these chemical groups utilise divalent metal ions as cofactor similar to the DNAzymes. The oligonucleotide, coupled to the chemical complex, hybridises to a sequence in the target nucleic acid molecule thereby determining the cleavage site through its sequence. If this coupled oligonucleotide is part of a slicer probe, the slicer probe provides the target specificity, through hybridisation of the probe to the target nucleic acid molecule, and the chemical group cleaves the target nucleic acid molecule producing a 3'-end used as primer for the rolling circle reaction. In case the chemical complex inhibits the rolling circle replication, the complex could be released from the slicer probe before rolling circle replication, if the chemical group is coupled to the probe through a cleavage linker, e.g., but not limited to, a disulfide bridge. Thus, in another embodiment, the invention relates to a slicer probe, wherein said element having endonuclease activity is a reactive chemical group.

As with the DNAzymes, reactive chemical groups have been described comprising ribonuclease activity, and some of these groups have been coupled to oligonucleotides to provide sequence specificity, e.g., but not limited to, Terpyridine-Cu(II) (Sakamoto S. et al. Nucleic Acids Res. 1; 31(5):1416-25 (2003)), 5-amino-2,9-dimethylphenanthroline-Zn(II) (Astrom H. et al. Org Biomol Chem. 7; 1(9):1461-5 (2003)), Tetraazamacrocycles-Eu(III) (Huang L. et al. J Biol Inorg Chem. 5(1):85-92 (2000)), and Neocuproine-Zn(II) (Whitney A. et al. Chem Commun (Camb). 7; (1):36-7 (2003)), which all have been reported to induce sequence specific cleavage directed by the coupled oligonucleotide. In the case of Neocuproine-Zn(II), the oligonucleotide comprised artificial nucleotides in the form of PNA, which were used due to the increased target affinity, sequence specificity, and biochemical stability. Thus, in another embodiment, the invention relates to a slicer probe, wherein said element having endonuclease activity is selected from the group consisting of: Terpyridine-Cu(II), 5-amino-2,9-dimethylphenanthroline-Zn(II), Tetraazamacrocycles-Eu(III), and Neocuproine-Zn(II).

Despite the greater stability of DNA, compared to RNA, reactive chemical groups comprising deoxyribonuclease activity have also been reported, e.g., but not limited to, Ciprofloxacin (HCp) with $Cu^{2+}$ as co-factor. HCp can act as an efficient chemical nuclease with $Cu^{2+}$ as co-factor upon ascorbate/hydrogen peroxide activation (Jimenez-Garrido N et al. J Inorg Biochem. 99(3):677-89 (2005)). As with the DNAzymes, reactive chemical groups are currently less efficient for DNA cleavage than for RNA cleavage, but reactive chemical groups with higher cleavage efficiencies on DNA will most likely be developed in the future.

Reactive chemical groups have been reported both as coupled to one end of the oligonucleotide hybridising to the target nucleic acid molecule and as coupled to the nucleic acid molecule inside the hybridising region, whereas the DNAzymes have to be positioned inside the hybridising region. Thus, in one embodiment, the invention relates to a slicer probe, wherein the one or more elements having endonuclease activity is positioned internally in the target complementary sequence, dividing it into two or more parts, and in another embodiment, the invention relates to a slicer probe, wherein said element having endonuclease activity is a reactive chemical group positioned in one end of the target complementary region.

In order to identify a slicer probe, or distinguish between different slicer probes, if more than one slicer probe are present in a reaction, one or more elements defining the particular slicer probe, an identifier, is required. Thus, in one embodiment, the invention relates to a circular nucleic acid probe, further comprising one or more elements defining the specific probe.

Different methods can be used to identify a specific slicer probe, and the identifier element will differ depending on the choice of method.

If detection is obtained through hybridisation of a labelled oligonucleotide to the identifier elements, the identifiers need to have a certain length to be specific to a target sequence and allow hybridization under the reaction conditions. In theory an identifier could match the total length of the probe, but in most cases a shorter identifier element would be preferable. Shorter identifiers would have faster hybridisation kinetics and would enable a probe to contain more than one identifier. Thus, in one embodiment, the invention relates to an element defining the specific probe, which is a nucleotide sequence of 6-200 nucleotides, such as e.g. 6-150 nucleotides, or such as e.g. 6-100 nucleotides, or such as e.g. 6-80 nucleotides, or such as e.g. 6-60 nucleotides, or such as e.g. 6-50 nucleotides, or such as e.g. 10-40 nucleotides, or such as e.g. 10-30 nucleotides, or such as e.g. 15-30 nucleotides.

However, since the slicer-turtle probes are used as templates in rolling circle replications, detection can also be obtained through synthesis. Such detection through synthesis could be performed similar to established linear PRINS reactions. Whereas incorporation of a labelled (e.g. a fluorophore) A, T, G, C, or U is an obvious approach, it will give rise to background staining, as these nucleotides could be incorporated not only in the rolling circle replication product but also elsewhere in the sample. Incorporating one or more artificial nucleotides, such as isoC or isoG, into the sequence of the probe and providing the complementary nucleotide as a labelled nucleotide (e.g. a fluorophore) during replication may therefore be preferable. Since such artificial nucleotides are not found in nature, they will not be incorporated to any great extent elsewhere in the sample, minimizing background reactions. This aspect makes the use of a fluorophore-coupled iso-dCTP nucleotides or iso-dGTP nucleotides preferable. If detection is obtained through synthesis, the identifier element, defining the specific probe, may therefore preferably be one or more artificial nucleotide. Thus, in another embodiment, the invention relates to an element defining the specific probe, which is composed of one or more artificial nucleotides, such as e.g. 1-20 artificial nucleotides, or such as e.g. 1-10 artificial nucleotides, or such as e.g. 1-5 artificial nucleotides, or such as e.g. 4 artificial nucleotides, or such as e.g. 3 artificial nucleotides, or such as e.g. 2 artificial nucleotides, or such as e.g. 1 artificial nucleotide.

The total length of the slicer-turtle probe can vary depending on the specific length of each element defined above. Furthermore, at the moment there is a limitation on the length of chemical synthesized oligonucleotides at around 150-200 nucleotides. It can also be an advantage to use a probe which is as short as possible (without compromising the hybridization events and the rolling circle efficiency dramatically), since the shorter the circle, the more times the identifier element will be copied per unit length of DNA synthesized, increasing the detection signal at the end of the reaction. Thus, in one embodiment, the method refers to a circular nucleic acid probe, wherein the total length of the probe is 30-200 nucleotides, such as e.g. 30-150 nucleotides, or such as e.g. 50-150 nucleotides, or such as e.g. 70-150 nucleotides, or such as e.g. 90-150 nucleotides, or such as e.g. 70-130 nucleotides, or such as e.g. 70-110 nucleotides.

The preferred slicer probe design is the slicer-turtle, since it can be ligated by self-templated ligation, which in particular may be preferable when the ligation efficiency on the target nucleic acid molecule is low (e.g. on RNA targets or on DNA targets containing modifications resulting from the preparation or fixation, such as e.g. addition of mono-methylol (—CH$_2$OH) groups to the bases of the nucleic acids, resulting in dimerisation of adenine groups by methylene bridging). Thus, in a preferred embodiment, the invention relates to a circular nucleic acid probe of the slicer-turtle probe class, wherein said probe comprises one or more elements having endonuclease activity.

A slicer-turtle probe is characterised by comprising one ore more cutting elements, and by containing its own ligation template in the sequence of the probe, allowing ligation of the probe to form a closed circular structure without addition of an external ligation template. Thus in a preferred design, the slicer-turtle probe comprises (FIG. 6H):

A circular nucleic acid probe comprising:
  I. A first part and a third part comprising nucleic acid sequences that are at least 75% complementary to each other and each have a length of 3-100 nucleotides
  II. A second nucleic acid part comprising a hairpin structure extending either from said first part or from said third part and wherein said second part has a length of 9-50 nucleotides
  III. A fourth part comprising a sequence of nucleic acid residues, which is at least 75% complementary to a target nucleic acid sequence and wherein the length of said fourth part is 6-100 nucleotides

IV. A cutting element

The self-templated ligation is possible due to intramolecular hybridisation of the slicer-turtle probe, mediated through a hairpin structure and two complementary sequences comprised within its sequence. When these complementary sequences hybridise, the 5'-end and the 3'-end of the slicer-turtle probe are brought in proximity, enabling ligation of the probe to form a closed circular structure. Thus, in one embodiment, the invention relates to a nucleic acid probe comprising, a first part and a third part comprising nucleic acid sequences that are at least 75% complementary, and a second nucleic acid part comprising a hairpin structure extending either from said first part or from said third part, and a cutting element, such as e.g. 75-100% complementary, or such as e.g. 80-100% complementary, or such as e.g. 85-100% complementary, 90-100% complementary, or such as e.g. 95-100% complementary, or such as e.g. 100% complementary, It is to be understood that the complementary parts are able to hybridise to each other.

A slicer-turtle probe can contain one or more cutting elements and a cutting element can be positioned inside the hybridising region or in one end of the hybridising region (if the cutting element is a reactive chemical group). Therefore, the part of the slicer-turtle probe hybridising to the target nucleic acid molecule, may be divided into two or more hybridising parts. Thus, in one embodiment, the invention relates to a slicer-turtle probe, wherein the one or more elements having endonuclease activity is positioned internally in the target complementary sequence, dividing it into two or more parts, and in another embodiment, the invention relates to a slicer-turtle probe, wherein said element having endonuclease activity is a reactive chemical group positioned in one end of the target complementary region.

However, in a preferred embodiment, one cutting element is used, which is positioned inside the hybridising part, dividing it into two parts. Thus, in another embodiment, the invention relates to a nucleic acid probe of the slicer-turtle class, further comprising a fourth and a fifth part each comprising a sequence of nucleic acid residues, which is at least 75% complementary to a target nucleic acid sequence, such as e.g. 75-100% complementary, or such as e.g. 80-100% complementary, or such as e.g. 85-100% complementary, or such as e.g. 90-100% complementary, or such as e.g. 95-100% complementary, or such as e.g. 100% complementary. On RNA, this preferred embodiment of the invention relates to a circular nucleic acid probe of the slicer-turtle class, comprising a fourth and a fifth part of nucleic acid residues, wherein said fourth and fifth part each comprises a sequence of nucleic acid residues, which is at least 75% complementary to a target RNA sequence.

The fourth and fifth part of the slicer-turtle may have the same or different lengths, as long as both are capable of hybridising to the target nucleic acid molecule under the reaction conditions. The fourth part of the slicer-turtle probe, comprising a nucleic acid sequence complementary to a target nucleic acid sequence, may have a linear length of 6-100 nucleotides. Thus, in one embodiment, the invention relates to a circular nucleic acid probe of the slicer-turtle class, wherein the length of said fourth part is 6-100 nucleotides, such as e.g. 10-100 nucleotides, or such as e.g. 10-80 nucleotides, or such as e.g. 10-60 nucleotides, or such as e.g. 10-40 nucleotides, or such as e.g. 10-30 nucleotides. The fifth part of the slicer-turtle probe, comprising a nucleic acid sequence complementary to a target nucleic acid sequence, may have a linear length of 6-100. Thus, in one embodiment, the invention relates to a circular nucleic acid probe of the slicer-turtle class, wherein the length of said fifth part is 6-100 nucleotides, such as e.g. 10-100 nucleotides, or such as e.g. 10-80 nucleotides, such as e.g. 10-60 nucleotides, or such as e.g. 10-40 nucleotides, or such as e.g. 10-30 nucleotides.

The first and third part of the slicer-turtle probe comprise complementary sequences which, upon hybridisation to each other, are able to (together with the second part) fold the probe into an open circular structure, which can be ligated into a closed circular structure (FIG. 1H). The length of these parts needs to be of a size which allows hybridisation under the reaction conditions. Thus, in one embodiment, the invention relates to a circular nucleic acid probe of the slicer-turtle class, wherein the length of said first part and third part each is 3-100 nucleotides, such as e.g. 3-50 nucleotides, or such as e.g. 3-40 nucleotides, 3-30 nucleotides, or such as e.g. 3-20 nucleotides, or such as e.g. 3-10 nucleotides.

The second part of the slicer-turtle probe, comprises a hairpin, which is important for turning the probe into an open circular structure upon intra-molecular hybridisation. The length of this part needs to be of a size which allows hybridisation under the reaction conditions. Thus, in one embodiment, the invention relates to a circular nucleic acid probe of the slicer-turtle class, wherein the length of said second part is 9-50 nucleotides, such as e.g. 15-50 nucleotides, or such as e.g. 15-40 nucleotides, 15-30 nucleotides, or such as e.g. 10-20 nucleotides, or such as e.g. 15-20 nucleotides.

Thus in one embodiment, the invention relates to a slicer-turtle comprising the sequence (SEQ ID NO:6):

```
5'-P-
GTCGATCCCCTCAATGCTGCTGCTGTACTACGCTACAGCCACACAGGCTA
GCTACAACGAGT CTCCTCCCTAGCAAAACCGGATCGACTCGGAATAACC
GA-3'
```
wherein P is a 5'-phosphate Thus in another embodiment, the invention relates to a slicer-turtle comprising the sequence (SEQ ID NO:7):

```
5'-P-
GTCGATCCCCTCAATGCACATGTTTGGCTCCTCGGTAGCACCGCAGGCTA
GCTACAACGATG AGCGTTGGCGGTGTGTCCGGATCGACTCGGAATAACC
GA-3'
```
wherein P is a 5'-phosphate Both padlock probes and preformed circle probes can likewise be turned into slicer probes (slicer-padlocks and preformed slicer-circles respectively), by introduction of one or more cutting elements into the circle probe. Thus, in another embodiment, the invention relates to a circular nucleic acid probe, which is a preformed circle probe or a padlock probe, wherein said probe comprises one or more elements having endonuclease activity. Thus, in one embodiment, the invention relates to a slicer probe which is a circular nucleic acid probe, comprising:

i) One or more parts, each part comprising a sequence of nucleic acid residues which is at least 75% complementary to a region of the target nucleic acid sequence, and ii) an element defining the specific probe In this embodiment, the invention may further relate to a slicer probe, wherein the total length, of the one or more parts comprising at least 75% complementary to a region of the target nucleic acid sequence, is 6-100 nucleotides.

A preformed slicer-circle is characterised by comprising one or more target recognising parts, one or more cutting elements (as slicer probes in general), and by being in a closed circular structure prior to its use as a hybridisation probe. These types of slicer probes can preferably be obtained by ligation of a slicer-turtle prior to use. Slicer-turtle probes are ideal for the creation of preformed slicer-circle probes since they are self-templated, and therefore can be ligated to form a closed circular structure without an external ligation template. An external ligation template would have to be removed from the preformed slicer-circle probe prior to hybridisation to ensure that the external ligation template is not used as rolling circle primer resulting in false signals. Since slicer-probes provide single molecule detection, this removal would have to be absolutely complete, which may be hard to achieve in practice.

Thus in a preferred design the preformed slicer-circle probe comprises:
  i) One or more parts, each part comprising a sequence of nucleic acid residues which is at least 75% complementary to a region of the target nucleic acid sequence, and
  ii) an element defining the specific probe, and
  iii) one or more cutting elements, and
  iv) a closed circular structure i.e. a non-ending backbone.

A preformed slicer-circle can contain one or more cutting elements, and the cutting elements can be positioned inside the hybridising region or in one end of the hybridising region (if the cutting element is a reactive chemical group). Therefore, the part of the preformed slicer-circle hybridising to the target nucleic acid molecule, may be divided into two or more hybridising parts. Thus, in one embodiment, the invention relates to a preformed slicer-circle probe, wherein the one or more elements having endonuclease activity is positioned internally in the target complementary sequence, dividing it into two or more parts, or wherein said element having endonuclease activity is a reactive chemical group positioned in one end of the target complementary region.

In a preferred embodiment one cutting element is used, which is positioned inside the hybridising part dividing it into two parts. Thus, in one embodiment, the invention relates to a nucleic acid probe of the preformed slicer-circle class, further comprising a first and a second part, each comprising a sequence of nucleic acid residues, which is at least 75% complementary to a target nucleic acid sequence, such as e.g. 80-100% complementary, or such as e.g. 85-100% complementary, 90-100% complementary, or such as e.g. 95-100% complementary, or such as e.g. 100% complementary. On RNA targets, a preferred embodiment of the invention relates to a preformed slicer-circle, wherein said first and second part each comprises a sequence of nucleic acid residues, which is at least 75% complementary to a target RNA sequence.

The first and second part of the preformed slicer-circle may have the same or different lengths, as long as both are capable of hybridising to the target nucleic acid molecule under reaction conditions. The first part of the preformed slicer-circle, comprising a nucleic acid sequence complementary to a target nucleic acid sequence, may have a linear length of 6-100. Thus, in one embodiment, the invention relates to a circular nucleic acid probe of the preformed slicer-circle class, wherein the length of said first part is 6-100 nucleotides, such as e.g. 10-100 nucleotides, or such as e.g. 10-80 nucleotides, or such as e.g. 10-60 nucleotides, or such as e.g. 10-40 nucleotides, or such as e.g. 10-30 nucleotides. The second part of the preformed slicer-circle probe, comprising a nucleic acid sequence complementary to a target nucleic acid sequence, may have a linear length of 6-100. Thus, in one embodiment, the invention relates to a circular nucleic acid probe, the preformed slicer-circle, wherein the length of said second part is 6-100 nucleotides, such as e.g. 10-100 nucleotides, or such as e.g. 10-80 nucleotides, 10-60 nucleotides, or such as e.g. 10-40 nucleotides, or such as e.g. 10-30 nucleotides.

A slicer-padlock probe is characterised by comprising two or more target recognising parts and one or more cutting elements (as slicer probes in general). The slicer-padlock probe (FIG. 1G) has two or more parts, each of which comprises a sequence of nucleic acid residues which is at least 75% complementary to a region of the target nucleic acid sequence, thereby enabling externally templated ligation using the target nucleic acid as ligation template.

Thus in a preferred design the slicer-padlock probe comprises (FIG. 1G):
  i) Two or more parts, each part comprising a sequence of nucleic acid residues which is at least 75% complementary to a region of the target nucleic acid sequence, and
  ii) an element defining the specific probe, and
  iii) one or more cutting elements It is to be understood that both the circularisation/ligation of the slicer-padlock and the binding of the cutting element require target recognition, and that the circularisation/ligation and cutting elements may recognise either the same or different targets (FIG. 1G).

With the cutting element placed inside the circularisation/ligation element of the padlock probe, the circularisation and the cleavage functions recognise the same target molecule and the same part of that target molecule. If the cutting element is placed outside of the one or more target recognising parts responsible for circularisation of the padlock probe, the slicer-probe can recognise two or more target molecules, or two or more parts of the same target molecule. In the latter case(s) the slicer-probe will report on the co-localisation of two or more targets.

A slicer-padlock can contain one or more cutting elements, and the cutting element can be positioned both inside either target-hybridising free nucleic acid part, or, if the cutting element is a reactive chemical group, in one end of the free nucleic acid end part hybridising closest to the 3'-end of the target nucleic acid molecule. Therefore, the parts of the slicer-padlock hybridising to the target nucleic acid molecule may be divided into three or more hybridising parts. Thus, in one embodiment, the invention relates to a slicer-padlock probe, wherein the one or more elements having endonuclease activity is positioned internally in the target complementary sequence, dividing it into three or more parts, or wherein said cutting element is a reactive chemical group positioned in one end of the hybridising region.

In a preferred embodiment, one cutting element positioned inside one of the hybridising parts is used, dividing the target recognising parts of the slicer-padlock into three parts (FIG. 1G). Thus, in one embodiment, the invention relates to a nucleic acid probe of the slicer-padlock class, further comprising a first, a second part, and a third part, each comprising a sequence of nucleic acid residues, which is at least 75% complementary to a target nucleic acid sequence, such as e.g. 75-100% complementary, such as e.g. 80-100% complementary, or such as e.g. 85-100% complementary, 90-100% complementary, or such as e.g. 95-100% complementary, or such as e.g. 100% complementary.

On RNA targets, another preferred embodiment of the invention relates to a circular nucleic acid probe, the slicer-padlock, comprising a first, a second and a third part of nucleic acid residues, wherein said first, second and third part each comprises a sequence of nucleic acid residues, which is at least 75% complementary to a target RNA sequence.

The first, second and third part of the slicer-padlock may have the same or different lengths, as long as they are all capable of hybridising to the target nucleic acid molecule under reaction conditions. The first part of the preformed slicer-circle probe, comprising a nucleic acid sequence complementary to a target nucleic acid sequence, may have a linear length of 6-100. Thus, in one embodiment, the invention relates to a circular nucleic acid probe of the slicer-padlock class, wherein the length of said first part is 6-100 nucleotides, such as e.g. 6-100 nucleotides, or such as e.g. 6-80 nucleotides, or such as e.g. 6-60 nucleotides, or such as e.g. 8-40 nucleotides, or such as e.g. 10-30 nucleotides. The second part of the slicer-padlock probe, comprising a nucleic acid sequence complementary to a target nucleic acid sequence, may have a linear length of 6-100. Thus, in one embodiment, the invention relates to a circular nucleic acid probe of the slicer-padlock class, wherein the length of said second part is 6-100 nucleotides, such as e.g. 6-100 nucleotides, or such as e.g. 6-80 nucleotides, 6-60 nucleotides, or such as e.g. 8-40 nucleotides, or such as e.g. 10-30 nucleotides. The third part of the slicer-padlock probe, comprising a nucleic acid sequence complementary to a target nucleic acid sequence, may have a linear length of 6-100. Thus, in one embodiment, the invention relates to a circular nucleic acid probe, the slicer-padlock, wherein the length of said third part is 6-100 nucleotides, such as e.g. 6-100 nucleotides, or such as e.g. 6-80 nucleotides, 6-60 nucleotides, or such as e.g. 8-40 nucleotides, or such as e.g. 10-30 nucleotides.

Thus in one embodiment, the invention relates to a slicer-padlock comprising the sequence (SEQ ID NO:8)

5'-P-
CATCGGGAGAAGCTCATAGATTTATTTCCTCAATGCTGCTGCTGTACTAC
TAGTGATTTACTTGGATGTCTGACAGTCTAGGCTAGCTACAACGATGGTT
TGCAGAGACCCAGTGGC-3'
wherein P is a 5'-phosphate Thus in another embodiment, the invention relates to a slicer-padlock comprising the sequence (SEQ ID NO:9):

5'-P-
CCATGTCAAAATCACTCCCATTTATTTCCTCAATGCTGCTGCTGTACTAC
TAGTGATTT-ACTTGGATGTCTGTAAAGAGAGGCTAGCTACAACGAGATG
GCACCTGGCACCC-3'
wherein P is a 5'-phosphate Thus in another embodiment, the invention relates to a slicer-padlock comprising the sequence (SEQ ID NO:10):

5'-P-
TACTTCATCGCATCTTTGTGTTTATTTCCTCAATGCTGCTGCTGTACTAC
TAGTGATTT-ACTTGGATGTCTAGGGAAAAGGCTAGCTACAACGATAAGA
AATTCGATGCTGC-3'
wherein P is a 5'-phosphate Thus in another embodiment, the invention relates to a slicer-padlock comprising the sequence (SEQ ID NO:11):

5'-P-TAATTACTGATTGTGTATCTTTTATTTCCTCAATGCTGCTGCTGT
ACTACTAGTGATTT-ACTTGGATGTCTAGAACGTAGGCTAGCTACAACGA
AAATAGTAGTCATTTGC-3'
wherein P is a 5'-phosphate Thus in another embodiment, the invention relates to a slicer-padlock comprising the sequence (SEQ ID NO:12):

5'-P-
CTAGCAAAACCTCTCCTCAATGCTGCTGCTGTACTACTAGTGATTTACTT
TACAGCCAGG-CTAGCTACAACGAACACGTCTCCTCC-3'
wherein P is a 5'-phosphate Thus in another embodiment, the invention relates to a slicer-padlock comprising the sequence (SEQ ID NO:13):

5'-P-
CGCACTGAGCGTTCCTCAATGCTGCTGCTGTACTACTAGTGATTTACTTG
GACTTGAGG-CTAGCTACAACGACTCGGGTCGGTAGCAC-3'
wherein P is a 5'-phosphate The different probes described above, may be used for the detection of nucleic acids both in solution, in situ, and in array based assays as outlined below in detail.

Detecting nucleic acid molecules by target primed rolling circle replication has the advantage of strong signal amplification and a localised signal due to the target primed feature of the reaction.

In one aspect of the invention, the target primed rolling circle reaction is primed from the natural 3'-end of the nucleic acid molecule. Since this method requires the presence of a 3'-end at or near the region in the RNA where the probe hybridises, the target RNA may preferably be a non-polyadenylated RNA, such as, but not limited to, EBER1 and EBER2 from the Epstein-Barr virus, the adenovirus-encoded small RNA's VA1 and VA2, ribosomal RNA's, the RNA part of the telomerase complex (hTERC), small interfering RNA's (siRNA's), and micro-RNA's (miRNA's). Thus, in one embodiment, the invention relates to a method for the detection of target RNA molecules, said method comprising hybridising a circular nucleic acid probe, which is a preformed circle probe, a padlock probe, or a circular nucleic acid probe of the turtle class, with a target RNA sequence, at or near the 3'-end of the target RNA molecule, performing rolling circle replication, and detecting the rolling circle product.

Thus in this embodiment, the invention may relate to a method comprising:
i) obtaining a preparation containing the target RNA molecule, and
ii) providing the circular nucleic acid probe, and
iii) hybridising said probe with the target RNA molecule at or near the 3'-end of said target RNA molecule, and
iv) effecting rolling circle replication with said probe as template
and detecting said target RNA molecule by visualising the rolling circle product.

Alternatively, the invention also relates to a method for the detection of a target nucleic acid molecule, said method comprising hybridising a circular nucleic acid probe, which is a preformed circle probe, a padlock probe, or a circular nucleic acid probe according to the present invention, with a target nucleic acid sequence, at or near the 3'-end of the target nucleic acid molecule, performing rolling circle replication and detecting the rolling circle product, wherein the target nucleic acid is a RNA molecule In one embodiment said method comprises:
i) obtaining a preparation containing the target RNA molecule, and
ii) providing the circular nucleic acid probe, and iii) hybridising said probe with the target RNA molecule at or near the 3'-end of said target RNA molecule, and
iv) ligating the circular probe to form a closed circular structure using the target nucleic acid molecule as ligation template or using a ligation template intrinsic to the circular nucleic acid probe.
v) effecting rolling circle replication with said probe as template
vi) detecting said target RNA molecule by visualising the rolling circle product wherein step iv) may also be performed before step iii).

If the probe used is a turtle probe or a padlock probe, a ligation step is required before effecting rolling circle replication. Thus in this embodiment the invention may further relate to a method, wherein said probe is a padlock probe or a circular nucleic acid probe of the turtle class, wherein the method further comprises a step of ligating the probe to form a closed circular structure (FIGS. 5 and 7) (example 3 and 5).

However, if the target DNA is chromatin DNA or DNA containing modifications e.g. resulting from degradation, preparation, or fixation, such as e.g. addition of mono-methylol (—$CH_2OH$) groups to the bases of the nucleic acids, resulting in dimerisation of adenine groups by methylene bridging, self-templated ligation, obtained by using a turtle probe may be preferable. Thus, in another embodiment, the invention refers to a method for the detection of target DNA molecules, said method comprising hybridising a circular nucleic acid probe of the turtle class, with a target DNA sequence, at or near the 3'-end of the target DNA molecule, performing rolling circle replication and detecting the rolling circle product.

Detecting nucleic acid molecules by target primed rolling circle replication may also be performed in situ, which has several advantages: it provides information about the expression of certain RNA molecules, it reveals in which type of cells the RNA is found, and it provides information on where the RNA is present in the cell, e.g. in the nucleus or in the cytoplasm. The importance of single cell detection, and the location of the RNA species inside the cell, is often underestimated as a result of the focus on array based technologies. However, since an incorrectly situated RNA can have detrimental consequences for the cell, for example if a messenger RNA or a ribosomal RNA is retained in the nucleus, the location, of the RNA, inside the cell cannot be disregarded. Also, most other techniques (e.g. the PCR-based and the array-based) use RNA extracted from several cells, and thus averages over different types of cells each having a different expression profile depending on both the type of cell and on the regulation from the surrounding cells. An expression profile will therefore often represent an average over a pool of cells. Consequently, if e.g. half of the cells do not express a certain RNA, and the other half expresses it in higher amounts than normal, the conclusion could be that all cells expressed the RNA in normal amounts. Thus, in one embodiment, the invention relates to a method, wherein the detection of said target RNA molecule occur in situ (FIGS. 5-7) (example 3-5).

In practice, this embodiment may e.g. take the following form:

Depending upon whether the target RNA molecule is provided as tissue or cells, different pretreatments may be required, for example in the form of deparaffination of paraffin embedded tissue, or in the form of cell wall degradation if cells are e.g. plants or yeast. However the procedure after the pretreatment is similar for the different cells or tissues, with small changes to the procedure depending on the type of circle probe used (e.g. omission of the ligation step if a preformed circle is used).

The probe is mixed in a hybridisation mix to a final concentration of 0.001-100 μM, preferably 0.01-10 μM. The hybridisation mix used contains: 20% formamide, 2×SSC, 5% glycerol 1 μg/μl carrier DNA. This hybridisation mix may also contain carrier RNA and the amount of carrier DNA, carrier RNA, formamide and glycerol may be changed to fit specific requirements. The hybridisation mix is added to the preparation containing the target nucleic acids and incubated at 95° C. for 0.5-60 minutes, preferable 2-10 minutes, then cooled to 37° C. and incubated for 5-30 minutes (extended hybridisation can be performed at 37° C. over night). Alternatively hybridisation can be performed at 37° C. without heating to 95° C. It is to be understood that the hybridisation temperature can be different e.g. depending on the melting temperature of the probe used.

After hybridisation of the probe, ligation may be performed using the T4 DNA ligase. Depending on the type of circle probe used, different conditions are required for ligation, and if the circle probe is a preformed circle, the ligation step is omitted.

Preferably, the circle probe used is a turtle probe, since the turtle probe contains its own ligation template. This allows the ligation reaction to be performed with several different DNA ligases e.g. but not limited to, any of the ligases: T4 DNA ligase, Tsc ligase, Tth ligase, Pfu ligase, Taq ligase, Ampligase or *E. coli* DNA ligase. Preferably the T4 DNA ligase (Fermentas) is used in a concentration of 0.05-0.15 U/μl, alternatively 0.001-0.7 U/μl could be used. RNase inhibitor may be added e.g. but not limited to the Ribolock RNase inhibitor (Fermentas). A final concentration of 0.01-2 U/μl, preferably 0.5-1.5 U/μl Ribolock (Fermentas) is used. If the ligation reaction takes place in cells or tissue, addition of BSA to a final concentration of 0.05-0.5 μg/μl, alternatively 0.01-1 μg/μl may improve the enzymatic reaction. An incubation time of 2 minutes to 24 hours, preferably 5 minutes to 5 hours is used at a temperature suitable for the ligase of choice.

Alternatively, the circle probe could be a padlock probe, which is ligated using the target RNA as template. This ligation reaction is less efficient than what is obtained with the turtle probe, and is most efficiently performed using the T4 DNA ligase in a buffer (according to Nilsson M. et al. Nat Biotechnol. 18(7):791-3. (2000)) containing: 10 mM Tris-HCL (pH7.5 at 25° C.), 10 mM $MgCl_2$, 10 μM ATP and 0.1 U/μl T4 DNA ligase (Fermentas). If the ligation reaction takes place in cells or tissue, addition of BSA to a final concentration of 0.05-0.5 μg/μl, alternatively 0.01-1 μg/μl, may improve the enzymatic reaction. An incubation time of 5 minutes to 24 hours, preferably 15 minutes to 5 hours, are used at 37° C. Alternatively, the T4 RNA ligase or Ampligase may be used.

If the probe does not hybridise exactly at the 3'-end of the target nucleic acid, an enzyme comprising 3'→5' exonuclease activity may be used to recess the 3'-end of the target nucleic acid molecule to the point where rolling circle replication can commence. Preferably, this enzyme is a DNA polymerase both comprising 3'→5' exonuclease activity, and capable of performing rolling circle replication, e.g., but not limited to, the Phi29 DNA polymerase. However, if the polymerase used is incapable of providing the required 3'→5' exonuclease activity, an exonuclease comprising 3'→5' exonuclease activity or another polymerase comprising 3'→5' exonuclease activity can be used.

The rolling circle reaction is performed using the 3'-end of the target RNA as primer for the rolling circle replication. Preferably, the polymerase used is the Phi29 DNA polymerase since it comprises both 3'→5' exonuclease activity, strong strand displacement activity, and strong processivity. A final concentration of 0.001-2 U/µl, preferably 0.05-1.5 U/µl, Phi29 DNA polymerase (Fermentas) is used. A final dNTP concentration of 0.001-2 mM, preferably 0.05-1 mM, is used. Alternatively other polymerases e.g. the T7 DNA polymerase or Sequenase version 2.0 T7 DNA polymerase can be used. An incubation time of 10 minutes to 24 hours, preferably 20 minutes to 4 hours, at the temperature optimal for the polymerase of choice is used. RNase inhibitor may be added, e.g., but not limited to, the Ribolock RNase inhibitor (Fermentas). If the reaction takes place in cells or tissue, addition of BSA to a final concentration of 0.05-0.5 µg/µl, alternatively 0.01-1 µg/µl, may improve the enzymatic reaction. For some polymerases addition of Single Strand Binding protein (SSB) strongly increases the efficiency of the rolling circle replication. Since the Phi29 DNA polymerase is not enhanced by SSB, a concentration of 0 µg/µl SSB is preferably used. Alternatively a concentration of 0.001-0.2 µg/µl can be used. It is to be understood that the different variants of the rolling circle reaction, e.g., but not limited to, the hyperbranch reaction, also can be used for signal amplification.

The speed and duration of the elongation can be controlled by varying the concentrations of dNTP, polymerase, circle, primer and SSB. Furthermore, temperature and buffer conditions are adjustable.

In a preferred embodiment, the products are detected using labelled oligonucleotides (e.g. labelled with a fluorophore) complementary to part of the rolling circle product. Such oligonucleotides are added to a final concentration of 0.001-10 µM, preferably 0.01-0.5 µM. If multiplexed, these concentration intervals apply to each of the oligonucleotides. An incubation time of 5 minutes to 24 hours, preferably 10 minutes to 2 hours, are used at 37° C. The slide is washed in wash buffer to remove any unbound labelled oligonucleotides and dehydrated through an ethanol series of 70%, 85% and 99%. Alternatively, the rolling circle product can be detected by incorporating labelled nucleotides (natural or artificial nucleotides) during the rolling circle replication as described above. The slide is air-dried, mounting solution containing DAPI (e.g. VectorShield+DAPI) is added, and the slide is analysed.

For purified RNA, e.g. RNA extracted from tissue or cells, a procedure comprising steps similar to the detection in tissue and cells can be used. This may be performed in an array format by immobilising the target RNA on a solid support (e.g. microscope slides, ELISA plates, chips, beads etc.). Thus, in another embodiment, the invention relates to a method, wherein said target RNA is immobilised on a solid support. In principle, the RNA can be attached either unspecifically, e.g. through an antibody, or specifically e.g. through a capture oligonucleotide. If the attachment of the RNA is unspecific, the probe needs to provide target specificity. However, if a target RNA is attached specifically, e.g. through a capture oligonucleotide, the specificity could be provided exclusively by the capture oligonucleotide. Capture oligonucleotides recognizing individual exons may e.g. be positioned in an array, and a turtle probe, comprising a poly-T target complementary region, may be employed to display which exons exist as polyadenylated RNA. If the target RNA is nonpolyadenylated a circular probe, e.g. a turtle probe can be designed to hybridise at or near the 3'-end of the target RNA molecule and thereby provide the specificity required to distinguish specific RNA's. Thus, in another embodiment, the invention relates to a method further comprising the steps of:

i) Providing a capture oligonucleotide attached to a solid support, and ii) Hybridising said capture oligonucleotide with said target nucleic acid molecule, thereby attaching the target nucleic acid molecule to the solid support.

The following steps illustrates how array based detection of target RNA molecules can be performed, using streptavidine coated slides as solid support in combination with a capture oligonucleotide labelled with biotin and a turtle-probe.

In practice, this embodiment may e.g. take the following form:

a) Attachment of the capture oligonucleotide to the streptavidine coated slide, and
b) hybridisation of the target RNA to the capture-oligonucleotide, and
c) hybridisation of turtle-probe to the target RNA, and
d) ligation of the turtle-probe to form a closed circular structure, and
e) optional; modification/recessing of the 3'end to a point where rolling circle replication can commence, and
f) rolling circle replication, and
g) detection of the rolling circle product A capture oligonucleotide complementary to an area in the target RNA is attached to the streptavidine coated slide using a concentration of 0.01 pmol to 1 nmol capture oligonucleotide, preferably 0.1-100 pmol biotin-coupled-oligonucleotide is used. Preferably, a buffer containing 0.1 M Tris-HCl (pH 7.5 at 25° C.), 0.15 M NaCl and 0.05% Tween-20 is used. Alternatively, the hybridisation can be performed in a wide range of other buffers with a pH range of 5-8. The slide is washed in wash buffer to remove any unbound capture oligonucleotide.

In order to obtain immobilisation of the target RNA on the solid support; 0.01-10 pmol RNA, alternatively 0.001 pmol to 1 µmol RNA is added to the slide, comprising the attached capture oligonucleotide, preferably in a buffer containing 0.1 M Tris-HCl (pH 7.5 at 25° C.), 0.15 M NaCl and 0.05% Tween-20. Alternatively the hybridisation can be performed in a wide range of other buffers with a pH range of 5-8. The slide is washed in wash buffer to remove any unbound capture oligonucleotide.

Hybridisation of the turtle-probe to the target RNA is performed by adding the turtle-probe to the slide, comprising the target RNA attached to the slide through the capture oligonucleotide, in a concentration of 0.1-100 pmol turtle probe, alternatively 0.002 pmol to 2 µmol in a buffer containing 0.1 M Tris-HCl (pH 7.5 at 25° C.), 0.15 M NaCl and 0.05% Tween-20. Alternatively, the hybridisation can be performed in a wide range of other buffers with a pH range of 5-8. The slide is washed in wash buffer to remove unbound capture oligonucleotide.

Ligation of the turtle-probe, to form a closed circular structure, can be performed with (but not limited to) any of the ligases: T4 DNA ligase, Tsc ligase, Tth ligase, Pfu ligase, Taq ligase, Ampligase, or *E. coli* DNA ligase. Preferably the T4 DNA ligase (Fermentas) is used in a concentration of 0.1-1 U/µl, alternatively 0.0001-2 U/µl could be used. RNase inhibitor may be added e.g. but not limited to the Ribolock RNase inhibitor (Fermentas), in a final concentration of 0.01-2 U/µl, preferably 0.5-1.5 U/µl Ribolock (Fermentas). An incubation time of 2 minutes to 24 hours, preferably 10-60 minutes, is used at a temperature suitably for the ligase of choice. The slide is washed in wash buffer to remove the enzyme.

The rolling circle reaction is performed using the 3'-end of the target RNA as primer for the rolling circle replication. Preferably, the polymerase used is the Phi29 DNA polymerase since it comprises both 3'→5' exonuclease activity, strong strand displacement activity and strong processivity. A final concentration of 0.001-2 U/μl, preferably 0.05-1.5 U/μl, Phi29 DNA polymerase (Fermentas) is used. A final dNTP concentration of 0.001-2 mM, preferably 0.05-1 mM, is used. Alternatively other polymerases e.g. the T7 DNA polymerase or Sequenase version 2.0 T7 DNA polymerase can be used. An incubation time of 10 minutes to 24 hours, preferably 20 minutes to 4 hours, at the temperature optimal for the polymerase of choice is used. RNase inhibitor may be added, e.g., but not limited to, the Ribolock RNase inhibitor (Fermentas). If the reaction takes place in cells or tissue, addition of BSA to a final concentration of 0.05-0.5 μg/μl, alternatively 0.01-1 μg/μl, may improve the enzymatic reaction. For some polymerases addition of Single Strand Binding protein (SSB) strongly increases the efficiency of the rolling circle replication. Since the Phi29 DNA polymerase is not enhanced by SSB, a concentration of 0 μg/μl SSB is preferably used. Alternatively a concentration of 0.001-0.2 μg/μl can be used. It is to be understood that the different variants of the rolling circle reaction, e.g., but not limited to, the hyperbranch reaction, also can be used for signal amplification.

The speed and duration of the elongation can be controlled by varying the concentrations of dNTP, polymerase, circle, primer and SSB. Furthermore, temperature and buffer conditions are adjustable.

In a preferred embodiment, the products are detected using labelled oligonucleotides (e.g. labelled with a fluorophore) complementary to part of the rolling circle product. Such oligonucleotides are added to a final concentration of 0.001-10 μM, preferably 0.01-0.5 μM. If multiplexed, these concentration intervals apply to each of the oligonucleotides. An incubation time of 5 minutes to 24 hours, preferably 10 minutes to 2 hours, are used at 37° C. The slide is washed in wash buffer to remove any unbound labelled oligonucleotides and dehydrated through an ethanol series of 70%, 85% and 99%. Alternatively, the rolling circle product can be detected by incorporating labelled nucleotides (natural or artificial nucleotides) during the rolling circle replication as described above. The slide is air-dried, mounting solution containing DAPI (e.g. VectorShield+DAPI) is added, and the slide is analysed.

Alternatively, some of the steps can be combined, e.g. step b-d), resulting in a simpler protocol, comprising:
  a) Attachment of the capture oligonucleotide to streptavidine coated slide, and
  b) hybridisation of the target RNA to the capture oligonucleotide, hybridisation of the turtle-probe to the target RNA, and ligation of the turtle-probe, and
  c) rolling circle replication, and
  d) detection of the rolling circle product A capture oligonucleotide complementary to a part of the target RNA is attached to the streptavidine coated slide using a concentration of 0.01 pmol to 1 nmol capture oligonucleotide. Preferably 0.1-100 pmol biotin-coupled-oligonucleotide is used. Preferably, a buffer containing 0.1 M Tris-HCl (pH 7.5 at 25° C.), 0.15 M NaCl and 0.05% Tween-20 is used. Alternatively, the hybridisation can be performed in a wide range of other buffers with a pH range of 5-8. The slide is washed in wash buffer to remove unbound capture oligonucleotide.

In order to obtain immobilisation of the target RNA on the solid support, hybridisation of the turtle probe with the target RNA and ligation of the turtle-probe in one step; target RNA, probe and ligase is added to the slide simultaneously, containing the attached capture oligonucleotides, in a ligation buffer suitable for the ligase of choice. The concentrations may be similar to the more complex procedure described above; e.g. 0.01-10 pmol RNA, alternatively 0.001 pmol to 1 μmol RNA, 0.1-100 pmol turtle probe, alternatively 0.002 pmol to 2 μmol and 0.1-1 U/μl T4 DNA ligase, alternatively 0.001-2 U/μmixed in 1×T4 DNA ligase buffer. RNase inhibitor may be added to the mixture, e.g., but not limited to, the Ribolock RNase inhibitor (Fermentas), in a final concentration of 0.01-2 U/μl, preferably 0.5-1.5 U/μl Ribolock (Fermentas). An incubation time of 2 minutes to 24 hours, preferably 10-60 minutes, is used at a temperature suitable for the ligase of choice. The slide is washed in wash buffer to remove unbound RNA and probe, and to remove the enzyme.

The rolling circle reaction is performed using the 3'-end of the target RNA as primer for the rolling circle replication. Preferably, the polymerase used is the Phi29 DNA polymerase since it comprises both 3'→5' exonuclease activity, strong strand displacement activity and strong processivity. A final concentration of 0.001-2 U/μl, preferably 0.05-1.5 U/μl, Phi29 DNA polymerase (Fermentas) is used. A final dNTP concentration of 0.001-2 mM, preferably 0.05-1 mM, is used. Alternatively other polymerases e.g. the T7 DNA polymerase or Sequenase version 2.0 T7 DNA polymerase can be used. An incubation time of 10 minutes to 24 hours, preferably 20 minutes to 4 hours, at the temperature optimal for the polymerase of choice is used. RNase inhibitor may be added, e.g., but not limited to, the Ribolock RNase inhibitor (Fermentas). If the reaction takes place in cells or tissue, addition of BSA to a final concentration of 0.05-0.5 μg/μl, alternatively 0.01-1 μg/μl, may improve the enzymatic reaction. For some polymerases addition of Single Strand Binding protein (SSB) strongly increases the efficiency of the rolling circle replication. Since the Phi29 DNA polymerase is not enhanced by SSB, a concentration of 0 μg/μl SSB is preferably used. Alternatively a concentration of 0.001-0.2 μg/μl can be used. It is to be understood that the different variants of the rolling circle reaction, e.g., but not limited to, the hyperbranch reaction, also can be used for signal amplification.

The speed and duration of the elongation can be controlled by varying the concentrations of dNTP, polymerase, circle, primer and SSB. Furthermore, temperature and buffer conditions are adjustable.

In a preferred embodiment, the products are detected using labelled oligonucleotides (e.g. labelled with a fluorophore) complementary to part of the rolling circle product. Such oligonucleotides are added to a final concentration of 0.001-10 μM, preferably 0.01-0.5 μM. If multiplexed, these concentration intervals apply to each of the oligonucleotides. An incubation time of 5 minutes to 24 hours, preferably 10 minutes to 2 hours, are used at 37° C. The slide is washed in wash buffer to remove any unbound labelled oligonucleotides and dehydrated through an ethanol series of 70%, 85% and 99%. Alternatively, the rolling circle product can be detected by incorporating labelled nucleotides (natural or artificial nucleotides) during the rolling circle replication as described above. The slide is air-dried, mounting solution containing DAPI (e.g. VectorShield+DAPI) is added and the slide is analysed.

Furthermore, if the capture oligonucleotide is synthesised on the solid support step a) may be omitted reducing the protocol to:
  a) hybridisation of the target RNA to the capture oligonucleotide, hybridisation of the turtle-probe to the target RNA and ligation of the turtle-probe, and
  b) rolling circle replication, and
  c) detection of the rolling circle product If a preformed circle probe is used, the ligation step can be omitted in the complex protocol. In the simplified protocols, the ligase may be omitted, and the immobilisation of the target RNA on the solid support and the hybridisation of the turtle probe with the target RNA can preferably be performed using wash buffer instead of ligase buffer.

As previously mentioned, the capture oligonucleotides attaching the target RNA to the solid support can preferably be synthesised on the solid support. This can be done by standard chemical methods, such as e.g. beta-cyanoethyl phosphoramidite chemistry. Alternatively, the capture oligonucleotides may be attached to the solid support after synthesis through, e.g., but not limited to, streptavidine/biotin complexes. Thus, in one embodiment, the invention relates to a method, wherein the capture oligonucleotide is directly synthesised on the support, and in another embodiment, the invention relates to a method, wherein the capture oligonucleotide is labelled with a marker and attached to the solid support through binding of the marker to a receptor molecule immobilised on the solid support The probe, whether it is a turtle probe, a preformed circle probe, or padlock probe, may, as previously mentioned, hybridise at or near the 3'-end of the target nucleic acid molecule. Thus, in one embodiment, the invention relates to a method, wherein said circular nucleic acid probe hybridises 25 nucleotides or less from the 3'-end of the target nucleic acid molecule, such as e.g. 0-25 nucleotides, or such as e.g. 0-20 nucleotides, or such as e.g. 0-15 nucleotides, or such as e.g. 0-10 nucleotides, or such as e.g. 0-5 nucleotides, or such as e.g. 4 nucleotides, or such as e.g. 3 nucleotides, or such as e.g. 2 nucleotides, or such as e.g. 1 nucleotide, or such as e.g. 0 nucleotides.

If the probe does not hybridise exactly next to the 3'-end of the target nucleic acid, an enzyme comprising 3'→5' exonuclease activity may be used to recess the 3'-end of the target nucleic acid molecule to the point where rolling circle replication can commence. Thus, in another embodiment, the invention relates to a method, further comprising recessing the 3'-end of the target nucleic acid molecule, with an enzyme comprising 3'→5' exonuclease activity. Said enzyme comprising 3'→5' exonuclease activity may be e.g. a polymerase or an exonuclease comprising 3'→5' exonuclease. Thus, in yet another embodiment, the invention relates to a method, wherein said enzyme comprising 3'→5' exonuclease activity is selected from the group consisting of polymerases with 3'→5' exonuclease activity and exonucleases with 3'→5' exonuclease activity. Preferably this enzyme is a DNA polymerase both comprising 3'→5' exonuclease activity, and capable of performing rolling circle replication, e.g. but not limited to the Phi29 DNA polymerase. Thus, in another embodiment, the invention relates to a method, wherein said enzyme comprising 3'→5' exonuclease activity is a DNA polymerase comprising 3'→5' exonuclease activity. However, if the polymerase used is incapable of providing the required 3'→5' exonuclease activity, an exonuclease comprising 3'→5' exonuclease activity, and capable of recessing the 3'-end of the target nucleic acid, can be used. Thus, in another embodiment, the invention relates to a method, wherein said enzyme comprising 3'→5' exonuclease activity is an exonuclease comprising 3'→5' exonuclease activity.

In a second aspect, the invention relates to a method for the detection of target nucleic acid molecules using a slicer probe, which is able to create its own 3'-end, when hybridised to the target nucleic acid molecule. The slicer probe can be a slicer-turtle probe (FIG. 1H), a preformed slicer-circle probe (FIGS. 1E-F), or a slicer-padlock probe (FIG. 1G). Thus, in the following section it is to be understood that all probes mentioned comprise a slicer element unless otherwise stated.

Since slicer probes produce their own 3'-end upon hybridisation, the method of the invention is capable of working with any maximal length of target. However, enough nucleic acid residues should be present to ensure hybridisation between the target nucleic acid and the slicer probe under reaction conditions. If the hybridisation between the probe and its target are strengthened e.g. by incorporation of nucleic acid residues increasing the melting temperature such as PNA or LNA it may be possible to push the lower limit of nucleotides required to ensure hybridisation. Thus, in one embodiment, the invention relates to a method for the detection of a target nucleic acid molecule, said method comprising hybridising a probe, which is a circular nucleic acid probe of the turtle probe class, a preformed circle probe, or a padlock probe, to the target nucleic acid molecule, cleaving said target nucleic acid molecule with the element having endonuclease activity to produce a 3'-end within the target nucleic acid molecule, performing rolling circle replication from said new 3'-end and detecting the rolling circle product.

Thus in one embodiment, the invention relates to a method comprising:

i) obtaining a preparation comprising the target nucleic acid molecule, and
ii) providing the circular nucleic acid probe, and
iii) hybridising said probe with the target nucleic acid molecule, and
iv) cleaving the target nucleic acid molecule with the element having endonuclease activity, producing a new 3'-end and 5'-end within the nucleic acid molecule, and
v) effecting rolling circle replication from said new 3'-end within the target nucleic acid molecule with said probe as template and detecting said target nucleic acid molecule by visualising the rolling circle product.

The cutting element comprised by the slicer probe, enables the probe to cleave a target nucleic acid, producing a new 3'-end where it hybridises (FIG. 3b). Consequently, it is possible to target any region of any nucleic acid molecule, enabling the detection of e.g. eukaryotic messenger RNA, which is polyadenylated at the 3'-end. Slicer probes are therefore ideal for the detection of messenger RNA, or other RNA species where no suitable 3'-end for probe-hybridisation is present. Thus, in another embodiment, the invention relates to a method, wherein said target nucleic acid molecule is an RNA molecule.

Said method for the detection of target nucleic acid molecules, may employ any slicer probe. Preferably the slicer-turtle is used, and alternatively a preformed slicer-circle or a slicer-padlock may be used. If the slicer probe used is a slicer-turtle or a slicer-padlock, a step of ligating the probe, to form a closed circular structure, is required before the step of rolling circle replication. Thus in another embodiment, the invention relates to a method, wherein said probe is a circular nucleic acid probe of the slicer-turtle class, or a slicer-padlock probe and the method comprises a further step of ligating said probe to form a closed circular structure.

Detection of nucleic acid molecules by target primed rolling circle replication may, as previously mentioned, also be performed in situ, which has several advantages: it provides information about the expression of certain RNA molecules, it reveals in which type of cells the RNA is found, and it provides information on where the RNA is present in the cell, e.g. in the nucleus or in the cytoplasm. The importance of single cell detection, and the location of the RNA species inside the cell, is often underestimated as a result of the focus on array based technologies. However, since an incorrectly situated RNA can have detrimental consequences for the cell, for example if a messenger RNA or a ribosomal RNA is retained in the nucleus, the location inside the cell cannot be disregarded. Also, most other techniques (e.g. the PCR-based and the array-based) use RNA extracted from several cells, and thus averages over different types of cells each having a different expression profile depending on both the type of cell and on the regulation from the surrounding cells. An expression profile will therefore often represent an average over a pool of cells. Consequently, if e.g. half of the cells do not express a certain RNA, and the other half express it in higher amounts than normal, the conclusion could be that all cells expressed the RNA in normal amounts. Thus in another embodiment, the invention relates to a method, wherein said target nucleic acid molecule is detected in situ and said method further comprises fixing cells or tissue containing the target nucleic acid molecule on a surface (standard cytological or histological preparations) (FIG. 8) (example 6).

The slicer probes may be used in an array-based manner, similar to the array-based methods using a turtle-probe (without a slicer element). However, whereas the array-based methods, using a turtle probe (without a slicer element), are restricted by the requirement for a suitable 3'-end at or near the probe-binding region in the target nucleic acid, the array-based methods using a slicer probe can detect any nucleic acid, since it creates a new 3'-end upon hybridisation.

Such array-based detection is performed by immobilising the target nucleic acid on a solid support (e.g. microscope slides, ELISA plates, chips, beads etc.). Thus, in another embodiment, the invention relates to a method, wherein said target nucleic acid molecule is immobilised on a solid support. If rolling circle detection of nucleic acid molecules are performed in an array-based format, the method will comprise some additional steps besides the steps already mentioned for nucleic acid detection using slicer probes. Thus, in another embodiment, the invention relates to a method further comprising the steps of:

i) Providing a capture oligonucleotide attached to a solid support, and
ii) Hybridising said capture oligonucleotide with said target nucleic acid molecule, thereby attaching the target nucleic acid molecule to the solid support.

Such an approach using slicer probes seems particularly promising for RNA detection, since the slicer probes can be used to detect different splice-variants or different RNA species. Thus, in another embodiment, the invention relates to a method, wherein said target nucleic acid molecule is RNA (FIG. 4) (example 2).

The capture oligonucleotides attaching the target RNA to the solid support can preferably be synthesised on the solid support. This can be done by standard chemical methods, such as e.g. beta-cyanoethyl phosphoramidite chemistry, alternatively the capture oligonucleotides may be attached to the solid support after synthesis through, e.g., but not limited to, streptavidine/biotin complexes or covalent-linking (e.g. Codelink activated slides from Amersham Boisciences). Thus, in one embodiment, the invention relates to a method, wherein the capture oligonucleotide is directly synthesised on the support, and in another embodiment, the invention relates to a method, wherein the capture oligonucleotide is labelled with a marker and attached to the solid support through binding of the marker to a receptor molecule immobilised on the solid support.

Furthermore, when using slicer probes, the nucleic acid molecules may be bound non-specifically to the solid support, e.g. through an antibody, and slicer probes may then be used to select individual specific target nucleic acids. Thus, in one embodiment, the invention relates to a method, wherein the target nucleic acid molecule is attached to the solid support through an antibody. Such an antibody could e.g. be directed against the 5'-cap of a polyadenylated messenger RNA. Thus, in another embodiment, the invention relates to a method, wherein the target RNA molecule is attached to the solid support through an antibody targeting the 5'-cap of the nucleic acid molecule, either directly or indirectly, e.g. through the CAP binding protein.

When using a slicer probe for cleaving a target nucleic acid, the resulting new 3'-end, required for priming the rolling circle replication, may need to be modified for the polymerase or exonuclease to recognise the 3'-end. Normally the 3'-end will comprise a hydroxyl group, but if the cutting element comprised by the slicer probe is e.g. the 10-23 or 8-17 DNAzyme, the 3'-end produced will be a one base overhang containing a 2',3'-cyclic phosphate (FIG. 3A). Such 2',3'-cyclic phosphates will inhibit at least some polymerases, e.g. the preferred polymerase (the Phi29 DNA polymerase) and a modification step may therefore be required (FIG. 4E). Thus, in another embodiment, the invention relates to a method, wherein said new 3'-end of the target nucleic acid molecule is modified to obtain a free hydroxyl group.

Removal of the 2',3'-cyclic phosphate produced by most DNAzymes, may be done using the T4 polynucleotide kinase, which comprises both a kinase and a phosphatase activity (compare FIGS. 4D and 4E). Thus, in another embodiment, the invention relates to a method, wherein said new 3'-end of the target nucleic acid molecule is modified the T4 polynucleotide kinase. Alternatively, if the DNAzyme is e.g. the 17E DNAzyme, which has been reported to produce a 3'-phosphate (or 2'-phosphate) instead of a 2',3'-cylic phosphate (Brown A K et al. Biochemistry 17; 42(23):7152-61 (2003)), any enzyme comprising phosphatase activity may be used to modify the 3'-end, e.g., but not limited to, the Calf Intestinal Alkaline Phosphatase (CIAP), Bacterial Alkaline Phosphatase (BAP), and Shrimp Alkaline Phosphatase (SAP).

If the cutting element is e.g. a 10-23 DNAzyme, an 8-17 DNAzyme, or a 17E DNAzyme, a one base overhang is produced at the new 3'-end of the target nucleic acid. This one base overhang may need to be removed for the 3'-end to prime the rolling circle replication. Enzymes, comprising 3'→5' exonuclease activity, may be used for removing the one base overhang. Thus, in another embodiment, the invention relates to a method wherein said new 3'-end of the target nucleic acid molecule is modified by an enzyme comprising 3'→5' exonuclease activity. Said enzyme comprising 3'→5' exonuclease activity may be e.g. a polymerase or an exonuclease comprising 3'→5' exonuclease. Thus, in yet another embodiment, the invention relates to a method, wherein said new 3'-end of the target nucleic acid molecule is modified by an enzyme selected from the group consisting of polymerases with 3'→5' exonuclease activity and exonucleases with 3'→5' exonuclease activity. Preferably the enzyme, comprising 3'→5' exonuclease activity, is a DNA polymerase both comprising 3'→5' exonuclease activity, and capable of performing rolling circle replication, e.g., but not limited to, the Phi29 DNA polymerase. Thus, in a preferred embodiment, the invention relates to a method, wherein said enzyme, comprising 3'→5' exonuclease activity, is a DNA polymerase comprising 3'→5' exonuclease activity, such as e.g. Phi29 DNA polymerase, or such as e.g. T4 DNA polymerase, or such as e.g. T7 DNA polymerase, or such as e.g. Deep Vent DNA polymerase, or such as e.g. DNA polymerase I, or such as e.g. Klenow Fragment, or such as e.g. Vent DNA polymerase, or such as e.g. 9° $N_m$ DNA polymerase, or such as e.g. isothermal Bst DNA polymerase. However, if the polymerase used is incapable of providing the required 3'→5' exonuclease activity, an exonuclease comprising 3'→5' exonuclease activity, and capable of recessing the 3'-end of the target nucleic acid, may be used in addition. Thus, in another embodiment, the invention relates to a method, wherein said enzyme, comprising 3'→5' exonuclease activity, is an exonuclease comprising 3'→5' exonuclease activity, such as e.g. exonuclease T, or such as e.g. CCR4, or such as e.g. Rrp6p, or such as e.g. Exosome complex exonuclease RRP41.

In some procedures a two enzyme system might thus be preferred, which could be e.g. a polymerase without 3'→5' exonuclease activity combined with either an exonuclease comprising 3'→5' exonuclease activity or another polymerase comprising 3'→5' exonuclease activity. Another situation where a two enzyme system, in this case comprising two polymerases, might be preferred is when the polymerase used for rolling circle replication is incapable of incorporating certain nucleotides, e.g. artificial or modified. This inability may then be compensated for by the addition of a second polymerase, capable of incorporating such nucleotides, such as e.g. Klenow Fragment, or such as e.g. Taq polymerase, or such as e.g. 9° $N_m$ DNA polymerase, or such as e.g. Therminator DNA polymerase, or such as e.g. Pwo DNA polymerase, or such as e.g. Pfu DNA polymerase, or such as e.g. DNA polymerase I, or such as e.g. Vent DNA polymerase, or such as e.g. Tth DNA polymerase, or such as e.g. isothermal Bst DNA polymerase.

The target nucleic acids mentioned in the different methods may be obtained from cells or from tissue. Thus, in one embodiment, the invention relates to a method, wherein the preparation comprising target nucleic acid molecule is provided from cells selected from the group consisting of mammalian, bacterial, yeast, reptile, amphibian, avian and plant cells and in another embodiment, the invention relates to a method, wherein the preparation comprising target nucleic acid molecule is provided from tissue selected from the group consisting of mammalian, reptile, amphibian, avian and plant tissue. In another embodiment, the invention relates to a method, wherein the cells are mammalian cells. In another embodiment, the invention relates to a method, wherein the tissue is mammalian tissue. In another embodiment, the invention relates to a method, wherein the cells are human cells. In another embodiment, the invention relates to a method, wherein the tissue is human tissue.

Nucleic acids originating from viruses can also be detected by the methods mentioned above. However, since viruses both have a stage inside and outside a host cell, nucleic acids originating from a virus may be detected also from body fluids or excretions such as but not limited to, spinal fluid, or such as urine, or such as faeces, or such as salvia, or such as blood. Thus, in another embodiment, the invention relates to a method, wherein the preparation comprising target nucleic acid molecule is provided from virus.

Since target primed rolling circle replication detects single molecules, one signal equals one target nucleic acid molecule. Thus, by counting the number of signals, and possibly comparing it to a reference, a measurement of the total amount of target nucleic acid molecules may be obtained. Thus, in one embodiment, the invention relates to a method, wherein the amount of target nucleic acid molecules are measured quantitatively by counting the number of rolling circle replication signals. Alternatively, a measurement of the total amount of target nucleic acid molecules can be obtained by measuring the amount of fluorescence signal from the rolling circle replication. Again this may require the inclusion of internal or external references. Thus, in another embodiment, the invention relates to a method, wherein the amount of target nucleic acid molecules are measured quantitatively based on the measurement of the amount of fluorescence signal from the rolling circle replication.

The methods and probes mentioned can be used in diagnostic kits. Thus, in one embodiment, the invention relates to a kit of parts comprising a circular nucleic acid probe and at least one component selected from the group consisting of: buffers, reagents, antibodies, control preparations of one or more target nucleic acids. Any of the methods or probes mentioned may be used for in vitro diagnostics. Thus, in another embodiment, the invention relates to a diagnostic method applying any of the methods described and in another embodiment, the invention relates to a diagnostic method comprising hybridising a circular nucleic acid probe to a target nucleic acid molecule, wherein said circular nucleic acid probe is selected from the group comprising, turtle probes, preformed circle probes, padlock probes, slicer-turtle probes, preformed slicer-circle probes, or slicer-padlock probes.

Preferably said in vitro diagnostics are performed on RNA, e.g., but not limited to, detection of spliced RNA, alternative spliced messenger RNA, EBER1 and EBER2 from the Epstein-Barr virus, the adenovirus-encoded small RNA's VA1 and VA2, ribosomal RNA's, the RNA part of the telomerase complex (hTERC), small interfering RNA's (siRNA's), and micro-RNA's (miRNA's). Thus, in another embodiment, the invention relates to a diagnostic method, wherein said target nucleic acid molecule is RNA.

CROSS-REFERENCE TO RELATED APPLICATIONS

This application claims priority from DK PA 2005 00522, filed on Apr. 12, 2005.

Each of these applications, patents, and each document cited in this text, and each of the documents cited in each of these applications, patents, and documents ("application cited documents"), and each document referenced or cited in the application cited documents, either in the text or during the prosecution of the applications and patents thereof, as well as all arguments in support of patentability advanced during prosecution thereof, are hereby incorporated herein by reference.

In addition, singular reference does not exclude a plurality. Thus, references to "a", "an", "first", "second" etc. do not preclude a plurality.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As will be apparent, preferred features and characteristics of one aspect of the invention may be applicable to other aspects of the invention.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced by reference therein.

The invention will hereinafter be described by way of the following non-limiting Figures and Examples.

Different design of circle probes for use in rolling circle replication.

Originally, as mentioned in summary of the invention, there were two circle probe designs for use in rolling circle replication; this number has been increased to six. Enabling not only rolling circle replication from the natural 3'-end of the target molecule but also enabling a sequence specific creation of a new 3'-end at a desired point in the target molecule. A) Preformed circle probe. B) Preformed circle probe formed from a turtle probe, which does not require an external template for ligation; consequently there is no contamination of the circle probe with a template which could act as a rolling circle primer giving rise to false products. C) Padlock probe. D) Turtle probe. E) Preformed slicer-circle probe. F) Preformed slicer-circle probe, formed from a slicer-turtle. G) Slicer-padlock probe. H) Slicer-turtle probe. The numbers illustrates the different nucleic acid parts of the probe as they appear in the claims and in the detailed description, | denotes boundaries between elements or parts, CE denotes the cutting element and Id denotes the identifier element.

Figure 1:
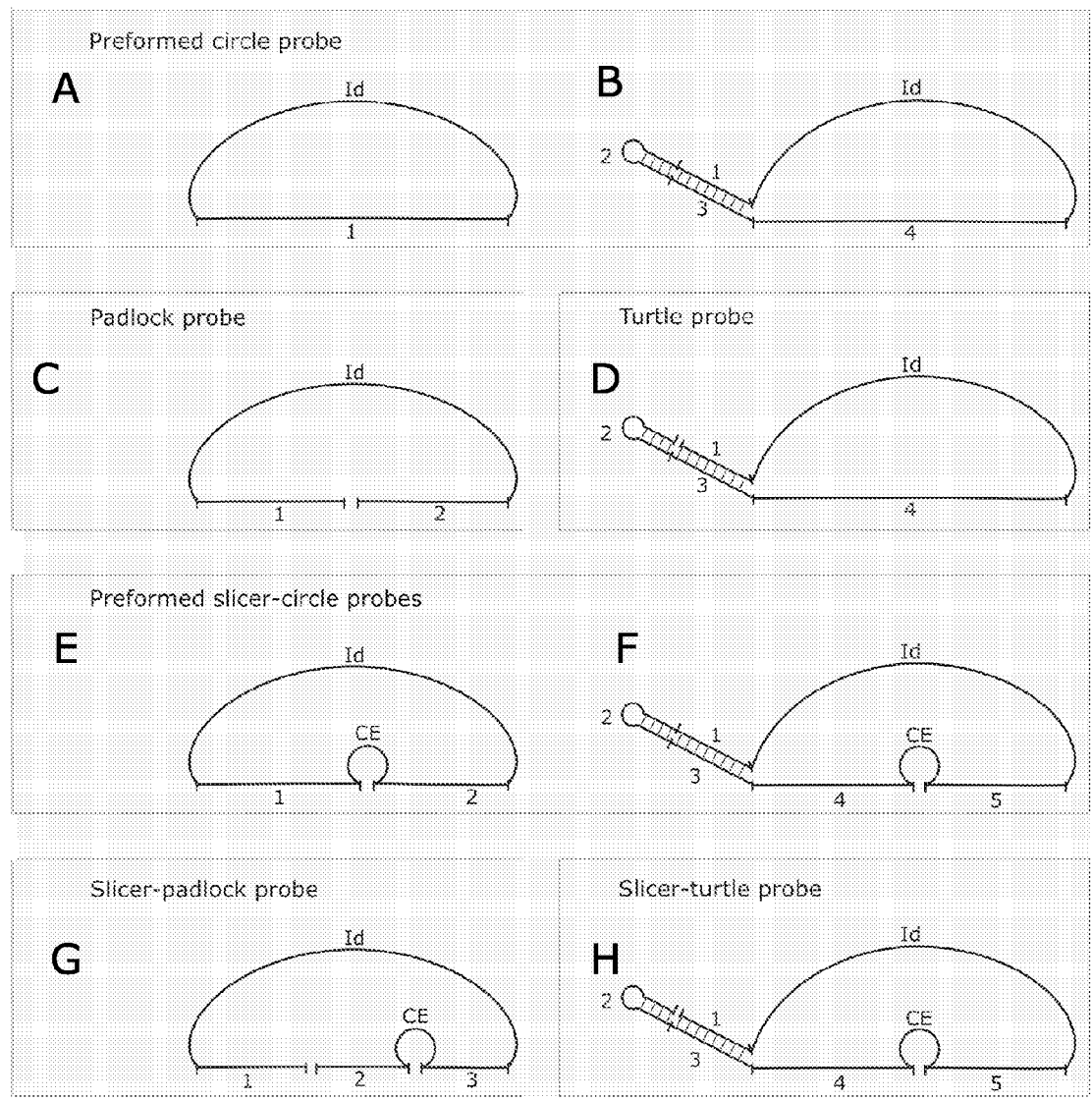
FIG. 1
Figure 2:
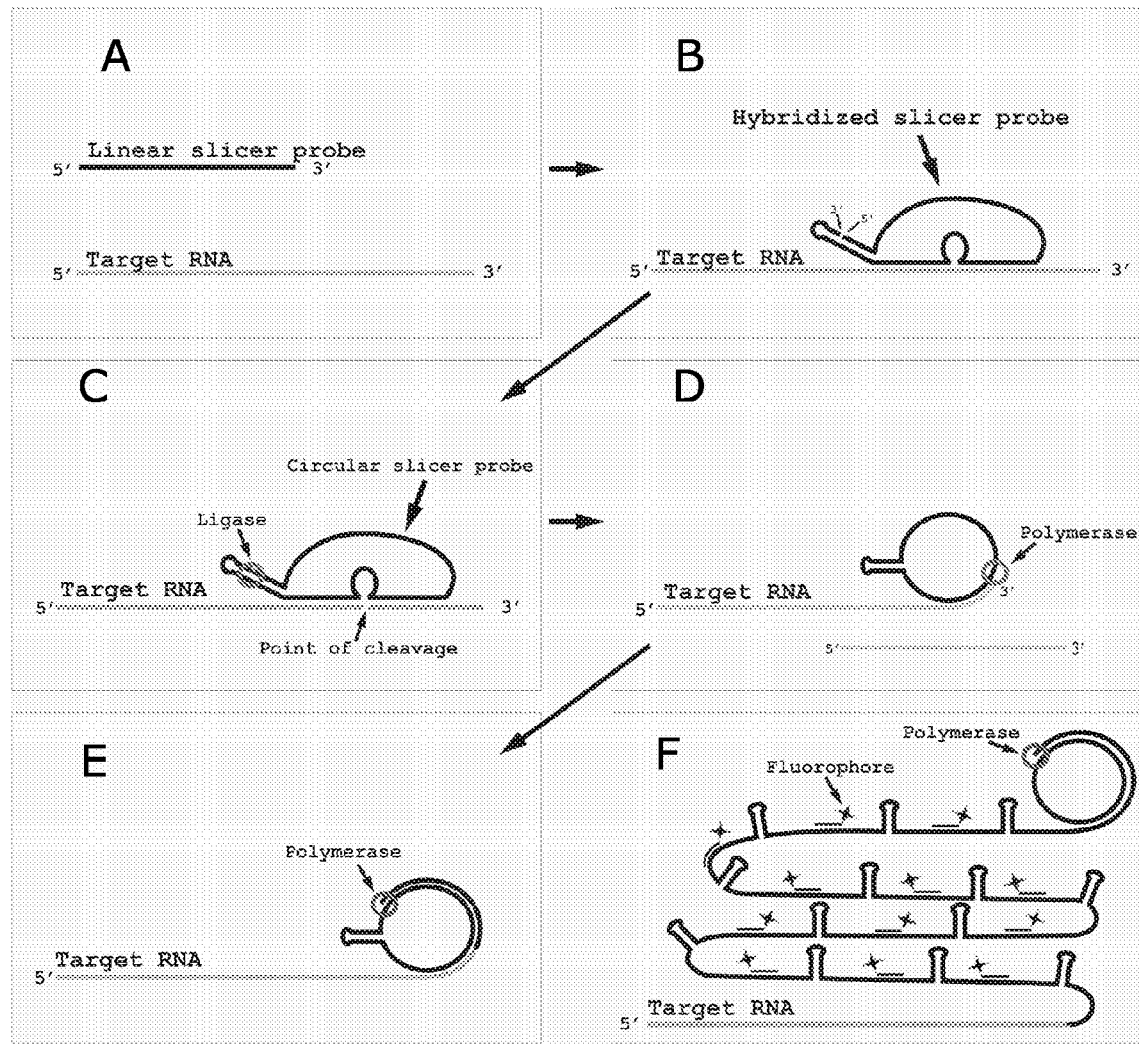
Figure 3:
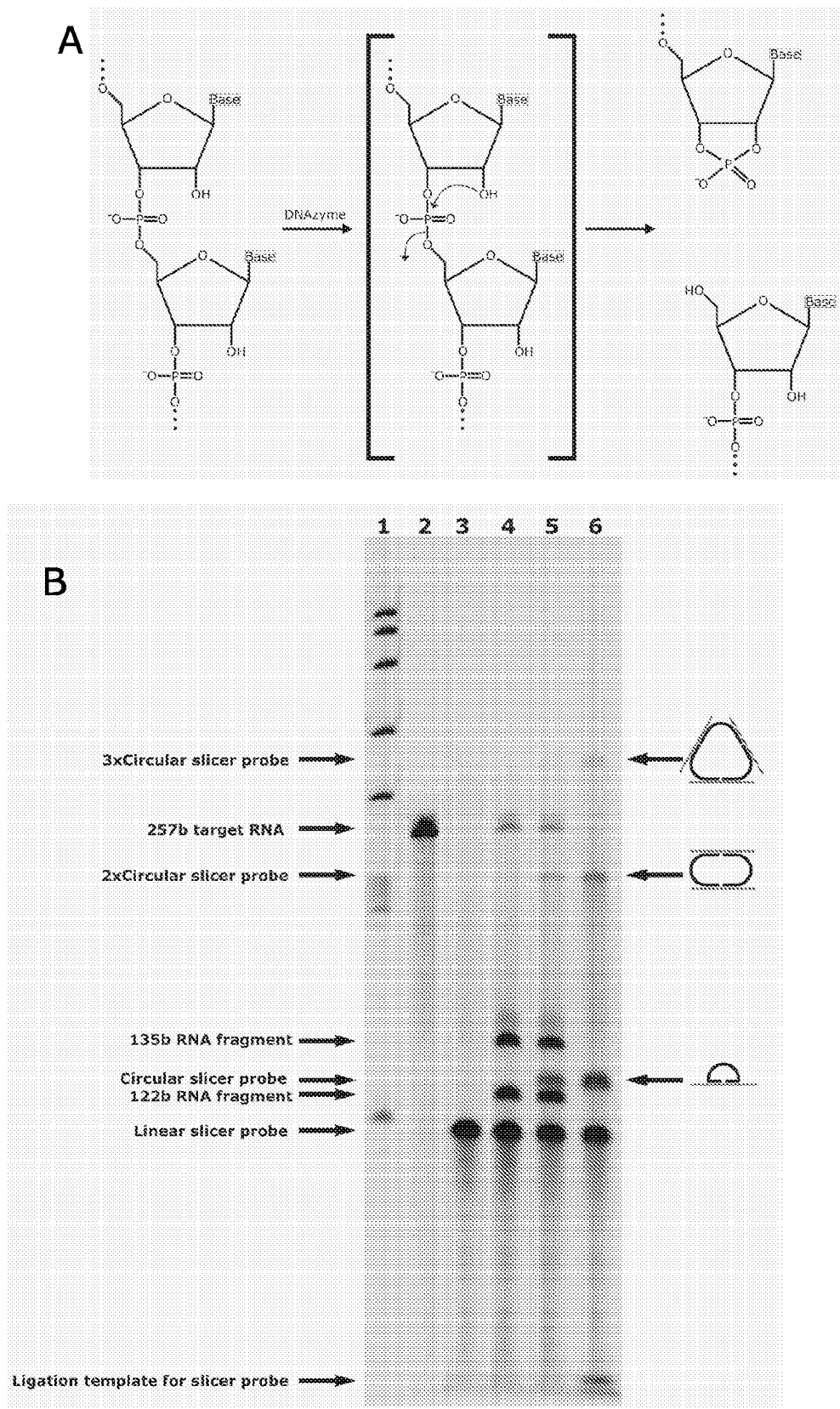

In the slicer-padlock (FIG. 1G), the cutting element has, for the sake of simplicity, been placed within the target recognising part used for circularisation/ligation of the probe, in which case the circularisation function and the cleavage function recognise the same target molecule and the same part of that target molecule. If the cutting element is placed outside of the target recognising part, the probe recognises two target molecules, or two separate parts of the same molecule. In the latter case the probe will report on the co-localisation of the two targets.

FIG. 2

Illustration of the rolling circle replication procedure using a slicer-probe.

The rolling circle procedure, illustrated with the slicer-turtle, divided into steps where; step A) Providing the slicer-probe and the target RNA; step B) Hybridisation of the slicer-turtle with the target RNA; step C) Ligation of the slicer-turtle to form a closed circular structure and cleavage of the target RNA; step D) and step E) Rolling circle replication; and step F) Detection of the rolling circle product by addition of a fluorescent coupled detection oligonucleotide. Cleavage can also be performed during hybridisation if desired, and modification of the cleavage-produced 3'-end can be performed between step C) and D).

FIG. 3

DNAzyme hydrolysis of target RNA.

DNAzymes are nucleic acid sequences, comprising enzymatic activity. These are usually created by in vitro selection experiments, and typically require divalent metal ions for activity. A) Show the hydrolysis of a target RNA, catalysed by the 10-23 DNAzyme, 17E DNAzyme and several other DNAzymes. B) Experiment using an in vitro transcribed RNA and a slicer-padlock probe with the 10-23 DNAzyme as cutting element illustrating the sequence specific formation of a new 3'-end (example 1). Lane 1 is the Low Range RNA Ladder (Fermentas); lane 2 is the in vitro transcribed target RNA, without slicer-padlock; lane 3 is the slicer-padlock, without RNA; lane 4 is the slicer-padlock and target RNA not incubated with the T4 DNA ligase; Lane 5 is the slicer-padlock and target RNA incubated with T4 DNA ligase, resulting in circularisation of the slicer-padlock; Lane 6 is the slicer-padlock and an external ligation template (DNA) with T4 DNA ligase.

FIG. 4

Solid support/array based RNA detection using a slicer probe.

The experiment was performed with a slicer-padlock probe, in vitro transcribed RNA, a biotin coupled capture oligonucleotide and streptavidine coated microscopic slides as solid support as described in example 2. A) Negative control where both the capture oligonucleotide and the target RNA were omitted. B) Negative control where the target RNA was omitted. C) Negative control where the capture oligonucleotide was omitted. D) The full reaction containing all reagents and steps (example 2). E) Negative control where T4 polynucleotide kinase was omitted. F) Negative control where a padlock probe was used instead of the slicer-padlock, both probes recognising the exact same nucleic acid sequence in the target RNA.

FIG. 5

In situ detection using a turtle probe.

In situ detection of the non-polyadenylated Epstein-Barr virus (EBV) RNA, EBER1, in EBV positive human tonsil tissue fixed in formalin and embedded in paraffin. Since the EBER1 RNA was non-polyadenylated, it was possible to use a probe without a cutting element hybridising in the 3'-end of the EBER1 RNA—in this case a turtle probe.

A) A section of the tonsil tissue treated as described in example 3, where arrows indicate rolling circle products, i.e. cells positive for EBER1 RNA. B) The design of the turtle probe used in example 3. ("SEQ ID NO: 1")

FIG. 6

In situ detection using a preformed circle.

In situ detection of the non-polyadenylated Epstein-Barr virus (EBV) RNA, EBER1, in EBV positive human tonsil tissue fixed in formalin and embedded in paraffin. Since the EBER1 RNA was non-polyadenylated, it was possible to use a probe without a cutting element hybridising in the 3'-end of the EBER1 RNA—in this case a pre-formed circle probe formed by ligation of a turtle probe prior to hybridisation. The reason for using a turtle probe to create the preformed circle probe instead of a padlock probe was that the turtle probe contains its own ligation template and no external addition of a ligation template was required. Therefore there was no contamination of the preformed circle with an oligonucleotide, which could act as a primer resulting in false rolling circle signals.

A) A section of the tonsil tissue treated as described in example 4, where arrows indicate rolling circle products, i.e. cells positive for EBER1 RNA. B) Shows the design of the circle probe used in example 4. ("SEQ ID NO: 3")

FIG. 7

In situ detection using a padlock probe.

In situ detection of the non-polyadenylated Epstein-Barr virus (EBV) RNA, EBER1, in EBV positive human tonsil tissue fixed in formalin and embedded in paraffin. Since the EBER1 RNA was non-polyadenylated, it was possible to use a probe without a cutting element hybridising in the 3'-end of the EBER1 RNA—in this case a padlock probe.

A) A section of the tonsil tissue treated as described in example 5, where arrows indicate rolling circle products, i.e. cells positive for EBER1 RNA. B) The design of the padlock probe used in example 5. ("SEQ ID NO: 18")

FIG. 8

In situ detection using a slicer-turtle probe.

In situ detection of the non-polyadenylated Epstein-Barr virus (EBV) RNA, EBER1, in EBV positive human tonsil tissue fixed in formalin and embedded in paraffin. The slicer-turtle probe was designed to hybridise to a region of the EBER1 RNA positioned 112 nucleotides from the 3'-end. A turtle probe, recognising the same region produced no signals (data not shown), indicating a requirement for a cutting element in this case.

A) A section of the tonsil tissue treated as described in example 6, where arrows indicate rolling circle products, i.e. cells positive for EBER1 RNA. B) The design of the slicer-turtle probe used in example 6. ("SEQ ID NO: 19")

FIG. 9

In situ detection using two different turtle probes in parallel (multiplexing).

In situ detection of the non-polyadenylated Epstein-Barr virus (EBV) RNA, EBER1, and the non-polyadenylated hTR (human telomerase RNA subunit) in EBV positive human Hodgkin's lymphoma tissue fixed in formalin and embedded in paraffin. Since both the EBER1 RNA and the hTR RNA were non-polyadenylated, it was possible to use probes without a cutting element hybridising in the 3'-end of the target RNA—in this case turtle probes.

A) A section of the Hodgkin's tissue treated as described in example 7, where the red channel has been removed so that only the green signals from the EBER1 probe and blue staining of the nuclei are visible.

B) A section of the Hodgkin's tissue treated as described in example 7, where the green channel has been removed so that only the red signals from the hTR probe and blue staining of the nuclei are visible.

EXAMPLES

Example 1

Cleavage of RNA Using a Slicer Probe with the 10-23 DNAzyme as Cutting Element

Ligation of the slicer-padlock, to form a closed circular structure, and cleavage of the RNA was done in one step.

The RNA used was a fragment of the 3'-UTR of the yeast SSA4 RNA transcribed in vitro, using the T7 RNA polymerase and the Puc18 vector, with a DNA fragment comprising part of the 3'-UTR of the yeast SSA4 inserted, as transcription template.

Cleavage of the SSA4 RNA was performed in a buffer comprising: 10 mM Tris-HCL (pH7.5 at 25° C.), 10 mM $MgCl_2$ and 10 µM ATP since These conditions was optimized for ligating DNA on an RNA template in solution (according to Nilsson M. et al. Nat Biotechnol. 18(7):791-3. (2000)). Since this buffer contains $Mg^{2+}$ cleavage of the target RNA may be performed simultaneously with ligation of the probe. The final concentration SSA4 RNA and SSA4-slicer-padlock probe was 0.5 µM and 1 µM, respectively. The reactions were incubated at 37° C. for 90 minutes and loaded on a 5% polyacrylamide gel.

```
In vitro transcribed target RNA (SEQ ID NO: 14):
5'-

GGGAUAAAUACAAAGAUGCGAUGAAGUAGCAGCAUCGAAUUUCUUAGUUU

UCCCUCUUAACA

ACUUUUUAUAAGUAUAUAUAUAAGAUACACAAUCAGUAAUUAGCAAAUGA

CUACUAUUUGUACGUUCUCAUCGUCAUAAGCCAGAGUUUAAUUAAGUGCC

UCAACCGGGAUGCGAUUUCGCGUUCAUAUACAAAGCCGAAAUGACAAUAA

GAAAGUCAUCGCCAAACAACACGACCCUUUAGUGAGGGUUAAUUG-3'

SSA4-slicer-padlock probe (SEQ ID NO: 11):
5'-P-

TAATTACTGATTGTGTATCTTTTATTTCCTCAATGCTGCTGCTGTACTAC

TAGTGATTTACTTGG

ATGTCTAGAACGTAGGCTAGCTACAACGAAAATAGTAGTCATTTGC-3'
Wherein
P is a 5'-phosphate
```

Example 2

Array Based RNA Detection Using a Slicer-Padlock Probe

Figure 4:
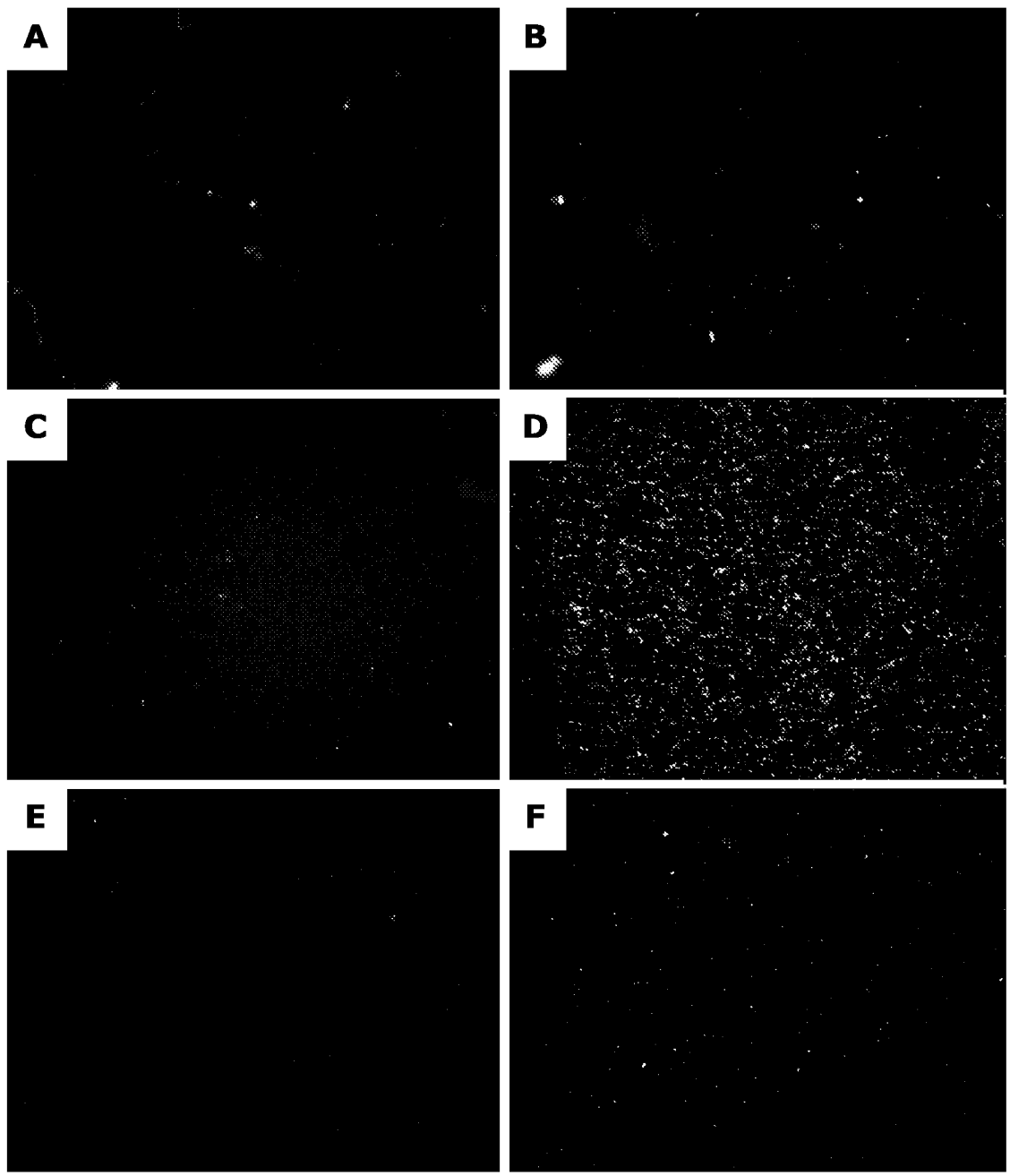

Array based detection of RNA using a streptavidine coated microscopic slide as solid support and in vitro transcribed SSA4 RNA (similar to the RNA used in example 1) as target RNA (FIG. 4).

The in vitro transcribed SSA4 RNA was produced using the T7 RNA polymerase and the Puc18 vector with a DNA fragment comprising the SSA4 sequence inserted as transcription template.

Hybridisation of Capture Oligonucleotide:

The capture oligonucleotide used in this assay was a 3'-biotin coupled oligonucleotide complementary to the 5'-end of an in vitro transcribed target RNA molecule and the solid support was provided in the form of a streptavidine coated microscopic slide. A plastic cover containing wells with a diameter of approximately 6 mm was attached to the slide in order to separate the different reactions. A final concentration of 1 µM capture oligonucleotide was attached to the streptavidine coated slide in a buffer containing: 10 mM Tris-HCl (pH 7.5 at 25° C.) and 10 mM $MgCl_2$. Dependent on scale of the solid support, larger or smaller amounts of capture oligonucleotide may be preferred. After hybridisation the slide was washed with wash buffer (0.1 M Tris-HCl, 0.15 M NaCl and 0.05% Tween-20) at 37° C.

Hybridisation, Ligation and Cleavage:

Hybridisation of target RNA molecules to capture oligonucleotide, ligation of SSA4-slicer-padlock probe, and cleavage of the target RNA molecules was performed in one step. This was done by adding the target RNA and probe to the slide in a mixture comprising 10 nM target RNA, 120 nM probe, 10 mM Tris-HCL (pH7.5 at 25° C.), 10 mM $MgCl_2$, 10 µM ATP, 5 mM DTT, 1 U/µl Ribolock (Fermentas) and 0.1 U/µl T4 DNA ligase (Fermentas), and incubating the slide for 30 minutes at 37° C. These ligation conditions were optimized for ligating DNA on an RNA template in solution (according to Nilsson M. et al. Nat Biotechnol. 18(7):791-3. (2000)). After incubation at 37° C. the slide was washed with wash buffer (0.1 M Tris-HCl, 0.15 M NaCl and 0.05% Tween-20) at 37° C.

3'-End Modification:

Since the slicer probe in this experiment was a slicer-padlock containing the 10-23 DNAzyme as cutting element (FIG. 8B), the cleavage produces a cyclic phosphate instead of a regular hydroxyl group at the 3'-end. The new 3'-end of the RNA therefore needed to be modified to enable the Phi29 DNA polymerase to commence rolling circle replication. This was done by removal the cyclic phosphate using the T4 polynucleotide kinase, producing a regular hydroxyl group at the 3'-end of the target RNA. This reaction was performed by adding 1 U/µl T4 polynucleotide kinase (Fermentas) in 1× exchange buffer (Fermentas) supplied with 0.3 M NaCl, 4 mM ATP and 1 U/µl Ribolock (Fermentas) and incubating the slide for 30 minutes at 37° C. After incubation at 37° C. the slide was washed with wash buffer (0.1 M Tris-HCl, 0.15 M NaCl and 0.05% Tween-20) at 37° C.

Rolling Circle Replication

Rolling circle replication uses the probe as rolling circle replication template and commences from the new 3'-end of the target RNA making it a target primed rolling circle replication. Rolling circle replication was performed in a mixture containing: 1×Phi29 reaction buffer (Fermentas), 0.25 mM dNTP, 1 U/µl Ribolock (Fermentas) and 0.25 U/µl Phi29 DNA polymerase (Fermentas) for 30 minutes at 37° C. After rolling circle replication the slide was washed by gently submerging it in wash buffer for 2 minutes at 37° C. to avoid disrupting the rolling circle replication products.

Detection of Rolling Circle Replication Product:

Detection of the rolling circle replication product was performed by adding a mixture containing: 10 mM Tris-HCl (pH 7.5 at 25° C.) and 10 mM $MgCl_2$, 5 mM DTT, 1 U/µl Ribolock (Fermentas), and 0.25 µM fluorescent probe A and 0.25 µM fluorescent probe B and incubating the slide for 30 minutes at 37° C.

To be able to distinguish between false signals and true signals, two fluorescent probes (probe A and probe B) were added, though only one anneals to the rolling circle replication product. The true signals were visible in the spectrum of probe A whereas false signals, if present, would be detectable in the spectra of both probe A and probe B.

After incubation at 37° C. the slide was washed by gently submerging is in wash buffer for 2 minutes at 37° C. to avoid disrupting the rolling circle replication products, dehydrated, mounted with VectorShield containing DAPI, and visualized under a fluorescent microscope.

```
In vitro transcribed target RNA (SEQ ID NO: 14):
5'-

GGGAUAAAUACAAAGAUGCGAUGAAGUAGCAGCAUCGAAUUUCUUAGUUU

UCCCUCUUAACAACUUUUUAUAAGUAUAUAUAUAAGAUACACAAUCAGUA

AUUAGCAAAUGACUACUAUUUGUACGUUCUCAUCGUCAUAAGCCAGAGUU

UAAUUAAGUGCCUCAACCGGGAUGCGAUUUCGCGUUCAUAUACAAAGCCG

AAAUGACAAUAAGAAAGUCAUCGCCAAACAACACGACCCUUUAGUGAGGG

UUAAUUG-3'
```

Streptavidine coated slides were purchased at Xenopore.

```
Capture oligonucleotide (SEQ ID NO: 15):
5'-AGAGGGAAAACTAAGAAATTCGATGCTGCTACTTC-z-3'
Wherein z is a biotin SSA4-slicer-padlock probe SEQ ID NO: 11):
5'-P-

TAATTACTGATTGTGTATCTTTTATTTCCTCAATGCTGCTGCTGTACTAC

TAGTGATTTACTTGG

ATGTCTAGAACGTAGGCTAGCTACAACGAAAATAGTAGTCATTTGC-3'
Wherein P is a 5'-phosphate

Fluorescent probe A (SEQ ID NO: 16):
5'-x-CCTCAATGCTGCTGCTGTACTAC-3'
Wherein x is the fluorphore TAMRA (Rhodamine)

Fluorescent probe B (SEQ ID NO: 17):
5'-y-CCTCAATGCACATGTTTGGCTCC-3'
Wherein y is the fluorphore FAM (FITC)
```

All probes were purchased from DNA Technology A/S.

Example 3

In Situ Detection of RNA Using a Turtle Probe

Figure 5:
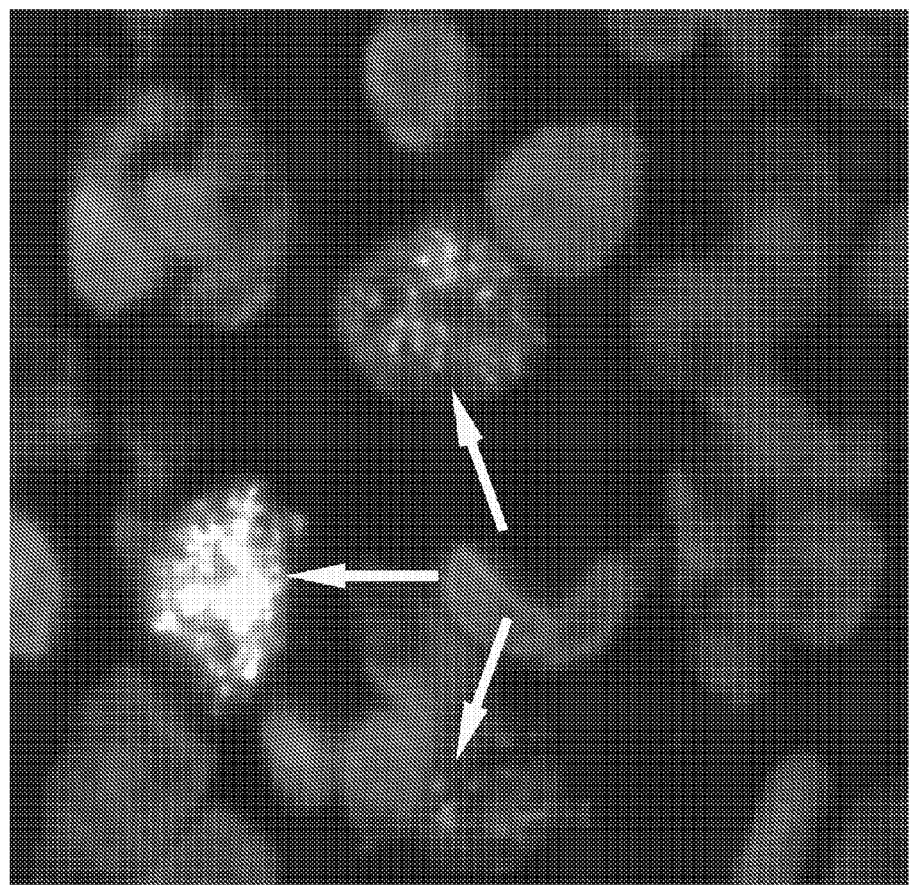
Figure 5:
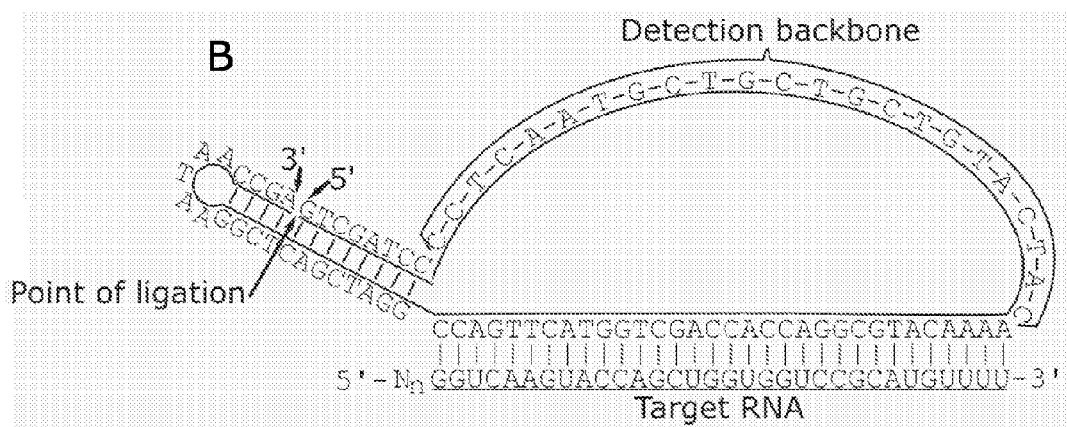

In situ detection of EBER1 (Epstein-Barr Early Region) RNA in paraffin embedded formalin fixed human tonsil tissue infected with Epstein-Barr virus (EBV) (see FIG. 5).

Pretreatment: The formalin fixed paraffin embedded tissue was deparaffinised with xylen for 2×10 minutes and then washed in an ethanol series of 99%, 85%, 70% to remove residual xylen. The tissue was then dehydrated and air dried at room temperature. The tissue was treated with 0.05% pepsin (Sigma) dissolved in 0.1 M HCl for 15 minutes at 37° C. The pepsin treatment was terminated by submerging the slide in wash buffer (0.1 M Tris-HCl, 0.15 M NaCl and 0.05% Tween-20). The tissue was refixed in 0.4% paraformaldehyde in 1×PBS for 20 minutes, and washed in wash buffer for 5 minutes at 37° C. and dehydrated and air dried at room temperature.

Probe Hybridization: A Hybridization mixture containing: 0.1 µM EB1-turtle probe, 20% formamide, 2×SSC, 0.2 µg/µl BSA, 5% glycerol, and 0.2 µg/µl carrier DNA was added to the slide and covered with a cover glass. The cover glass was sealed to the slide with heat resistant glue. The slide was heated for 2 minutes at 95° C., cooled to 37° C. and incubated at that temperature for 30 minutes. After hybridization, the slide was washed in 2×SSC with 0.05% tween-20 for 5 minutes at 37° C., in wash buffer for 5 minutes at 37° C., and finally dehydrated and air dried at room temperature. Hybridization could be performed at 37° C. without first heating to 95° C., but heating to 95° C. has been found to increase the number of signals. Carrier DNA or RNA may not always be required, but often seems to increase the number of signals.

Figure 7:
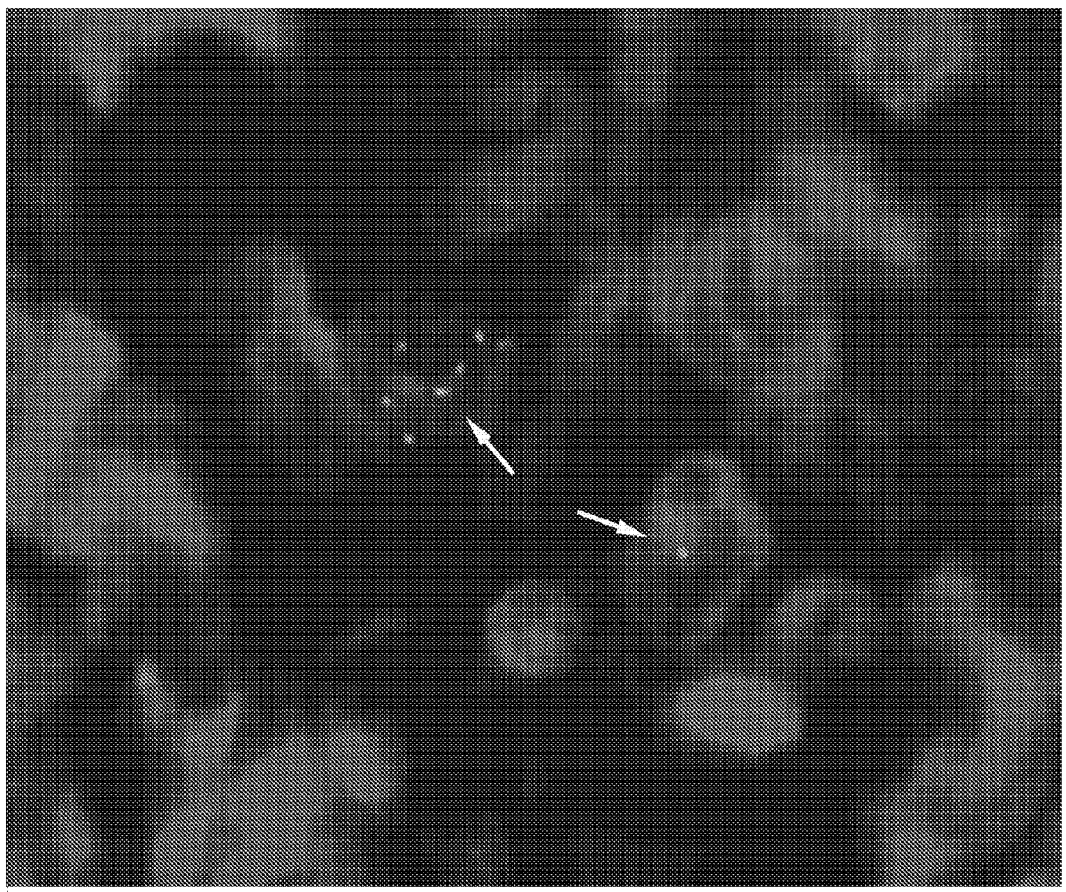
Figure 7:
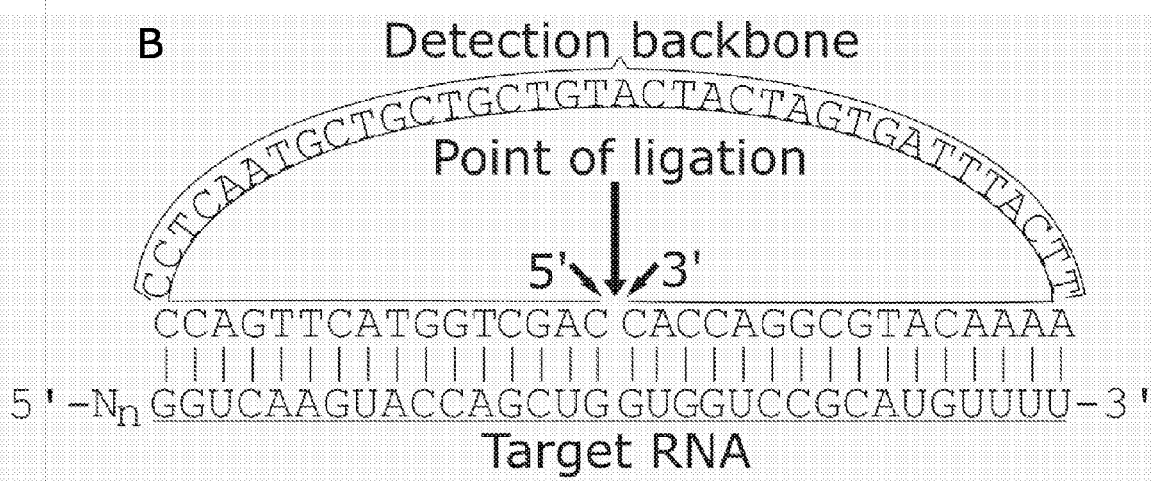

Probe ligation: An advantage of using a turtle probe is that this probe contains its own ligation template, so that probe-ligation is performed on this self-contained DNA template, rather than using the target RNA as template. This probe design will be preferred is most cases since DNA ligation using an RNA template is much less efficient than DNA ligation using a DNA template (compare FIGS. 5 and 7).

Ligation of the probe was performed in a mixture containing: 1×T4 DNA ligase buffer (Fermentas), 0.2 µg/µl BSA, and 0.1 U/µl T4 DNA ligase (Fermentas) for 30 minutes at 37° C. After incubation with the ligase mixture, the slide was washed in wash buffer for 5 minutes at 37° C.

Rolling circle replication: The rolling circle replication uses the probe as rolling circle replication template and commences from the natural 3'-end of the target RNA, making it a target primed rolling circle replication. This procedure detects not only the presence of the target molecule, but also its location inside single cells. Rolling circle replication was performed in a mixture containing: 1×Phi29 reaction buffer (Fermentas), 0.25 mM dNTP, 0.2 µg/µl BSA, 5% glycerol, and 1 U/µl Phi29 DNA polymerase (Fermentas) for 30 minutes at 37° C. After rolling circle replication, the slide was washed in wash buffer for 5 minutes at 37° C.

Detection of rolling circle replication product: Detection of the rolling circle replication product was performed by adding a hybridization mixture containing: 20% formamide, 2×SSC, 5% glycerol, and 0.25 µM fluorescent probe A and 0.25 µM fluorescent probe B, and incubating the slide for 30 minutes at 37° C.

To distinguish between false signals and true signals two fluorescent probes (probe A and probe B) were added, though only one anneals to the rolling circle replication product. The true signals were visible in the spectrum of probe A, whereas false signals, if present, would be detectable in the spectra of both probe A and probe B.

The slide was washed in wash buffer, dehydrated, mounted with VectorShield containing DAPI, and visualized under a fluorescent microscope.

EB1-turtle probe (SEQ ID NO: 3):
5'-P-
GTCGATCCCCTCAATGCTGCTGCTGTACTACAAAACATGCGGACCACCAG
CTGGTACTTGAC CGGATCGACTCGGAATAACCGA-3'
Wherein P is a 5' phosphate Fluorescent probe A (SEQ ID NO: 16):
5'-x-CCTCAATGCTGCTGCTGTACTAC-3'
Wherein x is the fluorophore TAMRA (Rhodamine)

Fluorescent probe B (SEQ ID NO: 17):
5'-y-CCTCAATGCACATGTTTGGCTCC-3'
Wherein y is the fluorophore FAM (FITC)

All probes were purchased from DNA Technology A/S.

Example 4

In Situ Detection of RNA Using a Preformed Circle Probe

Figure 6:
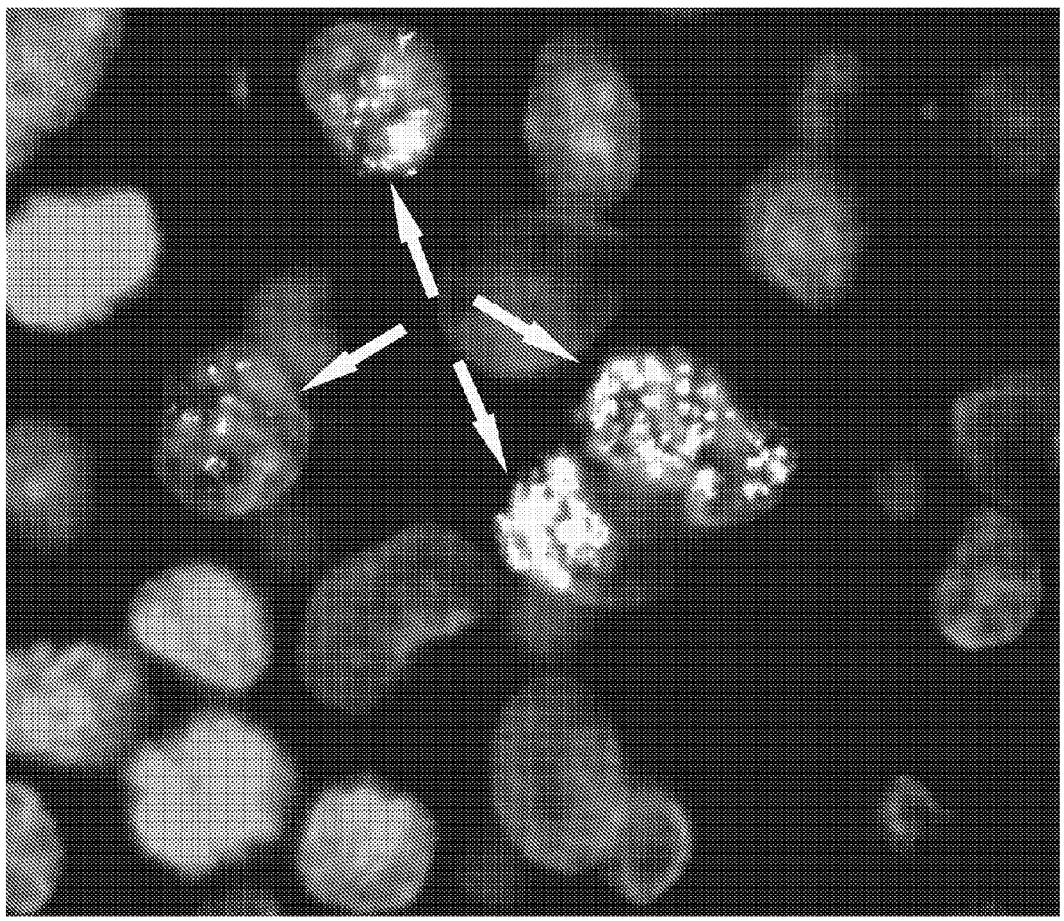
Figure 6:
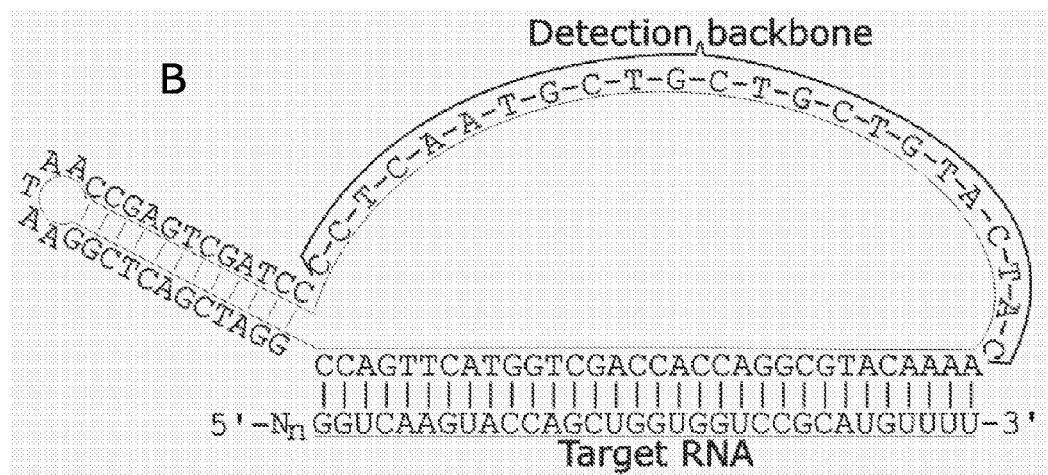

In situ detection of EBER1 (Epstein-Barr Early Region) RNA in paraffin embedded formalin fixed human tonsil tissue infected with Epstein-Barr virus (EBV) (see FIG. 6). The preformed circle was made by ligation of the EB1-turtle probe (FIG. 5) (example 3) before its use as hybridisation probe.

Preparation of Preformed Circle:

The EB1-turtle probe ligated using 1× ligation T4 DNA ligation buffer (Fermentas), 0.1 U/µl T4 DNA ligase (Fermentas) was added to the mixture and the ligation mixture was incubated for 30 minutes at 37° C.

Pretreatment: The formalin fixed paraffin embedded tissue was deparaffinised with xylen for 2×10 minutes and then washed in an ethanol series of 99%, 85%, 70% to remove residual xylen. The tissue was then dehydrated and air dried at room temperature. The tissue was treated with 0.05% pepsin (Sigma) dissolved in 0.1 M HCl for 15 minutes at 37° C. The pepsin treatment was terminated by submerging the slide in wash buffer (0.1 M Tris-HCl, 0.15 M NaCl and 0.05% Tween-20). The tissue was refixed in 0.4% paraformaldehyde in 1×PBS for 20 minutes, and washed in wash buffer for 5 minutes at 37° C. and dehydrated and air dried at room temperature.

Probe Hybridization: A hybridization mixture containing: 0.1 µM preEB1-turtle probe, 20% formamide, 2×SSC, 0.2 µg/µl BSA, 5% glycerol, and 0.2 µg/µl carrier DNA was added to the slide and covered with a cover glass. The cover glass was sealed to the slide with heat resistant glue. The slide was heated for 2 minutes at 95° C., cooled to 37° C. and incubated at that temperature for 30 minutes. After hybridization, the slide was washed in 2×SSC with 0.05% tween-20 for 5 minutes at 37° C., in wash buffer for 5 minutes at 37° C., and finally dehydrated and air dried at room temperature. Hybridization could be performed at 37° C. without first heating to 95° C., but heating to 95° C. has been found to increase the number of signals. Carrier DNA or RNA may not always be required, but often seems to increase the number of signals.

Rolling circle replication: The rolling circle replication uses the probe as rolling circle replication template and commences from the natural 3'-end of the target RNA, making it a target primed rolling circle replication. This procedure detects not only the presence of the target molecule, but also its location inside single cells. Rolling circle replication was performed in a mixture containing: 1×Phi29 reaction buffer (Fermentas), 0.25 mM dNTP, 0.2 µg/µl BSA, 5% glycerol, and 1 U/µl Phi29 DNA polymerase (Fermentas) for 30 minutes at 37° C. After rolling circle replication, the slide was washed in wash buffer for 5 minutes at 37° C.

Detection of rolling circle replication product: Detection of the rolling circle replication product was performed by adding a hybridization mixture containing: 20% formamide, 2×SSC, 5% glycerol, and 0.25 µM fluorescent probe A and 0.25 µM fluorescent probe B, and incubating the slide for 30 minutes at 37° C.

To distinguish between false signals and true signals two fluorescent probes (probe A and probe B) were added, though only one anneals to the rolling circle replication product. The true signals were visible in the spectrum of probe A, whereas false signals, if present, would be detectable in the spectra of both probe A and probe B.

The slide was washed in wash buffer, dehydrated, mounted with VectorShield containing DAPI, and visualized under a fluorescent microscope.

preEB1-turtle probe (SEQ ID NO: 3):
5'-P-
GTCGATCCCCTCAATGCTGCTGCTGTACTACAAAACATGCGGACCACCAG
CTGGTACTTGAC CGGATCGACTCGGAATAACCGA-3'
Wherein P is a 5' phosphate Fluorescent probe A (SEQ ID NO: 16):
5'-x-CCTCAATGCTGCTGCTGTACTAC-3'
Wherein x is the fluorophore TAMRA (Rhodamine)

Fluorescent probe B (SEQ ID NO: 17):
5'-y-CCTCAATGCACATGTTTGGCTCC-3'
Wherein y is the fluorophore FAM (FITC)

All probes were purchased from DNA Technology A/S.

Example 5

In Situ Detection of RNA Using a Padlock Probe

In situ detection of EBER1 (Epstein-Barr Early Region) RNA in paraffin embedded formalin fixed human tonsil tissue infected with Epstein-Barr virus (EBV) (FIG. 7):

Pretreatment: The formalin fixed paraffin embedded tissue was deparaffinised with xylen for 2×10 minutes and then washed in an ethanol series of 99%, 85%, 70% to remove residual xylen. The tissue was then dehydrated and air dried at room temperature. The tissue was treated with 0.05% pepsin (Sigma) dissolved in 0.1 M HCl for 15 minutes at 37° C. The pepsin treatment was terminated by submerging the slide in wash buffer (0.1 M Tris-HCl, 0.15 M NaCl and 0.05% Tween-20). The tissue was refixed in 0.4% paraformaldehyde in 1×PBS for 20 minutes, and washed in wash buffer for 5 minutes at 37° C. and dehydrated and air dried at room temperature.

Probe Hybridization: A hybridization mixture containing: 0.1 µM EB1-padlock probe, 20% formamide, 2×SSC, 0.2 µg/µl BSA, 5% glycerol, and 0.2 µg/µl carrier DNA was added to the slide and covered with a cover glass. The cover glass was sealed to the slide with heat resistant glue. The slide was heated for 2 minutes at 95° C., cooled to 37° C., and incubated at that temperature for 30 minutes. After hybridization the slide was washed in 2×SSC with 0.05% tween-20 for 5 minutes at 37° C., in wash buffer for 5 minutes at 37° C., and finally dehydrated and air dried at room temperature. Hybridization could be performed at 37° C. without first heating to 95° C., but heating to 95° C. has been found to increase the number of signals. Carrier DNA or RNA may not always be required, but often seems to increase the number of signals.

Probe ligation: Ligation of the probe was performed in a mixture containing: 10 mM Tris-HCL (pH7.5 at 25° C.), 10 mM MgCl$_2$, 10 µM ATP, 5 mM DTT, 0.2 µg/µl BSA, and 0.1 U/µl T4 DNA ligase (Fermentas) for 30 minutes at 37° C. After incubation with ligase mixture, the slide was washed in wash buffer for 5 minutes at 37° C. These ligation conditions were optimized for ligating DNA on an RNA template in solution (according to Nilsson M. et al. Nat Biotechnol. 18(7):791-3. (2000)).

Rolling circle replication: The rolling circle replication use the probe as rolling circle replication template and commences from the natural 3'-end of the target RNA making it a target primed rolling circle replication. This procedure detects not only the presence of the target molecule but also its location inside single cells. Rolling circle replication was performed in a mixture containing: 1×Phi29 reaction buffer (Fermentas), 0.25 mM dNTP, 0.2 µg/µl BSA, 5% glycerol and 1 U/µl Phi29 DNA polymerase (Fermentas) for 30 minutes at 37° C. After rolling circle replication the slide was washed in wash buffer for 5 minutes at 37° C.

Detection of rolling circle replication product: Detection of the rolling circle replication product was performed by adding a hybridization mixture containing: 20% formamide, 2×SSC, 5% glycerol, and 0.25 µM fluorescent probe A and 0.25 µM fluorescent probe B, and incubating the slide for 30 minutes at 37° C.

To distinguish between false signals and true signals two fluorescent probes (probe A and probe B) were added, though only one anneals to the rolling circle replication product. The true signals were visible in the spectrum of probe A, whereas false signals, if present, would be detectable in the spectra of both probe A and probe B.

The slide was washed in wash buffer, dehydrated, mounted with VectorShield containing DAPI, and visualized under a fluorescent microscope.

```
EB1-padlock probe (SEQ ID NO: 18):
5'-P-

CAGCTGGTACTTGACCCCTCAATGCTGCTGCTGTACTACTAGTGATTTAC

TTAAAACATGCG GACCAC-3'
Wherein P is a 5' phosphate

Fluorescent probe A (SEQ ID NO: 16):
5'-x-CCTCAATGCTGCTGCTGTACTAC-3'
Wherein x is the fluorophore TAMRA (Rhodamine)

Fluorescent probe B (SEQ ID NO: 17):
5'-y-CCTCAATGCACATGTTTGGCTCC-3'
Wherein y is the fluorophore FAM (FITC)
```

All probes were purchased from DNA Technology A/S.

Example 6

In Situ Detection of RNA Using a Slicer-Turtle Probe

Figure 8:
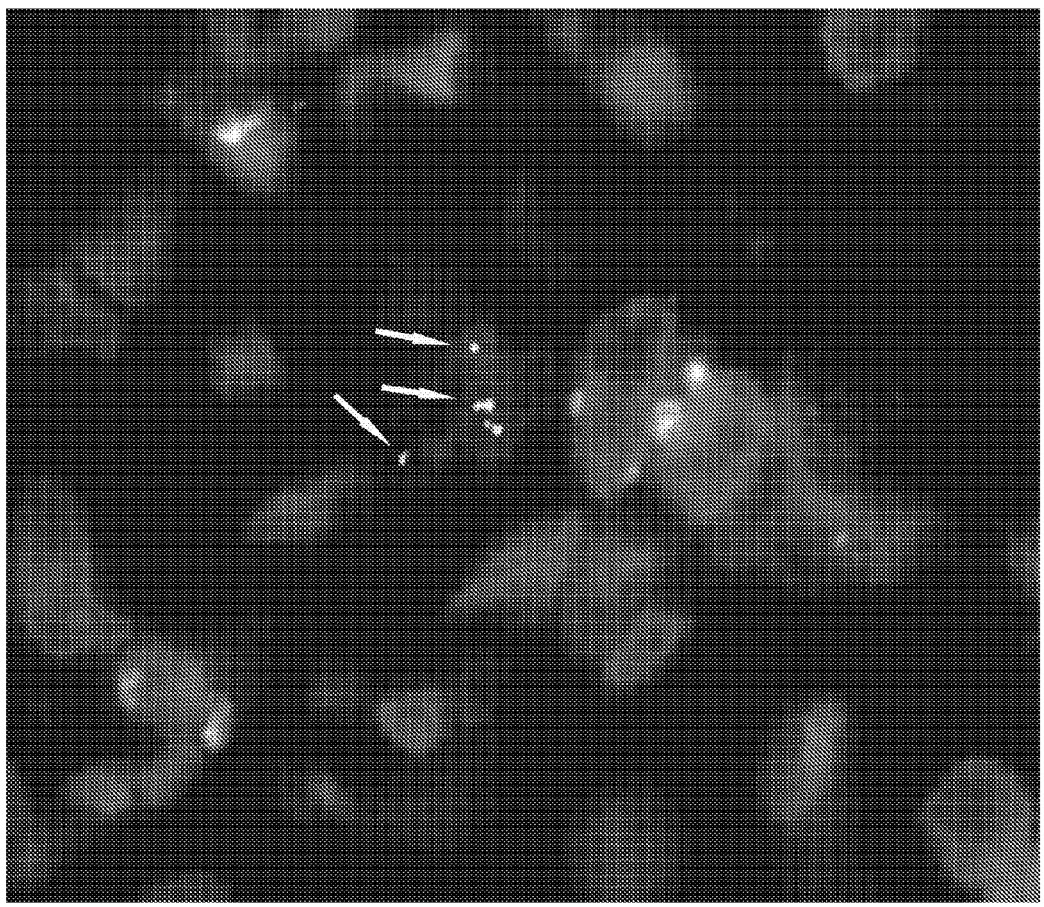
Figure 8:
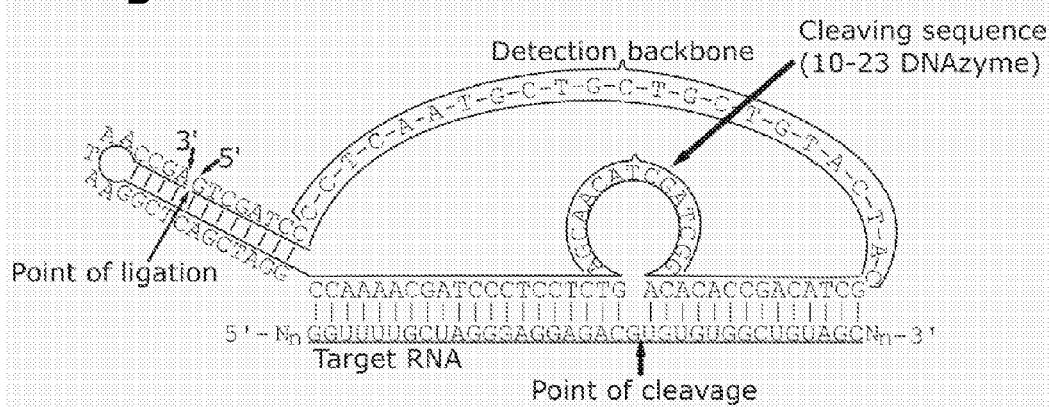
Figure 9:
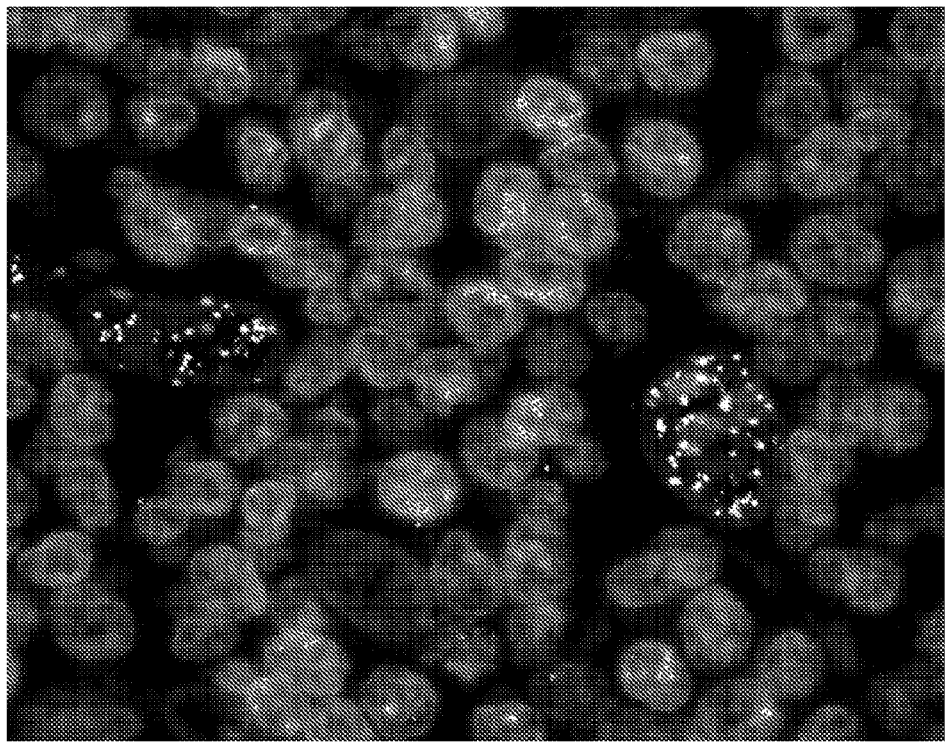
Figure 9:
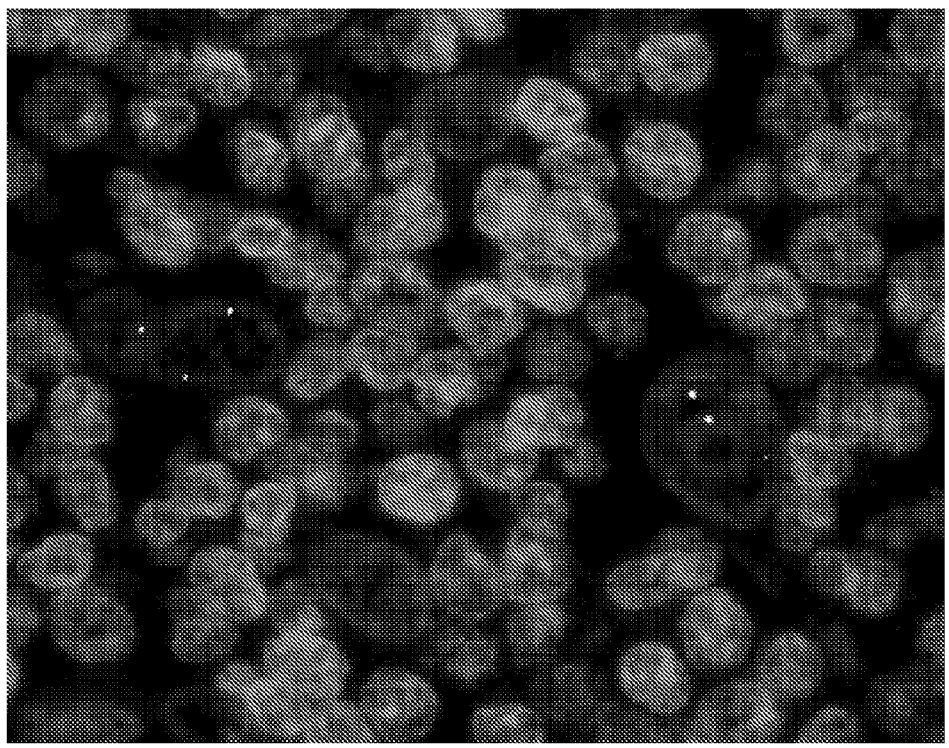

In situ detection of EBER1 (Epstein-Barr Early Region) RNA in paraffin embedded formalin fixed human tonsil tissue infected with Epstein-Barr virus (EBV) using a slicer-turtle probe (FIG. 8).

Pretreatment: The formalin fixed paraffin embedded tissue was deparaffinised with xylen for 2×10 minutes and then washed in an ethanol series of 99%, 85%, 70% to remove residual xylen. The tissue was then dehydrated and air dried at room temperature. The tissue was treated with 0.05% pepsin (Sigma) dissolved in 0.1 M HCl for 15 minutes at 37° C. The pepsin treatment was terminated by submerging the slide in wash buffer (0.1 M Tris-HCl, 0.15 M NaCl and 0.05% Tween-20). The tissue was refixed in 0.4% paraformaldehyde in 1×PBS for 20 minutes, and washed in wash buffer for 5 minutes at 37° C. and dehydrated and air dried at room temperature.

Probe Hybridization: A hybridization mixture containing: 0.1 µM EB1-slicer-turtle probe, 20% formamide, 2×SSC, 0.2 µg/µl BSA, 5% glycerol, and 0.2 µg/µl carrier DNA was added to the slide and covered with a cover glass. The cover glass was sealed to the slide with heat resistant glue. The slide was heated for 2 minutes at 95° C., cooled to 37° C. and incubated at that temperature for 30 minutes. After hybridization, the slide was washed in 2×SSC with 0.05% tween-20 for 5 minutes at 37° C., in wash buffer for 5 minutes at 37° C., and finally dehydrated and air dried at room temperature. Hybridization could be performed at 37° C. without first heating to 95° C., but heating to 95° C. has been found to increase the number of signals. Carrier DNA or RNA may not always be required, but often seems to increase the number of signals.

Probe ligation: An advantage of using a self-templated probe is that this probe contains its own ligation template, so that the probe-ligation is performed on this self-contained DNA template, rather than using the target RNA as template. This probe design will be preferred is most cases since DNA ligation using an RNA template is much less efficient than DNA ligation using a DNA template (compare FIGS. 5 and 7).

Ligation of the probe was performed in a mixture containing: 1×T4 DNA ligase buffer (Fermentas), 0.2 µg/µl BSA, and 0.1 U/µl T4 DNA ligase (Fermentas) for 30 minutes at 37° C. After incubation with the ligase mixture the slide was washed in wash buffer for 5 minutes at 37° C. and finally dehydrated and air dried at room temperature.

The cutting element of this slicer is the 10-23 DNAzyme, which is strictly depended on the presence of divalent metal ions, e.g. $Mg^{2+}$, $Mn^{2+}$, $Ca^{2+}$ or $Pb^{2+}$, for activity. As the 1×T4 DNA ligase buffer contains $Mg^{2+}$ cleavage of the target RNA occurs in parallel with ligation. Cleavage of the target RNA may also be performed during hybridization, or as a separate step as long as divalent metal ions are present.

3'-end modification: Since the 10-23 DNAzyme, produces a cyclic phosphate instead of a regular hydroxyl group at the 3'end, when cleaving RNA, the Phi29 DNA polymerase can not prime from the 3'-end produced (FIG. 4E). Therefore the new 3'-end of the RNA needs to be modified to allow the Phi29 DNA polymerase to commence rolling circle replication. This was done by removing the cyclic phosphate, using the T4 polynucleotide kinase to produce a regular hydroxyl group at the 3' end. This reaction was performed using 1 U/µl T4 polynucleotide kinase (Fermentas) in 1× exchange buffer (Fermentas) supplemented with 0.3 M NaCl, 4 mM ATP, and 0.2 µg/µl BSA for 30 minutes at 37° C. After incubation, the slide was washed in wash buffer for 5 minutes at 37° C.

Rolling circle replication: Rolling circle replication uses the probe as rolling circle template and commences from the new 3'-end of the target RNA making it a target primed rolling circle replication. This procedure detects not only the presence of the target molecule but also its location inside single cells. Rolling circle replication was performed in a mixture containing: 1×Phi29 reaction buffer (Fermentas), 0.25 mM dNTP, 0.2 µg/µl BSA, 5% glycerol and 1 U/µl Phi29 DNA polymerase (Fermentas) for 30 minutes at 37° C. After rolling circle replication the slide was washed in wash buffer for 5 minutes at 37° C.

Detection of rolling circle replication product: Detection of the rolling circle replication product was performed by adding a hybridization mixture containing: 20% formamide, 2×SSC, 5% glycerol, and 0.25 µM fluorescent probe A and 0.25 µM fluorescent probe B, and incubating the slide for 30 minutes at 37° C.

To distinguish between false signals and true signals two fluorescent probes (probe A and probe B) were added, though only one anneals to the rolling circle replication product. The true signals were visible in the spectrum of probe A, whereas false signals, if present, would be detectable in the spectra of both probe A and probe B.

The slide was washed in wash buffer, dehydrated, mounted with VectorShield containing DAPI, and visualized under a fluorescent microscope.

```
EB1-slicer-turtle probe (SEQ ID NO: 19):
5'-P-

GTCGATCCCCTCAATGCTGCTGCTGTACTACCCAAAACGATCCCTCCTCT

GGGCTAGCTACAACGA ACACACCGACATCGGGATCGACTCGGAATAACC

GA-3'
Wherein P is a 5' phosphate

Fluorescent probe A (SEQ ID NO: 16):
5'-x-CCTCAATGCTGCTGCTGTACTAC-3'
Wherein x is the fluorophore TAMRA (Rhodamine)

Fluorescent probe B (SEQ ID NO: 17):
5'-y-CCTCAATGCACATGTTTGGCTCC-3'
Wherein y is the fluorophore FAM (FITC)
```

All probes were purchased from DNA Technology A/S.

Example 7

In Situ Detection of RNA Using Two Different Turtle Probes in Parallel (Multiplexing)

In situ detection of EBER1 (Epstein-Barr Early Region) RNA, and hTR (human telomerase RNA subunit), in paraffin embedded formalin fixed human Hodgkin's lymphoma tissue positive for Epstein-Barr virus (EBV) (see FIG. 5).

Pretreatment: The formalin fixed paraffin embedded tissue was deparaffinised with xylen for 2×10 minutes and then washed in an ethanol series of 99%, 85%, 99% to remove residual xylen and air dried at room temperature. The tissue was treated with 0.05% pepsin (Sigma) dissolved in 0.1 M HCl for 15 minutes at 37° C. The pepsin treatment was terminated by submerging the slide in wash buffer (0.1 M Tris-HCl, 0.15 M NaCl and 0.05% Tween-20). The slide was dehydrated and air dried at room temperature.

Probe Hybridization: A Hybridization mixture containing: 0.1 µM EB1-turtle probe, 0.1 µM hTR-turtle probe, 20% formamide, 2×SSC, 0.2 µg/µl BSA, 5% glycerol, and 1 µg/µl carrier RNA was added to the slide and covered with a cover glass. The cover glass was sealed to the slide with heat resistant glue. The slide was heated for 2 minutes at 95° C., cooled to 37° C. and incubated at that temperature for 30 minutes. After hybridization, the slide was washed in 2×SSC with 0.05% tween-20 for 5 minutes at 37° C., in wash buffer for 5 minutes at 37° C., and finally dehydrated and air dried at room temperature. Hybridization could be performed at 37° C. without first heating to 95° C., but heating to 95° C. has been found to increase the number of signals. Carrier DNA or RNA may not always be required, but often seems to increase the number of signals.

Probe ligation: An advantage of using a turtle probe is that this probe contains its own ligation template, so that probe-ligation is performed on this self-contained DNA template, rather than using the target RNA as template (compare FIGS. 5 and 7).

Ligation of the probe was performed in a mixture containing: 1×T4 DNA ligase buffer (Fermentas), 0.2 µg/µl BSA, and 0.1 U/µl T4 DNA ligase (Fermentas) for 30 minutes at 37° C. After incubation with the ligase mixture, the slide was washed in wash buffer for 5 minutes at 37° C. For easy spreading of the mixture across the tissue, 0.05% Tween-20 and 0.05% NP40 could be added to the mixture.

Rolling circle replication: The rolling circle replication uses the probe as rolling circle replication template and commences from the natural 3'-end of the target RNA, making it a target primed rolling circle replication. This procedure detects not only the presence of the target molecule, but also its location inside single cells. Rolling circle replication was performed in a mixture containing: 1×Phi29 reaction buffer (Fermentas), 0.25 mM dNTP, 0.2 µg/µl BSA, 5% glycerol, and 1 U/µl Phi29 DNA polymerase (Fermentas) for 30 minutes at 37° C. After rolling circle replication, the slide was washed in wash buffer for 5 minutes at 37° C.

Detection of rolling circle replication product: Detection of the rolling circle replication product was performed by adding a hybridization mixture containing: 20% formamide, 2×SSC, 5% glycerol, and 0.25 µM fluorescent probe A and 0.25 µM fluorescent probe B, and incubating the slide for 30 minutes at 37° C.

The slide was washed in wash buffer, dehydrated, mounted with VectorShield containing DAPI, and visualized under a fluorescent microscope.

```
EB1-turtle probe (SEQ ID NO: 3):
5'-P-

GTCGATCCCCTCAATGCTGCTGCTGTACTACAAAACATGCGGACCACCAG

CTGGTACTTGAC CGGATCGACTCGGAATAACCGA-3'
Wherein P is a 5' phosphate hTR-turtle probe (SEQ ID NO: 5):
5'-P-

GTCGATCCCCTCAATGCTGCTGCTGTACTACGCATGTGTGAGCCGAGTCC

TGGGTGCACGTCCCACA

GCTCGGATCGACTCGGAATAACCGA-3'
Wherein P is a 5' phosphate

Fluorescent probe A (SEQ ID NO: 16):
5'-x-CCTCAATGCTGCTGCTGTACTAC-3'
Wherein x is the fluorophore TAMRA (Rhodamine)

Fluorescent probe B (SEQ ID NO: 17):
5'-y-CCTCAATGCACATGTTTGGCTCC-3'
Wherein y is the fluorophore FAM (FITC)
```

All probes were purchased from DNA Technology A/S.

REFERENCES

WO 97/19193
WO 97/20948
WO 98/38300
WO 99/49079
WO 01/77383
WO 02/50310
US2003/0087241
Andersen C L. et al. *Chromosome Res.* 10(4), 305-12 (2002)
Astrom H. et al. Org Biomol Chem. 7; 1(9):1461-5 (2003)
Brown A K et al. Biochemistry 17; 42(23):7152-61 (2003)

Carmi N. et al. Proc Natl Acad Sci USA. 3; 95(5):2233-7 (1998)

Dahl F et al., Proc Natl Acad Sci USA. 101(13), 4548-53 (2004)

Huang L. et al. 3 Biol Inorg Chem. 5(1):85-92 (2000)

Jimenez-Garrido N et al. 3 Inorg Biochem. 99(3):677-89 (2005)

Koch J. Chromosoma 98:259 (1989).

Larsson C. et al. Nature Methods 1, 227-32 (2004))

Masuda N. et al. Nucleic Acids Res. 15; 27(22) 4436-43 (1999)

Nilsson M. et al. Nat Biotechnol. 18(7):791-3. (2000)

Sakamoto S. et al. Nucleic Acids Res. 1; 31(5):1416-25 (2003)

Santoro S W and Joyce G F Proc Natl Acad Sci USA. 29; 94(9):4262-6. (1997)

Whitney A. et al. Chem Commun (Camb). 7; (1):36-7 (2003)

The invention claimed is:

1. A circular nucleic acid probe for targeting a nucleic acid sequence, said probe having a total length of 30-200 nucleotides comprising:
   I a first part and a third part comprising nucleic acid sequences that are at least 75% complementary to each other and each having a length of from 3 to 100 nucleotides;
   II a second nucleic acid part comprising a hairpin structure extending either from said first part or from said third part, wherein said second part has a length of from 9 to 50 nucleotides; and
   III a fourth part comprising a sequence of nucleic acid residues, which is at least 75% complementary to the target nucleic acid sequence, wherein the length of said fourth part is from 6 to 100 nucleotides, wherein said probe comprises one or more elements having endonuclease activity, and wherein the one or more elements having endonuclease activity is positioned internally in a target complementary sequence, dividing it into two or more parts.

2. The circular nucleic acid probe according to claim 1, wherein said fourth part comprises a sequence of nucleic acid residues which is at least 75% complementary to a target RNA sequence.

3. The circular nucleic acid probe according to claim 1, further comprising one or more elements defining the specific probe.

4. The circular nucleic acid probe according to claim 3, wherein the element defining the specific probe is a nucleotide sequence of from 6 to 150 nucleotides.

5. The circular nucleic acid probe according to claim 3, wherein the element defining the specific probe is composed of one or more artificial nucleotides.

6. The circular nucleic acid probe according to claim 1, wherein said element having endonuclease activity is a DNAzyme.

7. A circular nucleic acid probe, which is a preformed circle probe or a padlock probe, wherein said probe comprises one or more elements having endonuclease activity, and wherein the one or more elements having endonuclease activity is positioned internally in a target complementary sequence, dividing it into two or more parts, said circular nucleic acid comprising:
   i) one or more parts, each part comprising a sequence of nucleic acid residues which is at least 75% complementary to a region of the target nucleic acid sequence; and
   ii) an element defining the specific probe, wherein the specific probe is a nucleotide sequence of from 6 to 150 nucleotides or wherein the specific probe is composed of one or more artificial nucleotides.

8. The circular nucleic acid probe according to claim 7, wherein the total length of the one or more parts comprising at least 75% complementary to a region of a target nucleic acid sequence is from 6 to 100 nucleotides.

9. The circular nucleic acid probe according to claim 7, wherein the total length of said probe is from 30 to 200 nucleotides.

10. The circular nucleic acid probe for targeting a nucleic acid sequence, said probe having a total length of 30-200 nucleotides comprising:
   I a first part and a third part comprising nucleic acid sequences that are at least 75% complementary each other and each having a length of from 3 to 100 nucleotides;
   II a second nucleic acid part comprising a hairpin structure extending either from said first part or from said third part, wherein said second part has a length of from 9 to 50 nucleotides; and
   III a fourth part comprising a sequence of nucleic acid residues, which is at least 75% complementary to the target nucleic acid sequence, wherein the length of said fourth part is from 6 to 100 nucleotides,
wherein said probe comprises one or more elements having endonuclease activity, and wherein the one or more elements having endonuclease activity is positioned internally in a target complementary sequence, dividing it into two or more parts, or
the circular nucleic acid probe, which is a preformed circle probe or a padlock probe, wherein said probe comprises one or more elements having endonuclease activity, and wherein the one or more elements having endonuclease activity is positioned internally in the target complementary sequence, dividing it into two or more parts,
wherein said element having endonuclease activity is a reactive chemical group.

11. The circular nucleic acid probe according to claim 10, wherein said reactive chemical group is selected from the group consisting of Terpyridine-Cu(II), 5-amino-2,9-dimethylphenanthroline-Zn(II), Tetraazamacrocycles-Eu(III), and Neocuproine-Zn(II).

12. A kit of parts comprising a circular nucleic acid probe for targeting a nucleic acid sequence, said probe having a total length of 30-200 nucleotides comprising:
   I a first part and a third part comprising nucleic acid sequences that are at least 75% complementary each other and each having a length of from 3 to 100 nucleotides;
   II a second nucleic acid part comprising a hairpin structure extending either from said first part or from said third part, wherein said second part has a length of from 9 to 50 nucleotides; and
   III a fourth part comprising a sequence of nucleic acid residues, which is at least 75% complementary to the target nucleic acid sequence, wherein the length of said fourth part is from 6 to 100 nucleotides,
wherein said probe comprises one or more elements having endonuclease activity, and wherein the one or more elements having endonuclease activity is positioned internally in a target complementary sequence, dividing it into two or more parts or a circular nucleic acid probe, which is a preformed circle probe or a padlock probe, wherein said probe comprises one or more elements having endonuclease activity, and wherein the one or more elements having endonuclease activity is positioned internally in the target complementary sequence, dividing it into two or more parts and at least one further component selected from the group consisting of buffers, reagents, antibodies and control preparations of one or more target nucleic acids.

13. A method for the detection of target DNA or RNA molecules, said method comprising the steps of:
   i) hybridising the circular nucleic acid probe for targeting a nucleic acid sequence, said probe having a total length of 30-200 nucleotides comprising:
      I a first part and a third part comprising nucleic acid sequences that are at least 75% complementary each other and each having a length of from 3 to 100 nucleotides;
      II a second nucleic acid part comprising a hairpin structure extending either from said first part or from said third part, wherein said second part has a length of from 9 to 50 nucleotides; and
      III a fourth part comprising a sequence of nucleic acid residues, which is at least 75% complementary to the target nucleic acid sequence, wherein the length of said fourth part is from 6 to 100 nucleotides,
   wherein said probe comprises one or more elements having endonuclease activity, and wherein the one or more elements having endonuclease activity is positioned internally in a target complementary sequence, dividing it into two or more parts or the circular nucleic acid probe, which is a preformed circle probe or a padlock probe, wherein said probe comprises one or more elements having endonuclease activity, and wherein the one or more elements having endonuclease activity is positioned internally in the target complementary sequence, dividing it into two or more parts with target DNA sequence, at or near the 3'-end of the target DNA molecule;
   ii) performing rolling circle replication; and
   iii) detecting the rolling circle product.

14. The method of claim 13 comprising the steps of:
   I obtaining a preparation containing the target RNA molecule;
   II providing the circular nucleic acid probe;
   III hybridising said probe with the target RNA molecule at or near the 3'-end of said target RNA molecule;
   IV effecting rolling circle replication with said probe as template; and
   V detecting said target RNA molecule by visualising the rolling circle product.

15. The method of claim 13, wherein the method further comprises the step of ligating the probe to form a closed circular structure.

16. The method of claim 13, wherein the detection of said target RNA molecule occurs in situ in cells or tissue.

17. The method of claim 13, wherein said target RNA is immobilised on a solid support.

18. The method of claim 17 further comprising the steps of:
   i) providing a capture oligonucleotide attached to a solid support; and
   ii) hybridising said capture oligonucleotide with said target nucleic acid molecule, thereby attaching the target nucleic acid molecule to the solid support.

19. The method of claim 18, wherein the capture oligonucleotide is directly synthesised on the support.

20. The method of claim 18, wherein the capture oligonucleotide is labelled with a marker and attached to the solid support through binding of the marker to a receptor molecule immobilised on the solid support.

21. The method of claim 18, wherein the target nucleic acid molecule is attached to the solid support through an antibody.

22. The method of claim 21, wherein the target RNA molecule is attached to the solid support through an antibody targeting the 5'-cap of the nucleic acid molecule.

23. The method of claim 13, wherein said circular nucleic acid probe hybridizes 25 nucleotides or less from the 3'-end of the target nucleic acid molecule.

24. The method of claim 13 further comprising recessing the 3'-end of the target nucleic acid molecule with an enzyme comprising 3'->5' exonuclease activity.

25. The method of claim 24, wherein said enzyme comprising 3'->5' exonuclease activity is selected from the group consisting of polymerases with 3'->5' exonuclease activity and exonucleases with 3'->5' exonuclease activity.

26. The method of claim 25, wherein said enzyme comprising 3'->5' exonuclease activity is an exonuclease comprising 3'->5' exonuclease activity.

27. The method of claim 25, wherein said enzyme comprising 3'->5' exonuclease activity is a DNA polymerase comprising 3'->5' exonuclease activity.

28. The method of claim 13, wherein the preparation comprising the target nucleic acid molecule is obtained from cells selected from the group consisting of mammalian cells, bacterial cells, yeast cells, reptile cells, amphibian cells, avian cells and plant cells.

29. The method of claim 28, wherein the cells are mammalian cells.

30. The method of claim 29, wherein the cells are human cells.

31. The method of claim 13, wherein the preparation comprising the target nucleic acid molecule is obtained from tissue selected from the group consisting of mammalian tissue, reptile tissue, amphibian tissue, avian tissue and plant tissue.

32. The method of claim 31, wherein the tissue is mammalian tissue.

33. The method of claim 32, wherein the tissue is human tissue.

34. The method of claim 13 wherein the preparation comprising the target nucleic acid molecule is obtained from virus.

35. The method of claim 13, wherein the amount of target nucleic acid molecules is measured quantitatively by counting the number of rolling circle replication signals.

36. The method of claim 13, wherein the amount of target nucleic acid molecules is measured quantitatively based on the measurement of the amount of fluorescence signal from the rolling circle replication.

37. A method for the detection of a target nucleic acid molecule, said method comprising the steps of i) hybridising a probe, which is a circular nucleic acid probe for targeting a nucleic acid sequence, said probe having a total length of 30-200 nucleotides comprising:
   I a first part and a third part comprising nucleic acid sequences that are at least 75% complementary each other and each having a length of from 3 to 100 nucleotides;
   II a second nucleic acid part comprising a hairpin structure extending either from said first part or from said third part, wherein said second part has a length of from 9 to 50 nucleotides; and
   III a fourth part comprising a sequence of nucleic acid residues, which is at least 75% complementary to the target nucleic acid sequence, wherein the length of said fourth part is from 6 to 100 nucleotides,
wherein said probe comprises one or more elements having endonuclease activity, and
wherein the one or more elements having endonuclease activity is positioned internally in a target complementary sequence, dividing it into two or more parts or
a circular nucleic acid probe, which is a preformed circle probe or a padlock probe, wherein said probe comprises one or more elements having endonuclease activity, and wherein the one or more elements having endonuclease activity is positioned internally in the target complementary sequence, dividing it into two or more parts, to a target nucleic acid molecule;
ii) cleaving said target nucleic acid molecule with the element having endonuclease activity to produce a 3'-end within the target nucleic acid molecule;
iii) performing rolling circle replication from said new 3'-end; and
iv) detecting the rolling circle product.

38. The method of claim 37, wherein said target nucleic acid molecule is an RNA molecule.

39. The method of claim 37, said method comprising:
   i) obtaining a preparation comprising the target nucleic acid molecule;
   ii) providing the circular nucleic acid probe;
   iii) hybridising said probe with the target nucleic acid molecule;
   iv) cleaving the target nucleic acid molecule with the element having endonuclease activity, thereby producing a new 3'-end and 5'-end within the nucleic acid molecule;
   v) effecting rolling circle replication from said new 3'-end within the target nucleic acid molecule with said probe as a template; and
   vi) detecting said target nucleic acid molecule by visualising the rolling circle product.

40. The method of claim 37, wherein said probe is a circular nucleic acid probe for targeting a nucleic acid sequence, said probe having a total length of 30-200 nucleotides comprising:
   I a first part and a third part comprising nucleic acid sequences that are at least 75% complementary each other and each having a length of from 3 to 100 nucleotides;
   II a second nucleic acid part comprising a hairpin structure extending either from said first part or from said third part, wherein said second part has a length of from 9 to 50 nucleotides; and
   III a fourth part comprising a sequence of nucleic acid residues, which is at least 75% complementary to the target nucleic acid sequence, wherein the length of said fourth part is from 6 to 100 nucleotides, wherein said probe comprises one or more elements having endonuclease activity, and wherein the one or more elements having endonuclease activity is positioned internally in a target complementary sequence, dividing it into two or more parts or a circular nucleic acid probe, which is a preformed circle probe or a padlock probe, wherein said probe comprises one or more elements having endonuclease activity, and wherein the one or more elements having endonuclease activity is positioned internally in the target complementary sequence, dividing it into two or more parts, and wherein the method comprises the further step of ligating said probe to form a closed circular structure.

41. The method of claim 37, wherein said target nucleic acid molecule is detected in situ in cells or tissue.

42. The method of claim 37, wherein said target nucleic acid molecule is immobilised on a solid support.

43. The method of claim 42, wherein said target nucleic acid molecule is RNA.

44. The method of claim 42 further comprising the steps of:
  i) providing a capture oligonucleotide attached to a solid support; and
  ii) hybridising said capture oligonucleotide with said target nucleic acid molecule, thereby attaching the target nucleic acid molecule to the solid support.

45. The method of claim 44, wherein the capture oligonucleotide is directly synthesised on the support.

46. The method of claim 44, wherein the capture oligonucleotide is labelled with a marker and attached to the solid support through binding of the marker to a receptor molecule immobilised on the solid support.

47. The method of claim 44, wherein the target nucleic acid molecule is attached to the solid support through an antibody.

48. The method of claim 44, wherein the target RNA molecule is attached to the solid support through an antibody targeting the 5'-cap of the nucleic acid molecule.

49. The method of claim 37, wherein said new 3'-end of the target nucleic acid molecule is modified to obtain a free hydroxyl group.

50. The method of claim 49, wherein said new 3'-end of the target nucleic acid molecule is modified by the T4 polynucleotide kinase.

51. The method of claim 37, wherein said new 3'-end of the target nucleic acid molecule is modified by an enzyme comprising 3'->5' exonuclease activity.

52. The method of claim 51, wherein said enzyme comprising 3'->5' exonuclease activity is selected from the group consisting of polymerases with 3'->5' exonuclease activity and exonucleases with 3'->5' exonuclease activity.

53. The method of claim 52, wherein said enzyme comprising 3'->5' exonuclease activity is an exonuclease comprising 3'->5' exonuclease activity.

54. The method of claim 52, wherein said enzyme comprising 3'->5' exonuclease activity is a DNA polymerase comprising 3'->5' exonuclease activity.

55. A diagnostic method comprising the steps of
  i) hybridising a circular nucleic acid probe for targeting a nucleic acid sequence,
    said probe having a total length of 30-200 nucleotides comprising:
      I a first part and a third part comprising nucleic acid sequences that are at least 75% complementary each other and each having a length of from 3 to 100 nucleotides;
      II a second nucleic acid part comprising a hairpin structure extending either from said first part or from said third part, wherein said second part has a length of from 9 to 50 nucleotides; and
      III a fourth part comprising a sequence of nucleic acid residues, which is at least 75% complementary to the target nucleic acid sequence, wherein the length of said fourth part is from 6 to 100 nucleotides,
    wherein said probe comprises one or more elements having endonuclease activity, and wherein the one or more elements having endonuclease activity is positioned internally in a target complementary sequence, dividing it into two or more parts or
    the circular nucleic acid probe, which is a preformed circle probe or a padlock probe, wherein said probe comprises one or more elements having endonuclease activity, and wherein the one or more elements having endonuclease activity is positioned internally in the target complementary sequence, dividing it into two or more parts
    with target DNA sequence, at or near the 3'-end of the target DNA molecule; to a target nucleic acid molecule; and
  ii) detecting said hybridisation.

56. The diagnostic method of claim 55, wherein said target nucleic acid molecule is RNA.

57. The diagnostic method of claim 55, wherein the detection of the target nucleic acid molecule is carried out according to the method for the detection of target DNA or RNA molecules, said method comprising the steps of:
  i) hybridising the circular nucleic acid probe for targeting a nucleic acid sequence, said probe having a total length of 30-200 nucleotides comprising:
    I a first part and a third part comprising nucleic acid sequences that are at least 75% complementary each other and each having a length of from 3 to 100 nucleotides;
    II a second nucleic acid part comprising a hairpin structure extending either from said first part or from said third part, wherein said second part has a length of from 9 to 50 nucleotides; and
    III a fourth part comprising a sequence of nucleic acid residues, which is at least 75% complementary to the target nucleic acid sequence, wherein the length of said fourth part is from 6 to 100 nucleotides,
  wherein said probe comprises one or more elements having endonuclease activity, and wherein the one or more elements having endonuclease activity is positioned internally in a target complementary sequence, dividing it into two or more parts or
  the circular nucleic acid probe, which is a preformed circle probe or a padlock probe, wherein said probe comprises one or more elements having endonuclease activity, and wherein the one or more elements having endonuclease activity is positioned internally in the target complementary sequence, dividing it into two or more parts with target DNA sequence, at or near the 3'-end of the target DNA molecule;
  ii) performing rolling circle replication; and
  iii) detecting the rolling circle product.

* * * * *

```
                         SEQUENCE LISTING

<160> NUMBER OF SEQ ID NOS: 23

<210> SEQ ID NO 1
<211> LENGTH: 84
<212> TYPE: DNA
<213> ORGANISM: Artificial Sequence
<220> FEATURE:
<223> OTHER INFORMATION: Turtle probe

<400> SEQUENCE: 1
gtcgatcccc tcaatgcaca tgtttggctc caaaacatgc ggaccaccag ctggtacttg      60
accggatcga ctcggaataa ccga                                            84

<210> SEQ ID NO 2
<211> LENGTH: 85
<212> TYPE: DNA
<213> ORGANISM: Artificial Sequence
<220> FEATURE:
<223> OTHER INFORMATION: Turtle probe

<400> SEQUENCE: 2
gtcgatcccc tcaatgcaca tgtttggctc caaaaatagc ggacaagccg aatacccttc      60
tcccggatcg actcggaata accga                                           85

<210> SEQ ID NO 3
<211> LENGTH: 84
<212> TYPE: DNA
<213> ORGANISM: Artificial Sequence
<220> FEATURE:
<223> OTHER INFORMATION: Turtle probe

<400> SEQUENCE: 3
gtcgatcccc tcaatgctgc tgctgtacta caaaacatgc ggaccaccag ctggtacttg      60
accggatcga ctcggaataa ccga                                            84

<210> SEQ ID NO 4
<211> LENGTH: 85
<212> TYPE: DNA
<213> ORGANISM: Artificial Sequence
<220> FEATURE:
<223> OTHER INFORMATION: Turtle probe

<400> SEQUENCE: 4
gtcgatcccc tcaatgctgc tgctgtacta caaaaatagc ggacaagccg aatacccttc      60
tcccggatcg actcggaata accga                                           85

<210> SEQ ID NO 5
<211> LENGTH: 92
<212> TYPE: DNA
<213> ORGANISM: Artificial Sequence
<220> FEATURE:
<223> OTHER INFORMATION: Turtle probe
```

<400> SEQUENCE: 5
gtcgatcccc tcaatgctgc tgctgtacta cgcatgtgtg agccgagtcc tgggtgcacg    60
tcccacagct cggatcgact cggaataacc ga    92

<210> SEQ ID NO 6
<211> LENGTH: 101
<212> TYPE: DNA
<213> ORGANISM: Artificial Sequence
<220> FEATURE:
<223> OTHER INFORMATION: Slicer-turtle probe

<400> SEQUENCE: 6
gtcgatcccc tcaatgctgc tgctgtacta cgctacagcc acacaggcta gctacaacga    60
gtctcctccc tagcaaaacc ggatcgactc ggaataaccg a    101

<210> SEQ ID NO 7
<211> LENGTH: 101
<212> TYPE: DNA
<213> ORGANISM: Artificial Sequence
<220> FEATURE:
<223> OTHER INFORMATION: Slicer-turtle probe

<400> SEQUENCE: 7
gtcgatcccc tcaatgcaca tgtttggctc ctcggtagca ccgcaggcta gctacaacga    60
tgagcgttgg cggtgtgtcc ggatcgactc ggaataaccg a    101

<210> SEQ ID NO 8
<211> LENGTH: 117
<212> TYPE: DNA
<213> ORGANISM: Artificial Sequence
<220> FEATURE:
<223> OTHER INFORMATION: Slicer-padlock probe

<400> SEQUENCE: 8
catcgggaga agctcataga tttatttcct caatgctgct gctgtactac tagtgattta    60
cttggatgtc tgacagtcta ggctagctac aacgatggtt tgcagagacc cagtggc    117

<210> SEQ ID NO 9
<211> LENGTH: 112
<212> TYPE: DNA
<213> ORGANISM: Artificial Sequence
<220> FEATURE:
<223> OTHER INFORMATION: Slicer-padlock probe

<400> SEQUENCE: 9
ccatgtcaaa atcactccca tttatttcct caatgctgct gctgtactac tagtgattta    60
cttggatgtc tgtaaagaga ggctagctac aacgagatgg cacctggcac cc    112

<210> SEQ ID NO 10
<211> LENGTH: 112
<212> TYPE: DNA
<213> ORGANISM: Artificial Sequence
<220> FEATURE:
<223> OTHER INFORMATION: Slicer-padlock probe

<400> SEQUENCE: 10
tacttcatcg catctttgtg tttatttcct caatgctgct gctgtactac tagtgattta    60
cttggatgtc tagggaaaag gctagctaca acgataagaa attcgatgct gc    112

<210> SEQ ID NO 11
<211> LENGTH: 111
<212> TYPE: DNA

```
<213> ORGANISM: Artificial Sequence
<220> FEATURE:
<223> OTHER INFORMATION: Slicer-padlock probe

<400> SEQUENCE: 11
taattactga ttgtgtatct tttatttcct caatgctgct gctgtactac tagtgattta      60
cttggatgtc tagaacgtag gctagctaca acgaaaatag tagtcatttg c              111

<210> SEQ ID NO 12
<211> LENGTH: 86
<212> TYPE: DNA
<213> ORGANISM: Artificial Sequence
<220> FEATURE:
<223> OTHER INFORMATION: Slicer-padlock probe

<400> SEQUENCE: 12
ctagcaaaac ctctcctcaa tgctgctgct gtactactag tgatttactt tacagccagg      60
ctagctacaa cgaacacgtc tcctcc                                          86

<210> SEQ ID NO 13
<211> LENGTH: 88
<212> TYPE: DNA
<213> ORGANISM: Artificial Sequence
<220> FEATURE:
<223> OTHER INFORMATION: Slicer-padlock probe

<400> SEQUENCE: 13
cgcactgagc gttcctcaat gctgctgctg tactactagt gatttacttg gacttgaggc      60
tagctacaac gactcgggtc ggtagcac                                        88

<210> SEQ ID NO 14
<211> LENGTH: 257
<212> TYPE: RNA
<213> ORGANISM: Artificial Sequence
<220> FEATURE:
<223> OTHER INFORMATION: In vitro transcribed RNA

<400> SEQUENCE: 14
gggauaaaua caaagaugcg augaaguagc agcaucgaau uucuuaguuu ucccucuuaa      60
caacuuuuua uaaguauaua uauaagauac acaaucagua auuagcaaau gacuacuauu     120
uguacguucu caucgucaua agccagaguu uaauuaagug ccucaaccgg gaugcgauuu     180
cgcguucaua uacaaagccg aaaugacaau aagaaaguca ucgccaaaca acacgacccu     240
uuagugaggg uuaauug                                                   257

<210> SEQ ID NO 15
<211> LENGTH: 35
<212> TYPE: DNA
<213> ORGANISM: Artificial Sequence
<220> FEATURE:
<223> OTHER INFORMATION: Biotinylated capture oligonucleotide
<220> FEATURE:
<221> NAME/KEY: misc_feature
<222> LOCATION: (35)..(35)
<223> OTHER INFORMATION: Bionylated nucleotide

<400> SEQUENCE: 15
agagggaaaa ctaagaaatt cgatgctgct acttc                                35

<210> SEQ ID NO 16
<211> LENGTH: 23
<212> TYPE: DNA
<213> ORGANISM: Artificial Sequence
<220> FEATURE:
```

```
<223> OTHER INFORMATION: Flourescent probe
<220> FEATURE:
<221> NAME/KEY: misc_feature
<222> LOCATION: (1)..(1)
<223> OTHER INFORMATION: TAMRA (rhodamine) attached to nucleotide

<400> SEQUENCE: 16
cctcaatgct gctgctgtac tac                                             23

<210> SEQ ID NO 17
<211> LENGTH: 23
<212> TYPE: DNA
<213> ORGANISM: Artificial Sequence
<220> FEATURE:
<223> OTHER INFORMATION: Flourescent probe
<220> FEATURE:
<221> NAME/KEY: misc_feature
<222> LOCATION: (1)..(1)
<223> OTHER INFORMATION: FAM attached to nucleotide

<400> SEQUENCE: 17
cctcaatgca catgtttggc tcc                                             23

<210> SEQ ID NO 18
<211> LENGTH: 68
<212> TYPE: DNA
<213> ORGANISM: Artificial Sequence
<220> FEATURE:
<223> OTHER INFORMATION: Padlock probe

<400> SEQUENCE: 18
cagctggtac ttgacccctc aatgctgctg ctgtactact agtgatttac ttaaaacatg     60
cggaccac                                                              68

<210> SEQ ID NO 19
<211> LENGTH: 101
<212> TYPE: DNA
<213> ORGANISM: Artificial Sequence
<220> FEATURE:
<223> OTHER INFORMATION: Slicer-turtle probe

<400> SEQUENCE: 19
gtcgatcccc tcaatgctgc tgctgtacta cccaaaacga tccctcctct gggctagcta     60
caacgaacac accgacatcg ggatcgactc ggaataaccg a                        101

<210> SEQ ID NO 20
<211> LENGTH: 92
<212> TYPE: DNA
<213> ORGANISM: Artificial Sequence
<220> FEATURE:
<223> OTHER INFORMATION: Turtle probe

<400> SEQUENCE: 20
gtcgatcccc tcaatgctgc tgctgtacta cgcatgtgtg agccgagtcc tgggtgcacg     60
tcccacagct cggatcgact cggaataacc ga                                   92

<210> SEQ ID NO 21
<211> LENGTH: 16
<212> TYPE: DNA
<213> ORGANISM: Artificial Sequence
<220> FEATURE:
<223> OTHER INFORMATION: 10-23 DNAzyme
<220> FEATURE:
<221> NAME/KEY: misc_feature
<222> LOCATION: (1)..(1)
<223> OTHER INFORMATION: n is a or g
```

```
<400> SEQUENCE: 21
nggctagcta caacga                                                          16

<210> SEQ ID NO 22
<211> LENGTH: 15
<212> TYPE: DNA
<213> ORGANISM: Artificial Sequence
<220> FEATURE:
<223> OTHER INFORMATION: 8-17 Family
<220> FEATURE:
<221> NAME/KEY: misc_feature
<222> LOCATION: (2)..(2)
<223> OTHER INFORMATION: n is any natural or modified nucleotide
      including modified nucleotides
<220> FEATURE:
<221> NAME/KEY: misc_feature
<222> LOCATION: (3)..(3)
<223> OTHER INFORMATION: n is any natural or modified nucleotide
      including modified nucleotides
<220> FEATURE:
<221> NAME/KEY: misc_feature
<222> LOCATION: (4)..(4)
<223> OTHER INFORMATION: n is any natural or modified nucleotide
      including modified nucleotides
<220> FEATURE:
<221> NAME/KEY: misc_feature
<222> LOCATION: (8)..(8)
<223> OTHER INFORMATION: n is any natural or modified nucleotide
      including modified nucleotides
<220> FEATURE:
<221> NAME/KEY: misc_feature
<222> LOCATION: (9)..(9)
<223> OTHER INFORMATION: n is any natural or modified nucleotide
      including modified nucleotides
<220> FEATURE:
<221> NAME/KEY: misc_feature
<222> LOCATION: (10)..(10)
<223> OTHER INFORMATION: n is any natural or modified nucleotide
      including modified nucleotides

<400> SEQUENCE: 22
tnnnagcnnn wcgaa                                                           15

<210> SEQ ID NO 23
<211> LENGTH: 15
<212> TYPE: DNA
<213> ORGANISM: Artificial Sequence
<220> FEATURE:
<223> OTHER INFORMATION: 17E DNAzyme

<400> SEQUENCE: 23
tccgagccgg tcgaa                                                           15
```